United States Patent
Finch, Jr.

(10) Patent No.: US 11,690,991 B2
(45) Date of Patent: Jul. 4, 2023

(54) GRAFT-PORT HEMODIALYSIS SYSTEMS, DEVICES, AND METHODS

(71) Applicant: Proviflo, LLC, Clinton, MS (US)

(72) Inventor: Charles David Finch, Jr., Clinton, MS (US)

(73) Assignee: PROVIFLO, LLC, Clinton, MS (US)

( * ) Notice: Subject to any disclaimer, the term of this patent is extended or adjusted under 35 U.S.C. 154(b) by 825 days.

(21) Appl. No.: 16/586,067

(22) Filed: Sep. 27, 2019

(65) Prior Publication Data

US 2020/0038645 A1    Feb. 6, 2020

Related U.S. Application Data

(63) Continuation of application No. 15/179,688, filed on Jun. 10, 2016, now Pat. No. 10,456,570.
(Continued)

(51) Int. Cl.
*A61M 39/02*    (2006.01)
*A61M 1/28*    (2006.01)
(Continued)

(52) U.S. Cl.
CPC ........ *A61M 39/0247* (2013.01); *A61M 1/285* (2013.01); *A61M 1/3653* (2013.01);
(Continued)

(58) Field of Classification Search
CPC .. A61M 1/3653; A61M 1/285; A61M 1/3659; A61M 2039/0018;
(Continued)

(56) References Cited

U.S. PATENT DOCUMENTS 3,998,222 A    12/1976 Shihata
4,015,601 A    4/1977 Bokros et al.
(Continued)

FOREIGN PATENT DOCUMENTS

EP    1550479 A2    7/2005
EP    2300071 A    3/2011
(Continued)

OTHER PUBLICATIONS

Ash et al., "Concentrated Citrate (23%) for Catheter Lock Solution", Asaio Journal, vol. 46, Issue 2, 2000, 3 pages.
(Continued)

*Primary Examiner* — Brandy S Lee
(74) *Attorney, Agent, or Firm* — Kilpatrick Townsend & Stockton LLP

(57) ABSTRACT

The disclosure relates to a subcutaneously implanted port device for establishing access to the vascular system of a patient requiring multiple blood treatments over an extended period of time. The systems, devices and methods disclosed herein may reduce miscannulation, promote intra-session hemostasis, and decrease the incidence of bacteremia and sepsis among other improvements and advantages. The devices include a port with a tapered seat for receiving an access tube, the first tapered seat having a proximal portion, a distal portion, and a conical section extending between the proximal portion and the distal portion; and an interface surface configured to engage a blood vessel or a vascular access catheter. The proximal portion of the tapered seat is configured to receive the access tube therethrough, and the tapered seat creates a mismatch fit with a diameter of the access tube when in use for an increase in flow during treatment.

25 Claims, 38 Drawing Sheets

Related U.S. Application Data

(60) Provisional application No. 62/174,384, filed on Jun. 11, 2015.

(51) Int. Cl.
| | | |
|---|---|---|
| *A61M 1/36* | (2006.01) | |
| *A61M 5/42* | (2006.01) | |
| *A61M 39/22* | (2006.01) | |
| *B29C 45/00* | (2006.01) | |
| *A61M 39/00* | (2006.01) | |
| *B29L 31/00* | (2006.01) | |

(52) U.S. Cl.
CPC ............ *A61M 5/427* (2013.01); *A61M 39/22* (2013.01); *B29C 45/0081* (2013.01); *A61M 2039/0018* (2013.01); *A61M 2039/027* (2013.01); *A61M 2039/0258* (2013.01); *A61M 2039/0273* (2013.01); *A61M 2039/0285* (2013.01); *A61M 2039/0291* (2013.01); *A61M 2205/583* (2013.01); *A61M 2207/00* (2013.01); *B29K 2995/006* (2013.01); *B29L 2031/753* (2013.01)

(58) Field of Classification Search
CPC .... A61M 2039/0258; A61M 2039/027; A61M 2039/0273; A61M 2039/0285; A61M 2039/0291; A61M 2205/583; A61M 2207/00; A61M 39/0247; A61M 39/22; A61M 5/427; A61M 1/3661
See application file for complete search history.

(56) References Cited

U.S. PATENT DOCUMENTS

| | | | |
|---|---|---|---|
| 4,108,173 | A | 8/1978 | Slivenko et al. |
| 4,114,325 | A | 9/1978 | Hochstein |
| 4,181,132 | A | 1/1980 | Parks |
| 4,496,343 | A | 1/1985 | Prosl et al. |
| 4,534,759 | A | 8/1985 | Trawoger |
| 4,569,675 | A | 2/1986 | Prosl et al. |
| 4,778,452 | A | 10/1988 | Moden et al. |
| 4,929,242 | A | 5/1990 | Desecki et al. |
| 4,983,162 | A | 1/1991 | Metais et al. |
| 5,053,013 | A | 10/1991 | Ensminger et al. |
| 5,057,084 | A | 10/1991 | Ensminger et al. |
| 5,077,281 | A | 12/1991 | Reinmuller |
| 5,120,313 | A | 6/1992 | Elftman |
| 5,180,365 | A | 1/1993 | Ensminger et al. |
| 5,226,879 | A | 7/1993 | Ensminger et al. |
| 5,263,930 | A | 11/1993 | Ensminger |
| 5,281,199 | A | 1/1994 | Ensminger et al. |
| 5,306,255 | A | 4/1994 | Haindl |
| 5,350,360 | A | 9/1994 | Ensminger et al. |
| 5,417,656 | A | 5/1995 | Ensminger et al. |
| 5,421,814 | A | 6/1995 | Geary |
| 5,476,451 | A | 12/1995 | Ensminger et al. |
| 5,503,630 | A | 4/1996 | Ensminger et al. |
| 5,520,643 | A | 5/1996 | Ensminger et al. |
| 5,527,277 | A | 6/1996 | Ensminger et al. |
| 5,527,278 | A | 6/1996 | Ensminger et al. |
| 5,562,617 | A | 10/1996 | Kuiper et al. |
| 5,637,088 | A | 6/1997 | Wenner et al. |
| 5,702,363 | A | 12/1997 | Flaherty |
| 5,704,915 | A | 1/1998 | Melsky et al. |
| 5,741,228 | A | 4/1998 | Lambrecht et al. |
| 5,755,780 | A | 5/1998 | Finch et al. |
| 5,807,356 | A | 9/1998 | Finch et al. |
| 5,954,691 | A | 9/1999 | Prosl |
| 5,989,239 | A | 11/1999 | Finch et al. |
| 6,007,516 | A | 12/1999 | Burbank et al. |
| 6,022,335 | A | 2/2000 | Ramadan |
| 6,261,257 | B1 | 7/2001 | Uflacker et al. |
| 6,423,706 | B2 | 7/2002 | Sodemann |
| 6,582,409 | B1 | 6/2003 | Squitieri |
| 6,635,243 | B1 | 10/2003 | Gaponyuk et al. |
| 6,679,870 | B1 | 1/2004 | Finch et al. |
| 6,685,694 | B2 | 2/2004 | Finch et al. |
| 6,824,532 | B2 | 11/2004 | Gillis et al. |
| 6,958,049 | B1 | 10/2005 | Ash |
| 7,056,316 | B1 | 6/2006 | Burbank et al. |
| 7,131,192 | B2 | 11/2006 | Stanford |
| 7,473,240 | B2 | 1/2009 | Peavey |
| 7,803,143 | B2 | 9/2010 | Tallarida et al. |
| 7,806,122 | B2 | 10/2010 | Hoendervoogt et al. |
| 8,151,801 | B2 | 4/2012 | Hoendervoogt et al. |
| 8,348,909 | B2 | 1/2013 | Haase et al. |
| 10,456,570 | B2 | 10/2019 | Finch |
| 2003/0175323 | A1 | 9/2003 | Utterberg et al. |
| 2004/0068233 | A1 | 4/2004 | DiMatteo et al. |
| 2004/0181192 | A1 | 9/2004 | Cuppy et al. |
| 2004/0199220 | A1* | 10/2004 | Cantlon ............ A61M 5/14276 607/60 |
| 2005/0037048 | A1 | 2/2005 | Song |
| 2005/0043673 | A1 | 2/2005 | Lieberman |
| 2005/0085778 | A1 | 4/2005 | Parks et al. |
| 2005/0181008 | A1 | 8/2005 | Hunter et al. |
| 2005/0209573 | A1* | 9/2005 | Brugger ............ A61M 39/0208 604/288.03 |
| 2006/0020212 | A1 | 1/2006 | Xu et al. |
| 2006/0024360 | A1 | 2/2006 | Chen |
| 2006/0052757 | A1 | 3/2006 | Fischer et al. |
| 2006/0062850 | A1 | 3/2006 | Chen et al. |
| 2006/0094690 | A1 | 5/2006 | Prosl |
| 2006/0177477 | A1 | 8/2006 | Ash et al. |
| 2006/0253063 | A1 | 11/2006 | Schweikert |
| 2006/0257390 | A1 | 11/2006 | Semba |
| 2007/0016162 | A1 | 1/2007 | Burbank et al. |
| 2007/0083156 | A1 | 4/2007 | Muto et al. |
| 2007/0255234 | A1 | 11/2007 | Haase et al. |
| 2007/0265584 | A1 | 11/2007 | Hickman et al. |
| 2007/0292355 | A1 | 12/2007 | Tamarkin et al. |
| 2008/0058729 | A1 | 3/2008 | Loughnane et al. |
| 2008/0118544 | A1 | 5/2008 | Wang |
| 2010/0249747 | A1 | 9/2010 | Mills et al. |
| 2011/0264104 | A1 | 10/2011 | Naoum |
| 2011/0311602 | A1 | 12/2011 | Mills et al. |
| 2012/0157924 | A1* | 6/2012 | Schutz .................. A61M 39/26 604/175 |
| 2014/0018721 | A1 | 1/2014 | Gage et al. |
| 2014/0024998 | A1 | 1/2014 | Prosl et al. |
| 2014/0128792 | A1 | 5/2014 | Li et al. |
| 2016/0361529 | A1 | 12/2016 | Finch |

FOREIGN PATENT DOCUMENTS

| | | |
|---|---|---|
| EP | 2686033 A2 | 1/2014 |
| EP | 3307374 A2 | 4/2018 |
| WO | 9519200 A1 | 7/1995 |
| WO | 9631246 A1 | 10/1996 |
| WO | 9747338 A1 | 12/1997 |
| WO | 9835710 A2 | 8/1998 |
| WO | 9938438 A1 | 8/1999 |
| WO | 200001391 A1 | 1/2000 |
| WO | 2007061787 A2 | 5/2007 |
| WO | 2009152488 A1 | 12/2009 |
| WO | 2010015001 A1 | 2/2010 |
| WO | 2012125927 A2 | 9/2012 |
| WO | 2016201269 A2 | 12/2016 |
| WO | 2016201269 A3 | 2/2017 |
| WO | 2016201269 A8 | 4/2017 |

OTHER PUBLICATIONS

Dogra et al., "Prevention of Tunneled Hemodialysis Catheter-Related Infections Using Catheter-Restricted Filling with Gentamicin and Citrate: A Randomized Controlled Study", Journal of the American Society of Nephrology, vol. 13, Issue 8, 2002, pp. 2133-2139.

European Patent Application No. 16808403.6, Extended European Search Report dated Mar. 11, 2019, 10 pages.

(56) References Cited

OTHER PUBLICATIONS

Mandolfo et al., "Catheter lock solutions: it's time for a change", The journal Vascular Access, vol. 7, 2006, pp. 99-102.
Meeus et al., "A Prospective, Randomized, Double-Blind Crossover Study on the Use of 5% Citrate lock versus 10% Citrate Lock in Permanent Hemodialysis Catheters", Blood Purification, vol. 232, Issue 2, 2005, pp. 101-105.
International Patent Application No. PCT/US2016/036950, International Search Report and Written Opinion dated Dec. 28, 2016, 12 pages.
International Patent Application No. PCT/US2016/036950, Invitation to Pay Additional Fees and Partial Search Report dated Oct. 19, 2016, 2 pages.

* cited by examiner

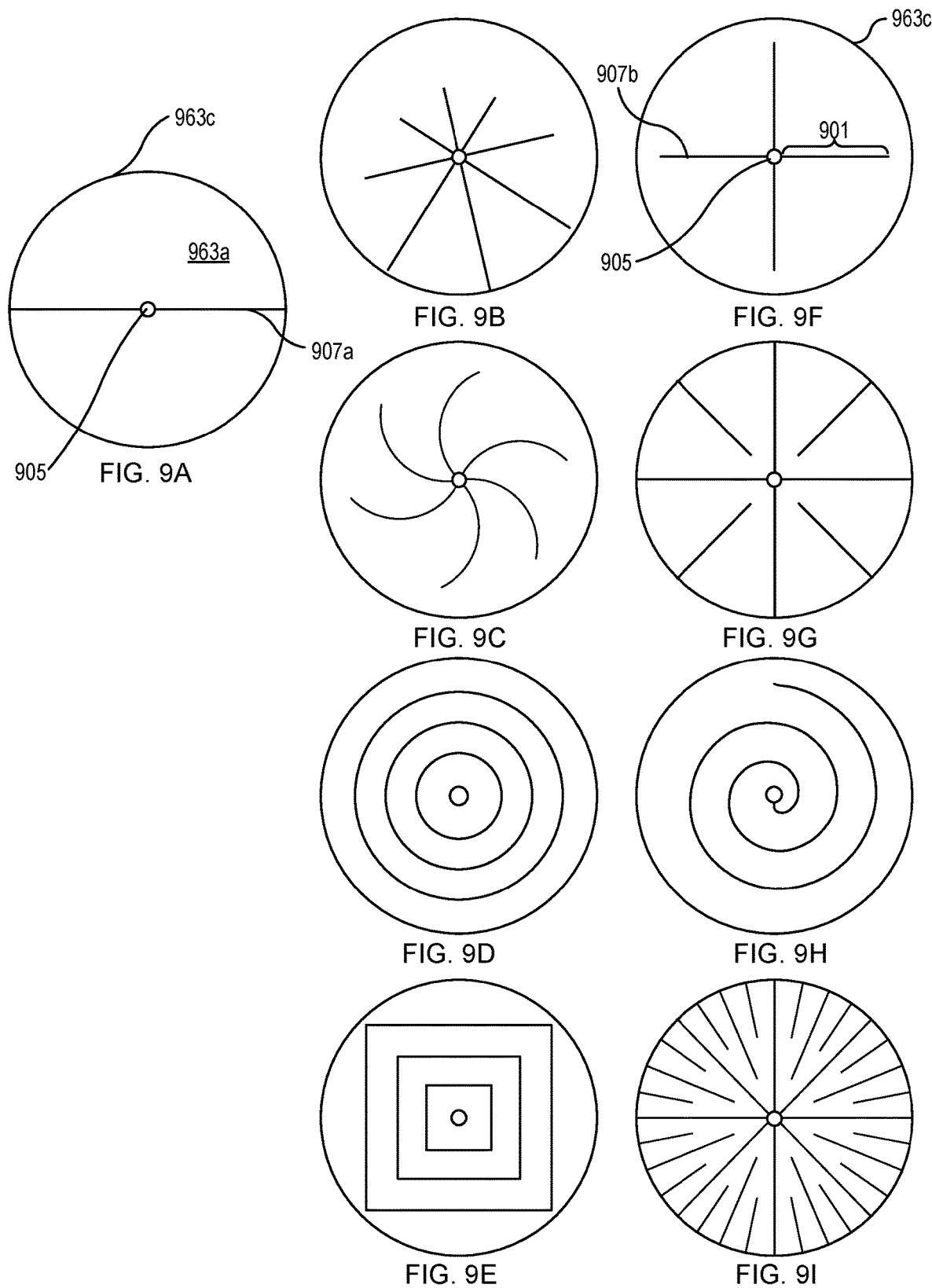

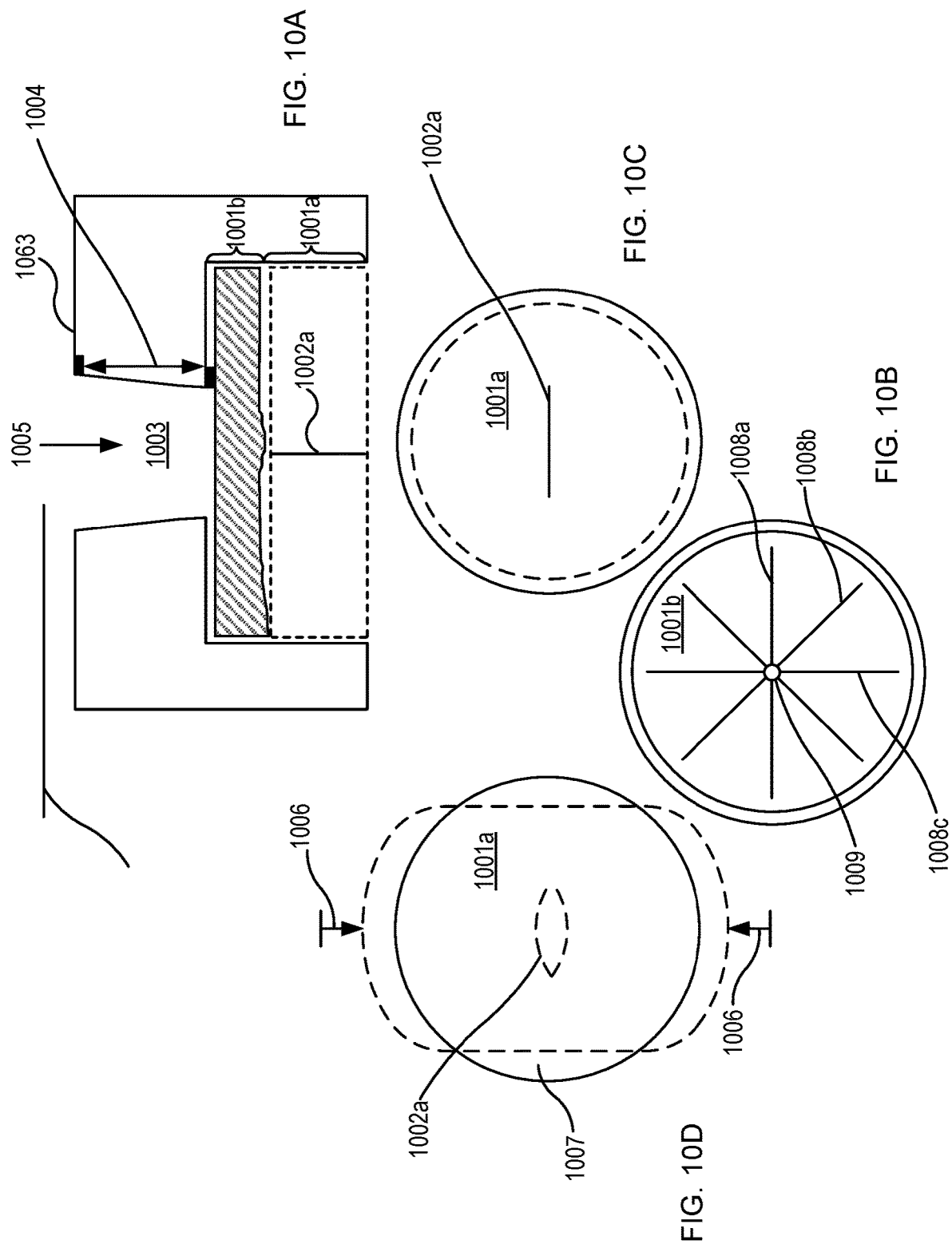

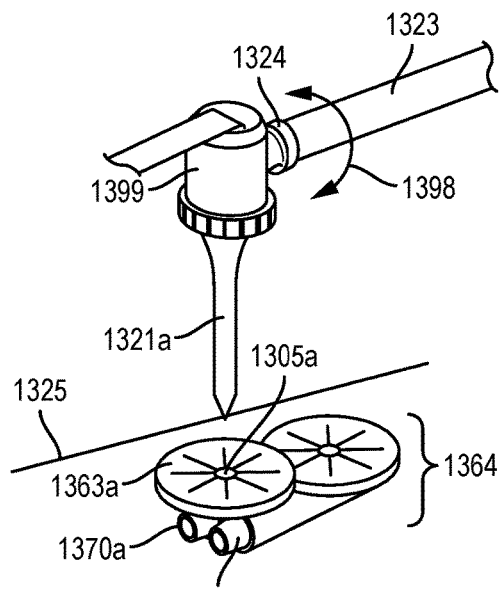
FIG. 13C1
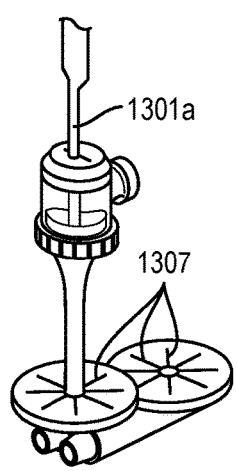
FIG. 13C2
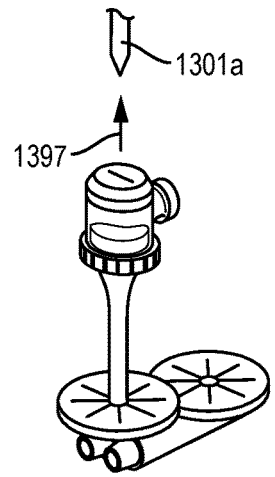
FIG. 13C3
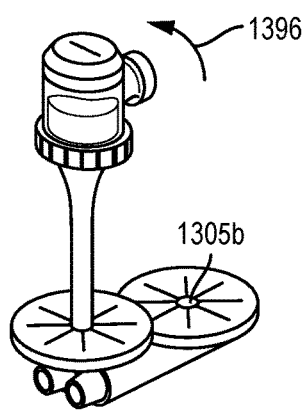
FIG. 13C4
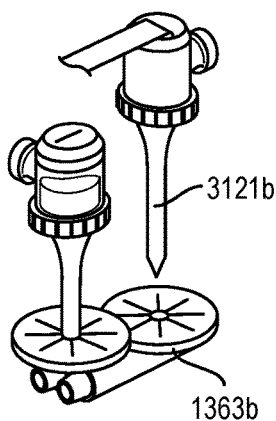
FIG. 13C5
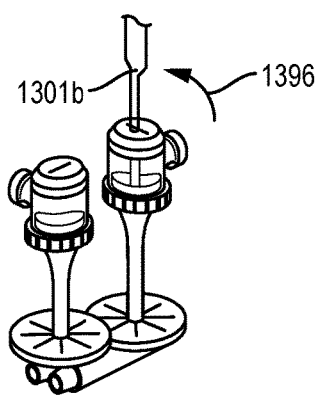
FIG. 13C6
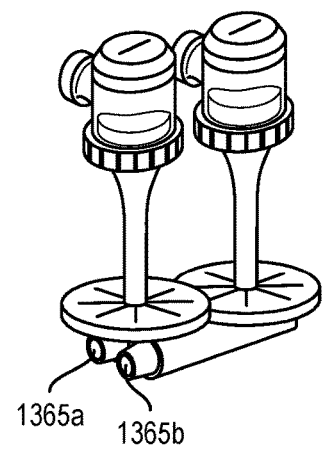
FIG. 13C7

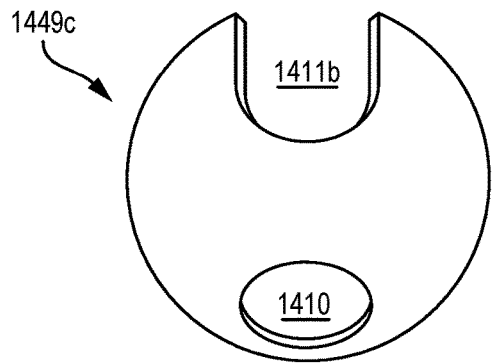
FIG. 14D1
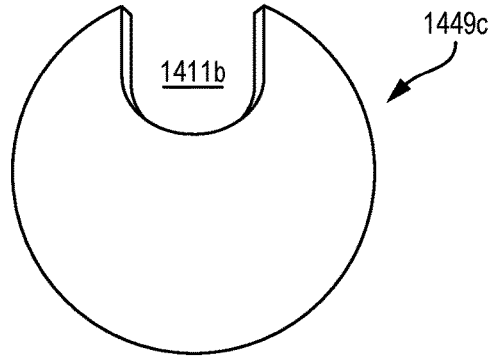
FIG. 14D2
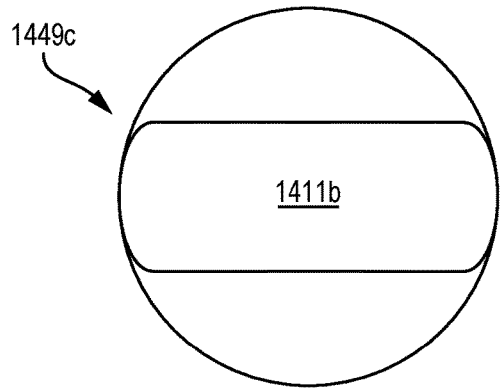
FIG. 14D3
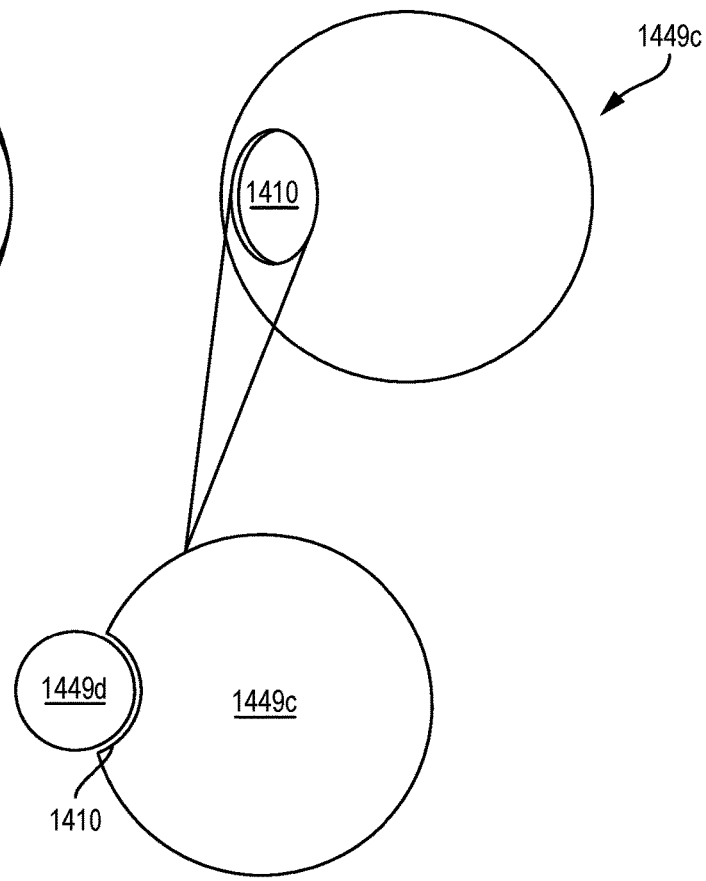
FIG. 14D4

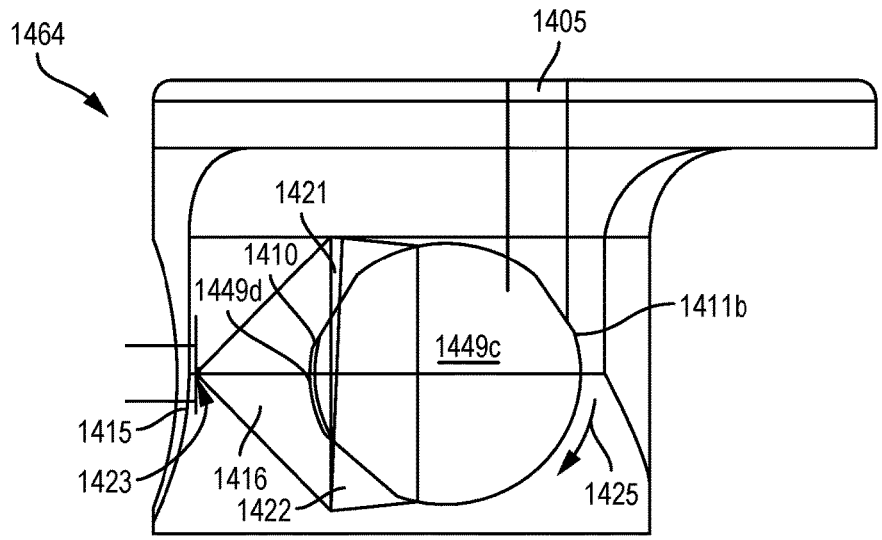
FIG. 14E1
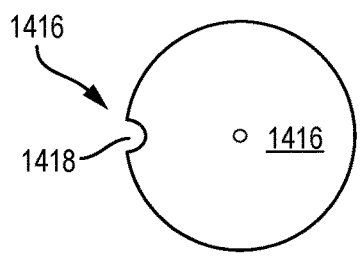
FIG. 14E2
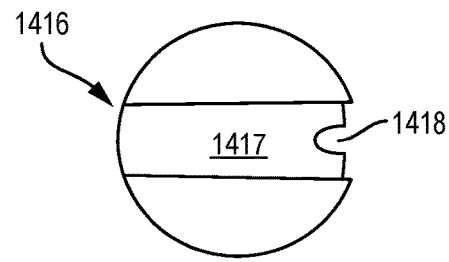
FIG. 14E3
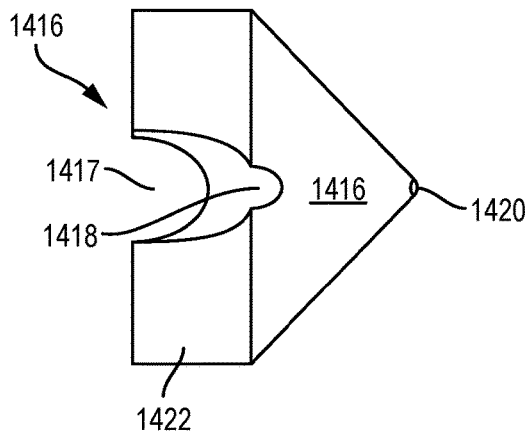
FIG. 14E4
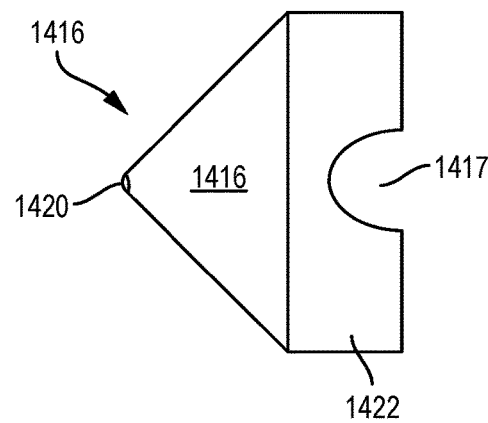
FIG. 14E5

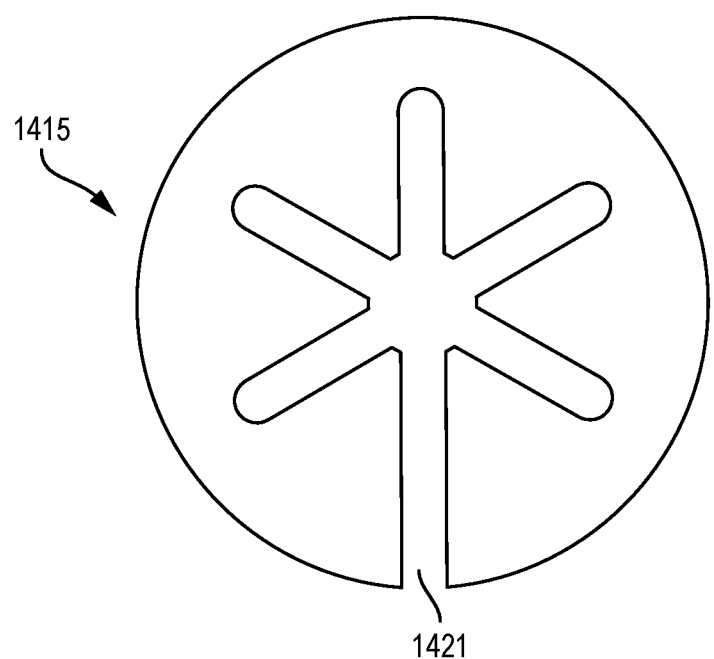
FIG. 14E6

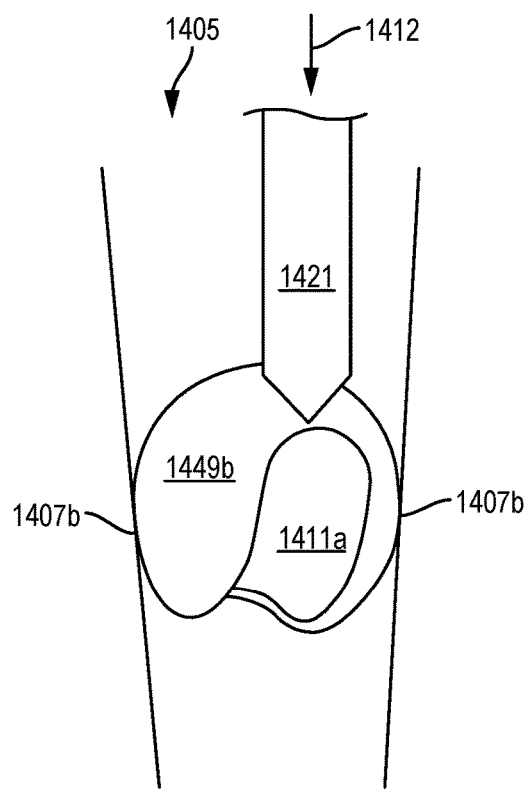
FIG. 14G1
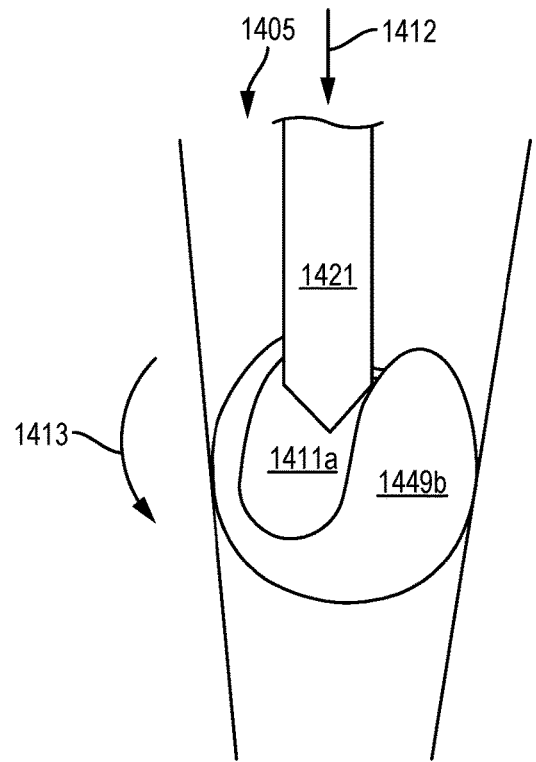
FIG. 14G2
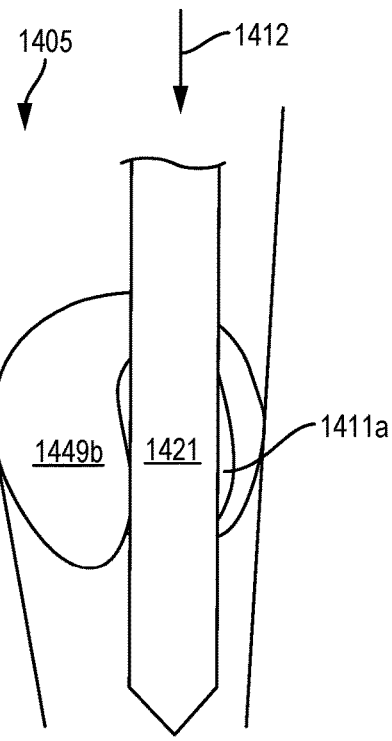
FIG. 14G3

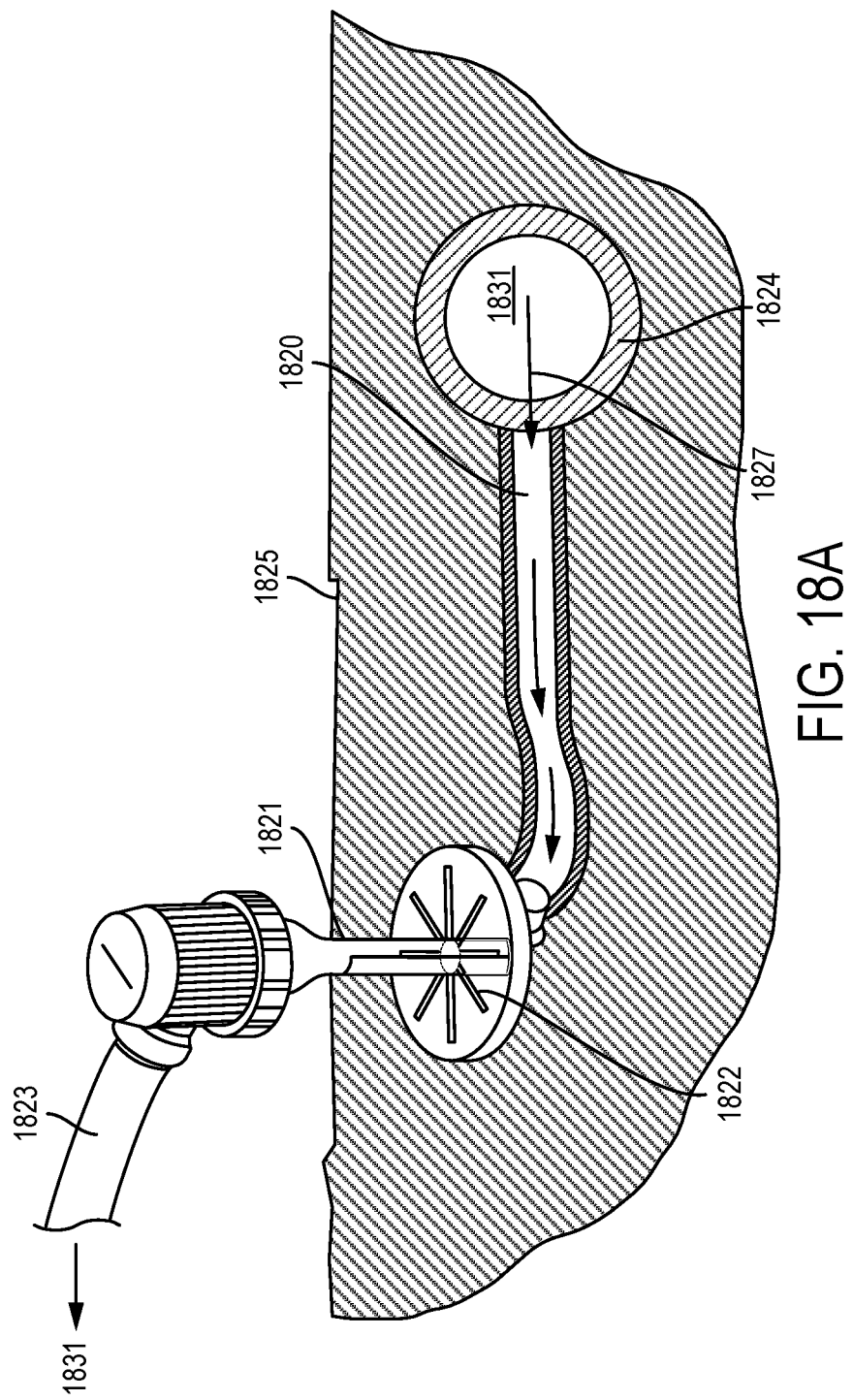

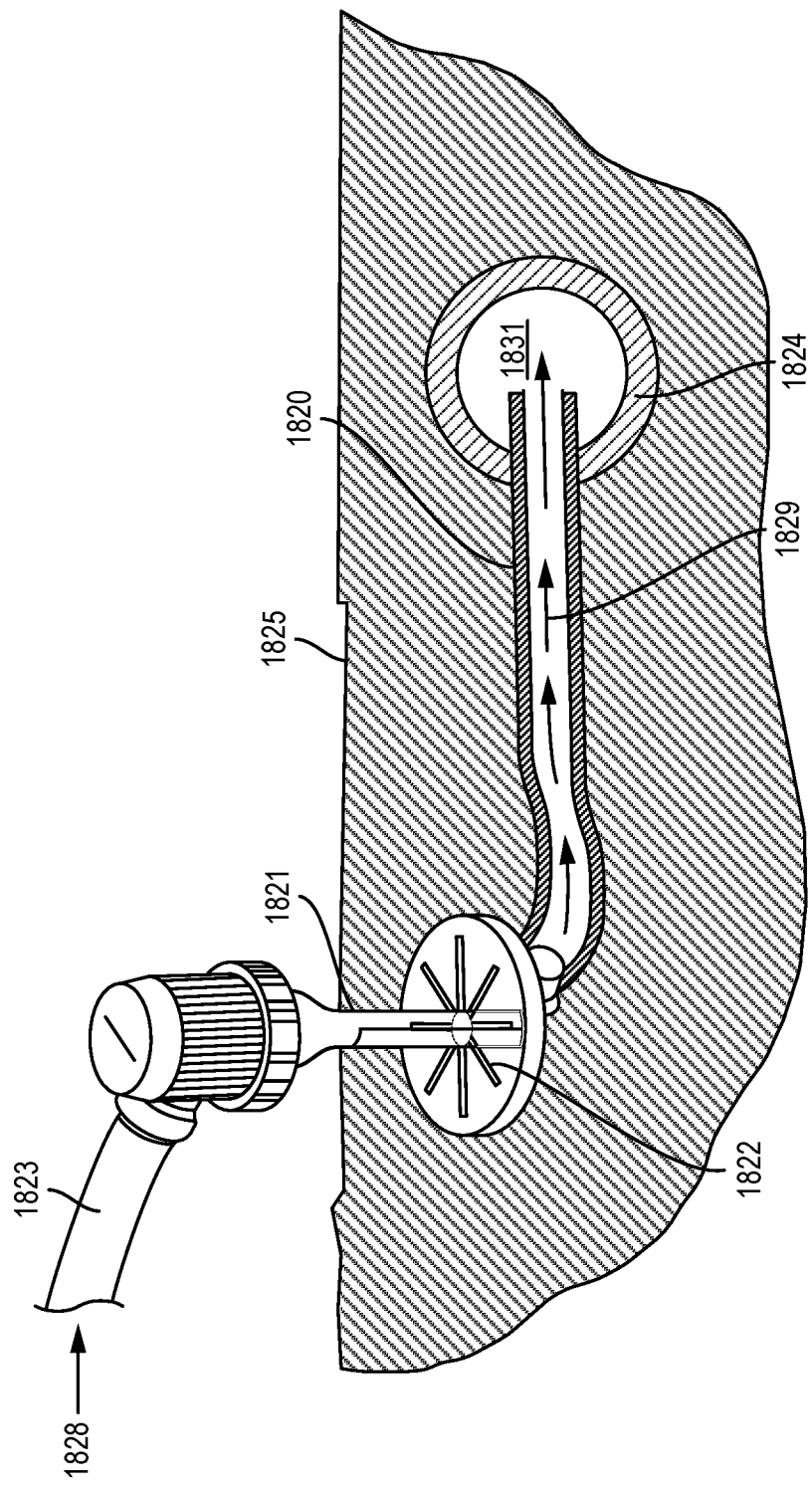

GRAFT-PORT HEMODIALYSIS SYSTEMS, DEVICES, AND METHODS

CROSS-REFERENCES TO RELATED APPLICATIONS

This application is a continuation of U.S. patent application Ser. No. 15/179,688, filed on Jun. 10, 2016, which claims the benefit of U.S. Provisional Application No. 62/174,384, filed on Jun. 11, 2015, which are incorporated herein by reference in their entirety for all purposes.

BACKGROUND OF THE INVENTION

The present invention relates generally to the design and use of medical devices, and more particularly to the design and use of implantable graft-port systems, devices and methods for establishing access to a fluid-filled internal body space of a patient including the patient's vascular system for blood treatments. In general, these blood treatments include, but are not limited to, hemodialysis, hemofiltration, hemodiafiltration, plasmapheresis, ultrafiltration, aquapheresis, n lipid pheresis and hemoperfusion. In the following description, the term "hemodialysis" (or "HD") is generally used in connection with the present invention, but it is not intended to restrict the use of the device and methods of the present invention to hemodialysis. The subject invention may be used for other blood treatments, drug infusions, or any procedures that require access to a fluid-filled internal body space of a patient, for example. Lock solutions to prevent fowling and infection are also disclosed.

Access to a patient's vascular system can be established by a variety of temporary and permanent devices implanted under the patients skin. Temporary access can be provided by the direct percutaneous introduction of a needle through the patient's integument and into a blood vessel. While such a direct approach is relatively simple and suitable for some applications, such as intravenous feeding, intravenous drug delivery, and other applications which are limited in time, they are not suitable for hemodialysis, chemotherapy, and extracorporeal procedures that must be repeated periodically, sometimes for the duration of the patient's life. Hemodialysis and hemofiltration (also referred to as hemofiltration), both rely on separate draw and return catheters implanted in a vein and/or artery to allow extra corporeal treatment of the blood. Peritoneal dialysis, in contrast, relies on a single catheter implanted in the peritoneum to permit introduction and withdrawal of dialysate to permit in situ dialysis.

In 2012, the number of patients treated for end stage renal disease (ESRD) was estimated to be about 3 million. Of these patients, about 2.8 million were undergoing dialysis treatment. Medicare spends about $8 billion in dialysis procedures annually. Despite the significant costs, about 20% of dialysis patients in the United States die each year, most often from heart disease or infections. Dialysis treatment of individuals suffering from renal failure requires that blood be withdrawn and cycled through a dialysis machine that performs the function of the failed kidneys. Hemodialysis must be repeated at regular intervals and thus requires repeated punctures using dialysis needles. These relatively large gauge needles are required to promote the high flow rates required during dialysis. Frequent puncturing of autogenous arteriovenous access as well as prosthetic arteriovenous access with large bore needles can cause trauma, conduit degeneration, hematoma formation, pseudoaneurysm formation, loss of patency, or even hemorrhage and exsanguination.

Implanted Ports:

For hemodialysis and other extracorporeal treatment regimens, a variety of implantable ports have been proposed throughout recent decades. Typically, the port includes a chamber and an access region, such as a septum, where the chamber is attached to an implanted catheter which, in turn, is secured to a blood vessel. In the case of veins, the catheter is typically indwelling and in the case of arteries, the catheter may be attached by conventional anastomosis. These access methods permit only limited flow rates which can be problematic since they prolong the duration of the treatment (i.e. hemodialysis, hemofiltration, plasmaphoresis, apheresis). Moreover, limited flow rates may cause catheter blockages or plugging resulting from fibrin sheath or thrombosis formation over the distal end of the catheter.

Vasca and Biolink were familiar companies founded in the mid-1990s that lead the development of totally implantable HD ports based on the notion that prior implanted ports demonstrated low infection and thrombosis as compared to catheters used for chemotherapy applications. These companies surmised that the experiences learned from chemotherapy catheters could be replicated with HD ports. However, infection was an early problem, and thrombosis complications were only marginally better when compared with HD catheter infection rates. Unexpected problems occurred relating to large needle size, increased frequency of needle puncture and the necessary high blood flow rates, which imposed harsher conditions for hemodialysis access than those encountered during chemotherapy. Vasca and Biolink left the business by 2006 after considerable effort.

Vasca's port was named LifeSite® (FIG. 1). Vasca obtained U.S. approval for commercial distribution of LifeSite® and sold the product for approximately 5 years between about 2000 and 2005. LifeSite® was found to induce complications in patients, including surgical site infections and needle puncture site infections, which were aggravated by poor tissue healing around the needle puncture site. Use of the buttonhole (or "BH") needle guidance technique in conjunction with LifeSite® was a factor in several infection episodes, in spite of various prophylactic measures (Ross, John J., et al., "Infections Associated with Use of the LifeSite® Hemodialysis Access System" *Clinical Infectious Diseases* 2002, 35:93-95). Misalignment of the buttonhole-type needle tract with the port's entrance resulted in failures to access correctly. Several factors may have contributed to poor performance, including:
 (a) large needle size (i.e. 14 gauge) and poor closure of the needle tract after needle withdrawal;
 (b) poor subcutaneous tissue healing and infection of the tissue around the needle tract;
 (c) length of the needle tract in subcutaneous tissue, with the perpendicular, protruding needle exiting from patient's skin, susceptible to inadvertent bumping and/or tearing of tissue and dislodgement;
 (d) the size and orientation of the implanted LifeSite® created high tensile stress in the tissue acting on the BH tract, which tended to open the BH tract;
 (e) sealing/locking of the docked needle within the port was not reliable, and could be compromised by forces acting on the protruding needle, resulting in blood leakage during the HD treatment;
 (f) in vivo shifting of the port relative to the BH tract caused misalignment of the port relative to the BH, so that needles were guided away from the port entrance, creating difficulty in accessing the blood and/or causing missed dialysis sessions;

(g) antimicrobial prophylaxis was not "locked" within the luminal passages of the port during the quiescent period, so microbes entering the catheter would not be exposed to a biocide; and (h) the LifeSite® design was subject to "single fault" failure caused by needle dislodgement.

Biolink's port product was called Dialock® (FIG. 2). Dialock® was evaluated in a pilot clinical trial starting in 1996 and infections occurred quickly. It was realized that tissue infections from needle punctures could be reduced by injecting an antimicrobial "lock" solution into the tissue encapsulating the implanted port. However, serious tissue healing complications, caused by frequent puncturing with large needles, and the difficulty of establishing blood access remained a problem. These and other deficiencies in Dialock® performance would ultimately limit adoption of this port. Biolink Corporation declared bankruptcy around 2004.

One problem with the Dialock® device is that the entry ports are usually inclined at a substantial angle relative to the skin surface through which the access tube (i.e. needle or trocar) is introduced. Such angled access requires that the health care professional introducing the access tube guess the angle and estimate the optimum insertion point on the patient's skin. This uncertainty in the device penetration is perhaps why this type of design necessitates the use of an enlarged "funnel" for receiving and aligning the access tube as it is introduced. It would thus be advantageous to provide access ports having entry passages which are disposed generally "vertically" (i.e. at an angle which is substantially normal to the skin surface through which the access tube is being introduced). By penetrating the access tube "straight in", it is much easier to align the access tube with the target opening. In this manner, the size of the orifice area can be reduced and the potential for skin damage can be minimized.

Implantable ports typically include a needle-penetrable septum which permits the percutaneous penetration of a needle or trocar into the internal chamber. The chamber, in turn, is connected to one end of the catheter, and the other end of the catheter is indwelling in the blood vessel. While workable, such designs suffer from a number of problems. Repeated penetration of the septum often leads to degradation over time, presenting a substantial risk of small particulates entering the blood stream. The implanted port may also require periodic replacement. Second, the passage of blood through the chamber or plenum will often encounter regions of turbulence or low flow, either of which can degrade the quality of blood over time and add to the time it takes to complete the patient's treatment regime.

Historically, attempts to solve these problems have included internal valve structures which isolate the interior of the port from the lumen of the implanted catheter when the port is not in use. Such valve-enabled ports, however, have their own shortcomings. For example, self-penetrating needles often cannot be used since they will be damaged by and/or cause damage to the port. In such instances, it is frequently necessary to use a catheter combined with a removable stylet, which is both more costly and more inconvenient than use of a simple needle. Moreover, many valved ports have no means or mechanism to assure that the valve is fully opened, particularly when insertion of the access needle opens the valve. Partial insertion of the needle can result in partial opening of the valve which can include a series of deleterious events.

A number of specific valve types have been incorporated into access port designs, including articulating valves such as leaflet valves, ball valves, and flapper valves. All such structures generally require that the access device be passed through the valve itself (i.e. the portion which closes the blood flow path through the valve) in order to cause the valve to open. Such a requirement presents the risk that the valve will be degraded by direct contact with the access device after repeated uses so that portions of the valve may be degraded and released into circulation. Such valves also represent significant risk of failure after repeated use or contact with a sharpened needle. Additionally, such valve structures can damage the access device as it is being introduced there through, thus potentially disrupting valve flow.

Many types of needle-actuated valved ports have been described over the years. Some ports include a duckbill valve which is opened by an elastomeric plug which is elongated by insertion of a needle. So long as the needle is fully inserted, the valve will be fully opened. It would be possible, however, to only partially insert the needle, resulting in only partial opening of the duckbill valve. Such partial opening could significantly degrade and alter the valve performance. Other needle-activated ports include locking mechanisms such as pinch clamps, displaceable balls and other elaborate features that increase the overall size of the port device. Large, bulky implanted ports can be obtrusive and uncomfortable for the patient when implanted. Furthermore, the geometry of some ports, particularly at the needle insertion point, may stretch the skin of the patient increasing the possibility of tearing and subsequent infection.

For these reasons, it would be desirable to provide improved valved implantable access ports for percutaneously accessing a patient's blood vessels, including both arteries and veins. The access ports will comprise a valve structure for isolating the port from an associated implanted catheter when the port is not in use. The valve will preferably provide little or no structure within the blood flow lumen of the access port and will even more preferably not require passage of an access tube, trocar or the like through the seating portion of a valve in order to open the valve. Furthermore, the port structure including the valve elements therein will have a substantially uniform cross-sectional area and will present no significant constrictions or enlargements to disturb or impede fluid flow there through. The port designs will permit percutaneous access using a conventional needle (i.e., fistula needle or standard trocar) or a proprietary needle without damaging the port or the needle. Still more preferably, the ports will include means for keeping the valve structures open in response to insertion of the needle or other access device without the needle becoming dislodged before the treatment is concluded. It would also be advantageous to provide increased flow rates without increasing the diameter of the catheter to reduce treatment time and thus improve the quality of life for the patient. Ports and valves according to the present invention will meet at least some of these objectives.

Information related to attempts to address these problems can be found in U.S. Pat. Nos. 3,998,222; 4,108,173; 4,181,132; 4,496,343; 4,534,759; 4,569,675; 4,778,452; 4,983,162; 5,053,013; 5,057,084; 5,120,313; 5,180,365; 5,226,879; 5,281,199; 5,263,930; 5,350,360; 5,417,656; 5,421,814; 5,476,451; 5,503,630; 5,520,643; 5,527,277; 5,527,278; 5,562,617; 5,637,088; 5,702,363; 5,704,915; 5,741,228; 5,755,780; 5,954,691; 5,989,239; 6,007,516; 6,022,335; 6,261,257; 6,582,409; 7,056,316; 7,131,192; 7,473,240; 7,803,143; 7,806,122; 8,151,801; 8,348,909 and U.S.

Patent Application Publication Numbers 2007/0265584; 2011/0264104; 2014/0018721; 2014/0024998; 2014/0128792 as well as European Patent Application Numbers: EP 1550479; EP 2686033; EP 2300071 and International Patent Application Numbers: WO 95/19200; WO 96/31246; WO 97/047338; WO 98/35710; WO 99/38438; WO 07/061787; WO 09/152488; WO 10/015001; and WO 12/125927, for example.

Lock Solutions:

The need to leave catheters implanted for a prolonged period raises a number of concerns. First, the catheters can become infected requiring treatment of the patient and often requires removal of the catheter. This is a particular problem with transcutaneous catheters where the skin penetration is a common route of infection. Urinary catheterization exposes patients to increased risk of urinary, kidney and blood (sepsis) infections. Some other catheter-related infectious complications include septic shock, endocarditis, septic arthritis, osteomyelitis and epidural abscess. Biofilms of infectious bacteria and yeasts often colonize indwelling catheters. Second, implanted catheters can often become plugged or fouled over time. Catheter malfunction is often due to extrinsic and/or intrinsic thrombosis, and has been found to be the most common indication for catheter removal. This is a particular problem with intravascular catheters where clotting and intrinsic thrombus formation (i.e. within the catheter lumen) can be problematic. Extrinsic thrombosis, including central venous thrombosis, is also an important and common complication.

To reduce problems associated with thrombus formation, it is now common to "lock" intravascular access catheters between successive uses. Locking typically involves first flushing the catheter with saline to remove blood, medications, cellular debris and other substances from the catheter lumen. After the catheter has been flushed, a locking solution, typically heparin, is then injected to displace the saline and fill the lumen. The heparin locking solution both excludes blood from the lumen and actively inhibits clotting and thrombus formation within the lumen. To address infection, various antimicrobial substances have been combined with the locking solution in order to inhibit infection at the same time that thrombosis is being inhibited. However, problems with current and continuously emerging resistance to antimicrobial substances, as well as the over-use (and hence the increased risk of developing resistance) of antimicrobials, is an ever-growing concern.

While generally effective, the use of heparin locks suffers from a number of problems and disadvantages. For example, some thrombi may still form at the distal tip of the catheter despite the use of heparin. The need to prepare a heparin solution at the end of every catheter treatment session is time-consuming and presents an opportunity for error by a caregiver. Additionally, heparin has been shown to stimulate biofilm formation which makes it necessary to combine an antimicrobial compound in the heparin lock solution. Heparin is also associated with potentially adverse effects, including heparin-induced thrombocytopenia and bleeding risks.

Various acids have been proposed for use as antimicrobial catheter lock solutions. However, high concentrations of these acids have been shown to cause hemolysis of red blood cells and other harmful effects. Citrate, an ionic form of citric acid, will chelate the divalent cations including the calcium ions in blood and tissue. Serious symptoms have been reported when the ionized calcium blood level decreases. Spillage of extra locking solution into the patient includes miscalculating the lock volume, multiple instillations of solution into the same lumen and even deliberate over injection of solution to clear an occluded catheter. Thus, there is legitimate concern that risks of using concentrated sodium citrate for a catheter lock are not well understood.

Therefore, it would also be desirable to provide improved catheter lock solutions and locking methods to inhibit fouling of the catheter lumen and/or reduce the chance of infection, preferably both. In particular, such methods should be cidal against a broad spectrum of microorganisms and discourage the development of resistant microbes without damaging blood and/or tissue cells. The lock should be relatively inexpensive, non-toxic, easy to store, compatible with the catheter and port materials, safe if inadvertently infused systemically, easy to implement, require minimum or no preparation, and be useful with most or all types of implanted catheters, including hemodialysis and hemofiltration catheters, IV catheters, peritoneal dialysis catheters, urinary catheters, chemotherapy catheters, and the like. At least some of these objectives will be met by the invention described hereinafter.

Information related to attempts to address these problems can be found in U.S. Pat. Nos. 4,114,325; 4,929,242; 5,077,281; 6,635,243; 6,423,706; 6,679,870; 6,685,694; 6,824,532; 6,958,049 and U.S. Patent Application Publication Numbers: 2003/0175323; 2005/0037048; 2005/0043673; 2005/0181008; 2006/0024360; 2006/0052757; 2006/0062850; 2006/0094690; 2006/0177477; 2006/0253063; 2006/0257390; 2007/0292355; 2008/0118544; 2010/0249747 and 2011/0311602 as well as International Patent Application Number: WO 2000/01391, for example. Citrate has been discussed as a locking solution in various concentrations or in combination with other compounds in numerous publications including, for example, Ash et al., *ASAIO Journal*, (2000) 46(2):222; Mandolfo et al., *Journal of Vascular Access*, (2006) 7(3):99-102; Dogra et al., *Journal of the American Society of Nephrology*, (2002) 13(8):2133-2139; and Meeus et al., *Blood Purification* (2005) 23(2): 101-105.

Various graft-port devices, methods for establishing access to a vascular system, and lock solutions, including some embodiments of the invention, can mitigate or reduce the effect of, or even take advantage of, some or all of these potential problems.

For the foregoing reasons, there is a legitimate need for effective and efficient ways to provide subcutaneously-implantable graft-port systems, devices and methods for establishing access to a vascular system of a patient that requires periodic ongoing extracorporeal blood treatment.

It would be desirable to leverage the advantages of a graft access while maintaining an easy-to-use port interface in order to decrease miscannulation and promote intra-session hemostasis. It would be particularly beneficial to also provide a graft-port systems, devices and methods for establishing vascular access to a patient to facilitate some or all of the following: 1) reduce the overall size of the implanted port; 2) simplify the locking mechanism to reduce the form factor of the port; 3) reduce the risk of foreign contaminants from invading the port; 4) decrease the incidence of bacteremia and sepsis; 5) simplify the surgical implantation and use of the device for health care professionals; 6) reduce the cross-sectional needle sealing area; 7) enhance overall safety via secure connections; 8) increase the quality of life and reduce treatment pain for the patient; 9) increase blood flow through the device during use; and 10) provide a lock solution to prevent fowling and infection. These attributes would increase treatment efficiency and improve the longevity and quality of life for the patient.

BRIEF SUMMARY OF THE INVENTION

Certain embodiments of the invention relate to the design and use of implantable graft-port systems, devices and methods for establishing access to a fluid-filled internal body space of a patient including accessing the patient's vascular system to receive blood treatments. More specifically, some embodiments of the present invention satisfy the need of providing graft-port systems, devices and methods for establishing vascular access while reducing the overall size of the implanted port, simplifying the locking mechanism to reduce the form factor of the port, reducing the risk of foreign contaminants from invading the port, decreasing the incidence of bacteremia and sepsis, simplifying the surgical implantation and use of the device for health care professionals, reducing the cross-sectional needle sealing area, enhancing overall safety via secure connections, increasing the quality of life and reducing treatment pain for the patient, increasing blood flow through the device during use.

In accord with a first embodiment, an implantable port device for establishing access to a blood vessel of a patient comprises a tapered seat configured to receive a tip of an access tube. The seat has a proximal portion, a distal portion, and a conical surface disposed between the proximal portion and the distal portion. A guide is configured to engage the tip of the access tube and assist in directing the tip of the access tube toward the seat. An interface surface is configured to engage the blood vessel of the patient or a vascular access catheter. The interface surface has an aperture in fluid communication with the distal end of the seat. The conical surface includes a taper angle having a value within a range from about 0.5 degrees to about 4.0 degrees. The proximal portion of the seat is configured to receive the tip of the access tube.

In other embodiments, the conical surface includes a taper angle having a value within a range from about 2.5 degrees to about 3.5 degrees and the conical surface of the tapered seat includes a taper of about 3.3 degrees from the proximal portion to the distal portion. The distance between the proximal portion and the distal portion of the tapered seat is between about 1.0 mm and 5.0 mm. Preferably, the distance between the proximal portion and the distal portion of the tapered seat is between about 1.5 mm and 2.5 mm. The tapered seat creates a mismatch fit with a diameter of the access tube when the tapered seat receives the access tube in use. The mismatch fit creates a decrease in the cross-sectional sealing area, a reduction in the overall device size, and an increase in blood flow during treatment. The tapered seat creates a match fit with a diameter of the access tube when the tapered seat receives the access tube in use. The match fit conducive to performing procedures requiring flow rates less than normal physiological pressures. The tapered seat creates a mismatch fit with a diameter of the access tube when the tapered seat receives the access tube in use. The mismatch fit conducive to performing procedures requiring flow rates greater than normal physiological pressures.

The guide includes at least one ridge elevated from a flat surface and the at least one ridge is configured in a spiral pattern, a ray pattern, or a cross pattern with each pattern terminating adjacent the proximal portion of the tapered seat. The device is a single molded device produced using an injection molding process such that turbulence of a vascular blood flow is minimized during use. A single molded configuration may be machined or molded and has no seams or parts than require adhesive or fastening, for example.

The device may include a stabilizer base that is reversibly attached to the device to increase the footprint of the device when implanted and reduce movement during use. The stabilizer base includes at least one suture ring to suture (i.e. attach) the device to the patient. Optionally, the device includes a silicon wafer valve disposed near the distal portion of the tapered seat. The device does not require a valve.

Another embodiment provides a subcutaneously implanted graft-port device used to establish access to a blood vessel of a patient that requires repeated vascular access over a period of time. The device comprises a housing having an inlet opening, an outlet opening and an interior conduit defined therein between. The conduit is configured to accept a vascular blood flow and the housing includes a flat surface. The flat surface is oriented nearest to, and substantially parallel with, the patient's skin when the device is implanted subcutaneously. A guide is located on the flat surface. A tapered seat is located in the center of the flat surface. The tapered seat includes an outer perimeter, an inner perimeter smaller than the outer perimeter, and a conical surface extending between the outer and inner perimeters. The tapered seat includes a taper of between about 2.5 degrees to 3.5 degrees from the outer perimeter to the inner perimeter, the tapered seat configured to receive an access tube first through the outer perimeter. A valve mechanism is configured to seal the conduit closed to physiologic pressures while allowing the vascular blood flow until the valve is opened via percutaneous insertion of the access tube into the tapered seat by a health care professional (i.e. a physician, nurse, or medical technician). The valve allows continued vascular blood flow through the conduit and the flow is unobstructed by the access tube. The valve is closed when the access tube is removed from the tapered seat at the end of a treatment. The device is produced using an injection molding process so that turbulence of the vascular blood flow is minimized when the valve is open during use. The device includes a substantially uniform cross-sectional area so that turbulence of the vascular blood flow is minimized when the valve is open during use. The access tube is a trocar and the access tube is configured to accept a needle. The access tube locks in place within the tapered seat to prevent dislodgment of the access tube prior to a treatment conclusion. The lock is a snap-fit configuration. The access tube forms an angle of about 90 degrees relative to the flat surface when the access tube is locked in place. The access tube includes a swivel attachment configured to rotate 360 degrees about an axis. Furthermore, the treatment is selected from the group consisting of hemodialysis, hemofiltration, hemodiafiltration, plasmapheresis, ultrafiltration, aquapheresis, n lipid pheresis, chemotherapy, hemoperfusion, peritoneal dialysis, and pleural drainage. The tapered seat includes a taper of about 3.3 degrees from the outer perimeter to the inner perimeter. The distance between the outer perimeter and the inner perimeter of the tapered seat is between about 1.5 mm and 2.5 mm. The tapered seat creates a mismatch fit with a diameter of the access tube when the tapered seat receives the access tube in use. The mismatch fit creates a decrease in the cross-sectional sealing area, a reduction in the overall device size, and an increase in blood flow during treatment. An adaptor connects a catheter with the conduit.

In some embodiments, the guide includes at least one ridge, the ridge elevated from the flat surface. The guide is sized to engage a tip of the access tube, and the at least one ridge is configured and located to guide the tip of the access tube toward the tapered seat to assist the health care professional in percutaneously directing the access tube into the tapered seat (to open the valve). The at least one ridge is configured in a spiral pattern, a ray pattern, or a cross pattern with each pattern terminating adjacent the outer perimeter of the tapered seat. The at least one ridge is configured in a target pattern with the outer perimeter of the tapered seat located nearest the center of the target pattern. The device includes a transparent material and the guide includes LED lights and a receiver coil for receiving an electrical current. The lights are configured to illuminate when an electromagnetic induction chip is placed external to the patient and substantially above the subcutaneously implanted device. The induction chip producing a voltage in the receiver coil. The voltage powering the lights so that a location of the subcutaneously implanted device is visually revealed to the health care professional.

In some embodiments, the valve mechanism includes a compressible elastic disc. The disc having a centrally located slit configured to open to an essentially elliptical shape when inward pressure is applied simultaneously to opposite sides of the disc. The elliptical shape is configured to elastically rebound to a closed slit position when the application of inward pressure is removed. The valve mechanism includes at least one spherical element and the at least one spherical element includes a slot extending at least partially around a circumference of the spherical element. The device further comprises a retainer element and/or a silicon spring assembly. The device includes a stabilizer removably attached to the device. The stabilizer is configured to increase the footprint of the device and reduce movement of the device in use. The stabilizer may include suture rings, tabs, pocket over molds, wires and/or anchors. The wires may be magnesium wires with a diameter of about 2 mm. The movement may include linear motion and/or rotational motion. The stabilizer is made of a bioresorbable material, a bioabsorbable material or a biodegradable material. The bioresorbable material includes polylactide (PLA), polycaprolactone (PCL), polydioxanone (PDX), poly(L-glutamate), poly(L-lysine), or poly(L-leucine).

In more embodiments, the device further includes an implantable catheter fluidly connected to the device and adapted to deliver a therapeutic substance from the device to the blood vessel of the patient when the access tube is inserted into the tapered seat. At least a portion of the implanted catheter is sufficiently porous so as to permit diffusion of the therapeutic substance outward from a lumen of the catheter to an outer surface of the catheter and into the blood vessel surrounding the catheter to inhibit infection. The device includes a vortex clamp removably attached to the device and configured to modify the vascular blood flow through the conduit when the valve is open. The modified vascular blood flow creates a reduction in turbulence.

In yet another embodiment, the device includes a double port configuration. The double port configuration includes two ports fused together. The subcutaneously implanted graft-port device is a single molded configuration or a press fit configuration.

Another embodiment of the invention provides a method for establishing access to a blood vessel of a patient that requires repeated vascular access over a period of time. The method comprises subcutaneously implanting a graft-port device. The device comprises a housing having an inlet opening, an outlet opening and an interior conduit defined therein between. The conduit is configured to accept a vascular blood flow. The housing includes a flat surface oriented nearest to and substantially parallel with a skin of the patient when the device is subcutaneously implanted. The device also comprises a guide located on the flat surface and a tapered seat located in the center of the flat surface. The tapered seat includes and outer perimeter, an inner perimeter smaller than the outer perimeter, and a conical surface extending between the outer and inner perimeters. The tapered seat includes a taper of between about 0.5 degrees to 4.0 degrees from the outer perimeter to the inner perimeter configured to receive an access tube first through the outer perimeter. A valve mechanism is configured to seal the conduit closed to physiologic pressures while allowing the vascular blood flow through the conduit. The access tube is inserted through the skin (i.e. percutaneous) into the tapered seat of the device to open the valve and allow continued vascular blood flow through the conduit. The flow is not obstructed by the access tube. The access tube is removed from the tapered needle seat of the device to close the valve at a treatment conclusion. The tapered seat includes a taper of between about 2.5 degrees to 3.5 degrees from the outer perimeter to the inner perimeter. The access tube does not pass into the conduit or impede the vascular blood flow when the valve is open. Furthermore, locking the access tube in place within the tapered seat prevents dislodgment of the access tube prior to the treatment conclusion. The treatment is selected from the group consisting of hemodialysis, hemofiltration, hemodiafiltration, plasmapheresis, ultrafiltration, aquapheresis, n lipid pheresis, chemotherapy and hemoperfusion.

In some embodiments, the guide includes at least one ridge elevated from the flat surface. Engaging a tip of the access tube with the at least one ridge guides the tip of the access tube toward the tapered seat assists in percutaneously directing the access tube into the tapered seat. The at least one ridge is a spiral pattern, a ray pattern, or a cross pattern with each pattern terminating adjacent an outer perimeter of the tapered seat.

In some embodiments, the device includes a transparent material and the guide includes LED lights and a receiver coil for receiving an electrical current. Placing an electromagnetic induction chip external to the patient and substantially above the subcutaneously implanted device induces a voltage in the receiver coil. The voltage powers the lights to visually reveal a location of the subcutaneously implanted device to a health care professional. In this manner, the lights are visible to the physician through the skin to reveal the location of the port just under the patient's skin. A stabilizer base may be separately attached to the housing.

In another embodiment of the invention, a subcutaneously implanted graft-port device is used to treat a patient by establishing access to a vascular blood flow of a patient that requires repeated vascular access over a period of time. The device comprises a housing having an a distal end and a proximal end. The proximal end has a flat (plateau-like) surface oriented nearest to and substantially parallel with a patient's skin when the device is subcutaneously implanted. A guide is located on the flat surface. A tapered seat is located in the center of the flat surface and includes and outer perimeter, an inner perimeter smaller than the outer perimeter, and a conical surface extending between the outer and inner perimeters. The tapered seat includes a taper of between about 0.5 degrees to 4.0 degrees from the outer perimeter to the inner perimeter. A stabilizer base is separately attachable to the distal end of the housing and configured to completely encircle an exterior of a tubular structure containing the vascular blood flow therein. The tubular structure is located between the distal end of the housing and the stabilizer base when the stabilizer base is attached to the housing. An access tube is insertable into the outer perimeter of the tapered seat to allow access to the vascular blood flow. The blood flow is unobstructed by the access tube. The treatment is concluded upon removal of the access tube from the tapered seat.

In some embodiments, a valve seals the device (closed) until the valve is opened via percutaneous insertion of the access tube into the tapered seat. The valve is a silicon wafer valve located between the inner diameter of the tapered seat and the exterior of the tubular structure. The stabilizer base is attached to the distal end of the housing with a clamping mechanism. The valve includes a silicon wafer pierceable by the access tube. The tubular structure is a native blood vessel or a synthetic tube having two opposing ends. One end of the synthetic tube is grafted onto a native artery and the other end of the synthetic tube is grafted onto a native vein. The stabilizer base includes at least two suture rings to secure the graft-port device in place when subcutaneously implanted.

In another embodiment of the invention, a subcutaneously implanted single molded graft-port device is used to establish access to a blood vessel of a patient when the patient requires repeated vascular access over a period of time. The device comprises a housing having an inlet opening, an outlet opening and an interior conduit defined therein between, the conduit configured to accept a vascular blood flow. The housing includes two flat surfaces, the flat surfaces each oriented nearest to and substantially parallel with a skin of the patient when the device is subcutaneously implanted. A guide is located on each of the two flat surfaces. A tapered seat is located in the center of each flat surface. The tapered seats includes an outer perimeter, an inner perimeter smaller than the outer perimeter, and a conical surface extending between the outer and inner perimeters. Each of the tapered seats includes a taper of between about 0.5 degrees to 4.0 degrees from the outer perimeter to the inner perimeter. The tapered seats are each configured to receive an access tube through the outer perimeter. The device is connectable to one double-lumen catheter or two single-lumen catheters to establish access to the patients blood vessel.

In accord with another embodiment, a subcutaneously implanted single molded graft-port device is used to establish access to a blood vessel of a patient requiring repeated vascular access over a period of time. A single molded configuration may be machined or molded and has no seams or parts than require adhesive or fastening, for example. The device comprises a housing having three flat surfaces. The flat surfaces are each oriented nearest to and substantially parallel with the patient's skin when the device is subcutaneously implanted. An inlet opening, an outlet opening and an interior conduit defined therein between each opening corresponds to each flat surface and each is configured to accept a vascular blood flow. A guide is located on each of the three flat surfaces. A tapered seat is located in the center of each flat surface. The tapered seats include and outer perimeter, an inner perimeter smaller than the outer perimeter, and a conical surface extending between the outer and inner perimeters. Each of the tapered seats includes a taper of between about 0.5 degrees to 4.0 degrees from the outer perimeter to the inner perimeter and each tapered seat is configured to receive an access tube through the outer perimeter.

In accord with another embodiment, a method for using a hydrophobic antimicrobial solution for inhibiting infection and preventing blood clot formation to safely and effectively lock an implanted port device is disclosed. The port device is open to a body lumen of a patient and the method of using the solution comprises combining a tocopherol compound with ricinoleic acid and at least one of the following saturated mid-chain fatty acid(s): octanoic acid; and/or decanoic acid; and/or dodecanoic acid. The solution is placed inside the implanted port device. The combination of the tocopherol, ricinoleic acid and the at least one of the mid-chain fatty acid(s) provide a viscosity to the solution to safely and effectively lock the implanted port device by inhibiting the solution from running out of the port device into the body lumen of the patient when the solution is inside the port device while allowing the solution to seep out of a catheter attached to the port device. The catheter has a sufficient porosity to permit diffusion of the solution outward from the catheter into a tissue or a bloodstream surrounding the catheter to inhibit infection. To improve the aroma of the lock solution, this method may further comprise mixing at least one essential oil with a fatty alcohol corresponding to at least one saturated mid-chain fatty acid.

In another embodiment, an anti-inflammatory analgesic solution is configured for inhibiting infection and preventing blood clot formation to safely and effectively lock a port device. The port device is implanted in a patient and open to a body lumen of the patient. The solution comprises a tocopherol compound combined with ricinoleic acid and one or more of the following mid-chain fatty acid(s): 1) octanoic acid (in an amount not to exceed more than about 50% by volume/volume); 2) decanoic acid (in an amount not to exceed more than about 25%, by volume/volume); and 3) dodecanoic acid (in an amount not to exceed more than about 25% by weight/volume). The solution is configured to be injected into the port device and the combination of the tocopherol, ricinoleic acid and one or more of the mid-chain fatty acid(s) provide a total viscosity to the solution greater than about 3 mPa·s so as to safely and effectively lock the port device and reduce inflammation. The solution is configured to physiologically lubricate a valve of the port device when injected.

In another embodiment, a method for establishing access to a blood vessel of a patient requiring repeated vascular access over a period of time is disclosed. The method comprises subcutaneously implanting a graft-port device. The device comprises a housing having an inlet opening, an outlet opening and an interior conduit defined therein between. The conduit configured to accept a vascular blood flow. The housing includes a flat surface and the flat surface is oriented nearest to and substantially parallel with the patient's skin when the device is subcutaneously implanted. A guide is located on the flat surface. A tapered seat is located in the center of the flat surface. The tapered seat includes and outer perimeter, an inner perimeter smaller than the outer perimeter, and a conical surface extending between the outer and inner perimeters. The tapered seat includes a taper of between about 0.5 degrees to 4.0 degrees from the outer perimeter to the inner perimeter. The tapered seat configured to receive an access tube first through the outer perimeter. A valve mechanism comprises a spring element, a conical piston, a washer, a cup element, a first spherical element and a second spherical element. The second spherical element has a smaller diameter than the first spherical element and the first spherical element has a recessed area configured to receive a portion of the second spherical element and a slot running along a diameter located substantially opposite the recessed area. A needle is percutaneouly inserted into the tapered seat of the device wherein the needle contacts the slot at a first position and rotates the first spherical element about 90 degress along an axis to open the valve in a second position. The access tube is removed from the tapered needle seat of the device to close the valve at a treatment conclusion. The second spherical element simultaneously rotates within the recessed portion as the first spherical element is rotated. The second spherical element transmits a compression force toward the conical portion when the valve is open. Removal of the needle relieves the force and the first spherical element rotatatably rebounds to the first position to close the valve. The slot is substantially horizontal in the first position and substantially vertical in the second position. The washer is compressed into the cup element when the valve is open.

These and other features, aspects, and advantages of various embodiments of the invention will become better understood with regard to the following description, appended claims, accompanying drawings, and abstract.

BRIEF DESCRIPTION OF THE DRAWINGS

FIGS. 9A-9I are top views of various guide configurations in accord with certain embodiments of the invention.

FIG. 10A is a side view of a slit valve mechanism according to an embodiment of the invention.

FIGS. 10B-10C are top views of slit valve mechanisms in accord with certain embodiments of the invention.

FIG. 10D illustrates a pre-assembly configuration of the slit valve mechanism of FIG. 10C according to an embodiment of the invention.

FIGS. 13C1-13C7 depict an insertion sequence of access tubes opening ports in accord with embodiments of the invention.

FIGS. 14D1-14D4 are perspective views of a slotted ball portion of a valve mechanism according to an embodiment of the invention.

FIG. 14E1 is a side cut-a-way view of the slotted ball of FIGS. 14D1-14D4 positioned in an implantable port device according to an embodiment of the invention.

FIGS. 14E2-14E5 are perspective views of a conical cup portion of a value mechanism according to an embodiment of the invention.

FIG. 14E6 is a top view of a valve mechanism according to an embodiment of the invention.

FIGS. 14G1-14G3 are perspective views of a slotted ball valve according to another embodiment of the invention.

FIGS. 18A-18C illustrate methods of locking and disinfecting an implanted catheter according to an embodiment of the invention.

DETAILED DESCRIPTION OF THE INVENTION

Figure 3:
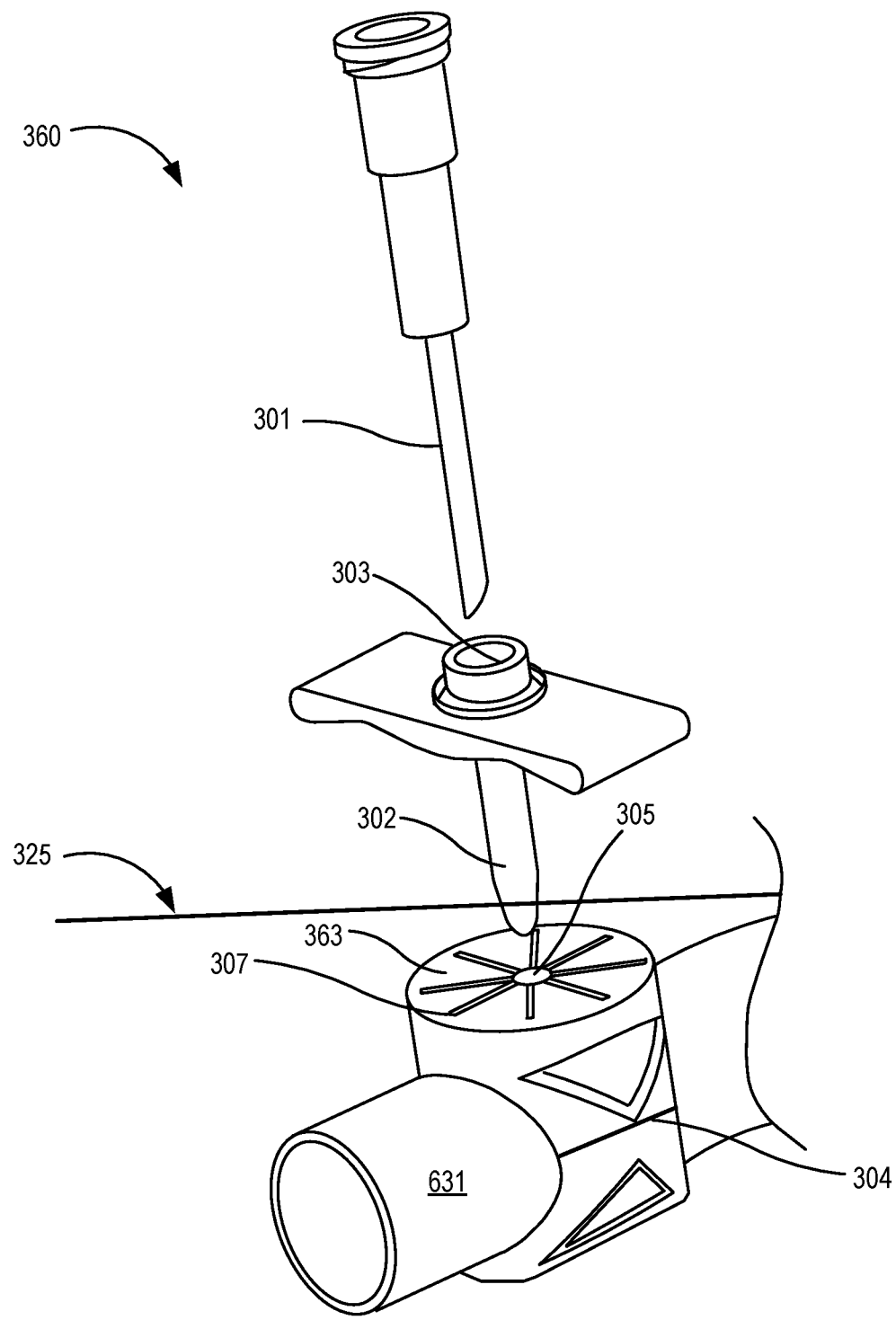
FIG. 3 is a partially exploded perspective view of an implantable port device according to an embodiment of the invention.

FIG. 3 shows an implantable port device for establishing direct or indirect access to a blood vessel of a patient. The device is implanted beneath the patient's skin surface 325 and includes a tapered seat (FIGS. 4-5) configured to receive a tip of an access tube (i.e. needle 301 or trocar 302), the seat has a proximal portion, a distal portion, and a conical surface disposed between the proximal portion and the distal portion. The access tube (i.e. needle 301 or trocar 302) is inserted in the center of the flat surface 363 and into the tapered seat. The flat surface 363 is generally parallel with the skin surface when subcutaneously implanted. The device provides a low profile to facilitate relatively shallow subcutaneous placement. Unlike the domed geometry of some prior art devices such as FIG. 1, the flat (plateau-like) surface eases skin tension to prevent stretching and/or tearing of the skin. Insertion of the access tube into the tapered seat opens the conduit to physiological pressure and continuous blood flow through the conduit. An opening 305 to the proximal portion is shown in FIG. 3. A guide 307 is configured to engage the tip of the access tube and to assist in directing the tip of the access tube toward the seat opening 305. The interface surface is configured to engage a tubular structure 631 (e.g. a native blood vessel, a vascular access catheter or a synthetic tube grafted to a blood vessel). The interface surface has an aperture in fluid communication with the distal end of the seat. The conical surface includes a taper angle having a value within a range from about 0.5 degrees to about 4.0 degrees (FIGS. 4-5). The proximal portion of the seat is configured to receive the tip of the access tube therethrough. In this embodiment, the device includes a hinge on one side and an opening on the opposite site so that the device is able to open in a manner similar to the way a clam shell opens and closes to surround the outside of the blood vessel or synthetic tube in the closed position as shown in FIG. 3. A latch, clip, snap or other similar securing apparatus 304 located opposite the hinge may be used to attach the device around the outside of the vessel wall. Extrinsic pressure maintains hemostasis. The device shown in FIG. 3 does not require a valve but may optionally include a valve mechanism, such as a silicon valve 510 as shown in FIG. 5 for example. If no valve is present, the device is sealed at the conclusion of treatment using the healing characteristics of the vessel wall.

Regardless of the presence or absence of the optional valve mechanism, the port devices shown in FIGS. 3 and 5 fit snugly around the external diameter of the native vessel or synthetic tube to compress the vessel and provide extrinsic pressure to maintain hemostasis. The vessel wall tension acts as a tamponade to close or block the wound left from the access tube after the tube is withdrawn. The tamponade promotes natural blood clotting and encourages intrinsic coagulation at the puncture site on the skin where the access tube penetrated. This prevents bleeding and promotes healing.

Alternatively, the vessel may be secured as shown in FIG. 5. In this embodiment, the device 564 has a stabilizer base 564b reversibly attached to the device to increase the footprint of the device when implanted. Two or more clips 508a, 508b may be used to fasten the top portion of the device 564a to the bottom stabilizer base 564b to securely fasten the device around a blood vessel 531. The bottom stabilizer base 564b may include one or more suture rings 509 to attach the subcutaneously implanted device in the patient's body. By fastening the device in this manner, the flat surface 563 of the device is maintained in an orientation essentially parallel with the skin when subcutaneously implanted. Attaching the device with sutures may also prevent movement, migration, or wobble when the access tube is inserted into the device.

Figure 4A:
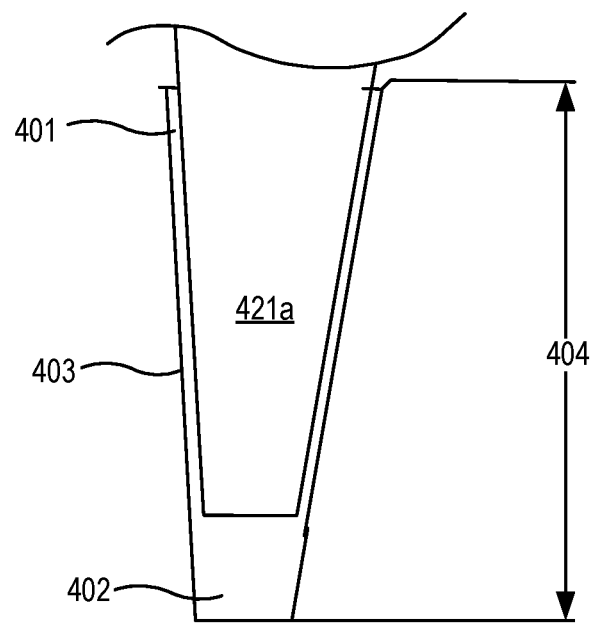
FIG. 4A is an illustration of the tapered seat with a match fit access tube according to an embodiment of the invention.
Figure 4B:
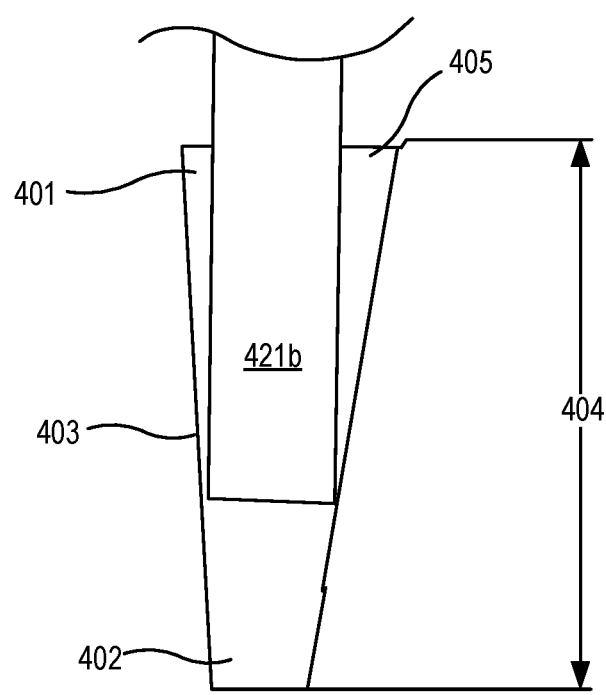
FIG. 4B is an illustration of the tapered seat with a mismatch fit access tube according to an embodiment of the invention.
Figure 5:
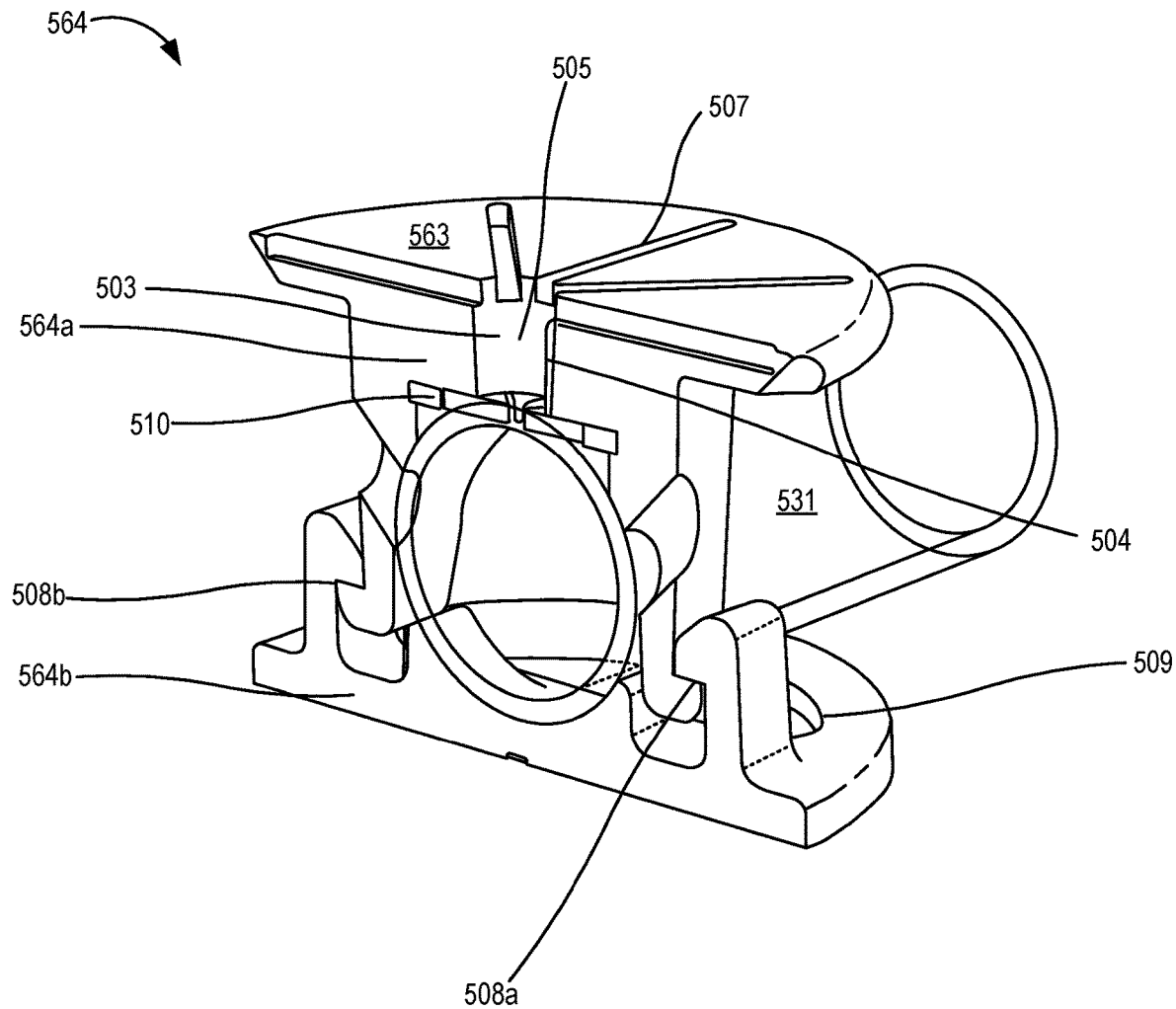
FIG. 5 is a cross sectional perspective view of an implantable port device according to an embodiment of the invention.

FIGS. 4A and 4B illustrate the taper of the tapered seat. The shape of the access tube and the tapered seat allow for a wide range of flow rates. The opening of the tapered seat 405 has a proximal portion 401 that is wider than the distal portion 402. The taper angle 403 of the conical surface between the proximal 401 and distal 402 portions is about 0.5 degrees to 4.0 degrees. Preferably, the taper angle 403 has a value within a range from about 2.5 degrees to about 3.5 degrees. These ranges can conveniently accommodate anything from a parallel-walled needle 421b with a very high gripping ceiling area fit to a leur tip connector which is about 4 degrees. Most preferably, the taper angle 403 is 3.3 degrees from the proximal 401 to the distal 402 portion. The distance 404 between the proximal portion 401 and the distal portion 402 is between about 1.0 mm and 5.0 mm. Preferably, the distance between the proximal 401 and distal 402 portions is between about 1.5 mm and 2.5 mm as this has been found to provide maximum dependability and functionality while minimizing the height of the device. The tapered seat creates a mismatch fit with a diameter of an access tube when tapered seat receives the access tube (FIG. 4B). The tapered seat creates a mismatch fit with a diameter of the access tube when the tapered seat receives the access tube. The mismatch fit is particularly conducive to performing procedures requiring relatively high pressure flow rates (e.g. flow rates greater than or above normal physiologic pressures) including the injection of contrast dyes or performing dialysis procedures, for example.

One advantage of the larger taper angle is that it allows a health care professional to begin to layer (i.e. flare) the needle more quickly. The flow rates received through the access tube depend (at least) on its internal liminal diameter or radius. Optimum flow rates are generally realized with a steeper taper.

Unlike the connections between an IV tube and a catheter or needle, a matching fit between an access tube (i.e. needle, trocar, removable cannula) and a port is novel (FIG. 4A). Creating a match fit (FIG. 4A) between the tapered seat and a diameter of the access tube is particularly conducive to performing procedures requiring relatively low pressure flow rates (e.g. flow rates less than or below normal physiologic pressures) including the administration of intravenous fluids, for example.

A matching or mismatching fit could be accomplished using an adaptor; however, changing the outside diameter of the access tube 421a, 421b placed into the taper seat would accomplish similar goals. It is contemplated that the access tube may be disposable (i.e. single use).

Figure 6:
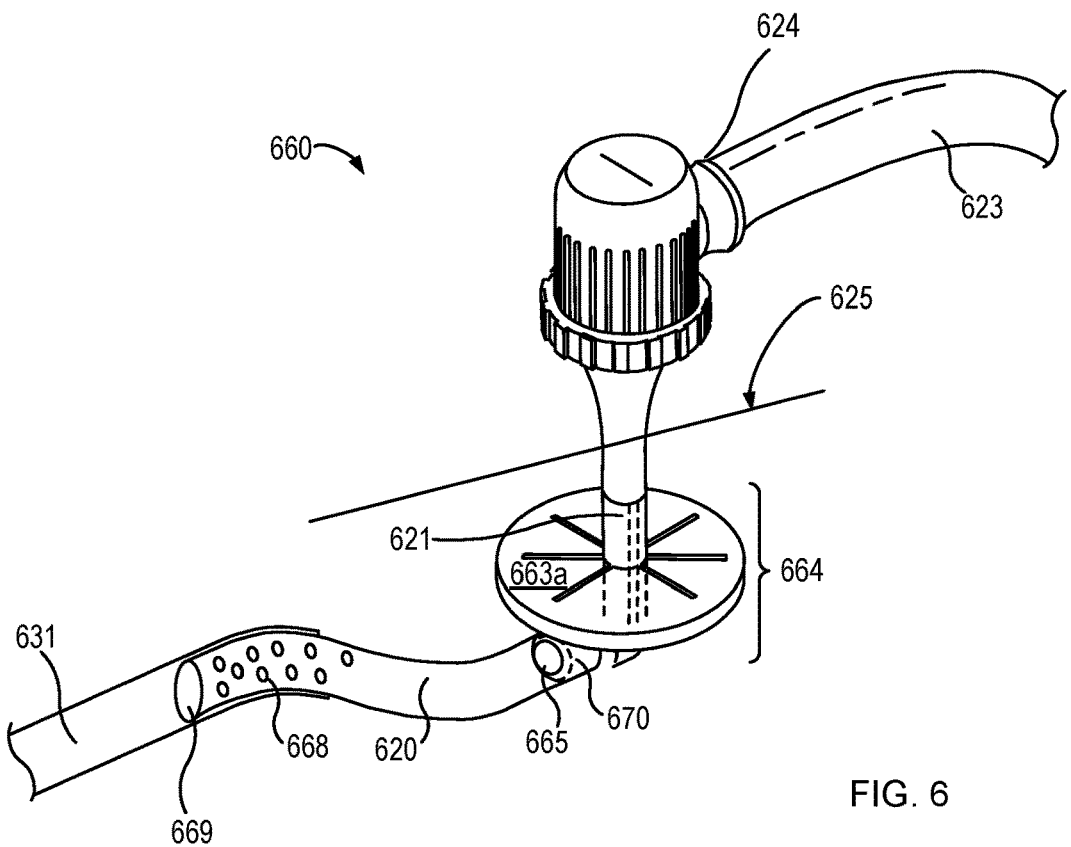
FIG. 6 is a perspective view of a graft-port system according to an embodiment of the invention.

FIG. 6 shows an embodiment of a single molded graft-port device 660 implanted below the skin surface 625. A connecting line 623 is attached to an access tube 621 (i.e. needle or trocar), with a swivel mechanism 624. The swivel mechanism 624 prevents the connecting line 623 from kinking or binding when the patient moves or otherwise changes position. In addition to allowing patient mobility, the swivel also prevents accidental decannulation. The access tube 621 is inserted in the center of the flat surface 663a and into the tapered seat. The flat surface 663a is generally parallel with the skin surface when subcutaneously implanted. Insertion of the access tube 621 into the tapered seat opens the conduit to physiological pressure and continuous blood flow through the conduit. The port 664 includes a nozzle 670 with an outlet opening 665 which is attached to a catheter 620. The catheter may contain pores 668 and/or a central opening 669. The catheter 620 interfaces with the blood vessel 631 or other body space filled with (or potentially filled with) a fluid (i.e. blood, urine, cerebral-spinal fluid). It is contemplated that the device can be used for various therapies beyond hemodialysis with little or no modification. Some other therapeutic uses may include peritoneal dialysis, urinary tract drainage, pleural effusion and cerebral-spinal fluid drainage. The port may be used to administer insulin or even inflate a penile prosthetic, for example.

Figure 7A:
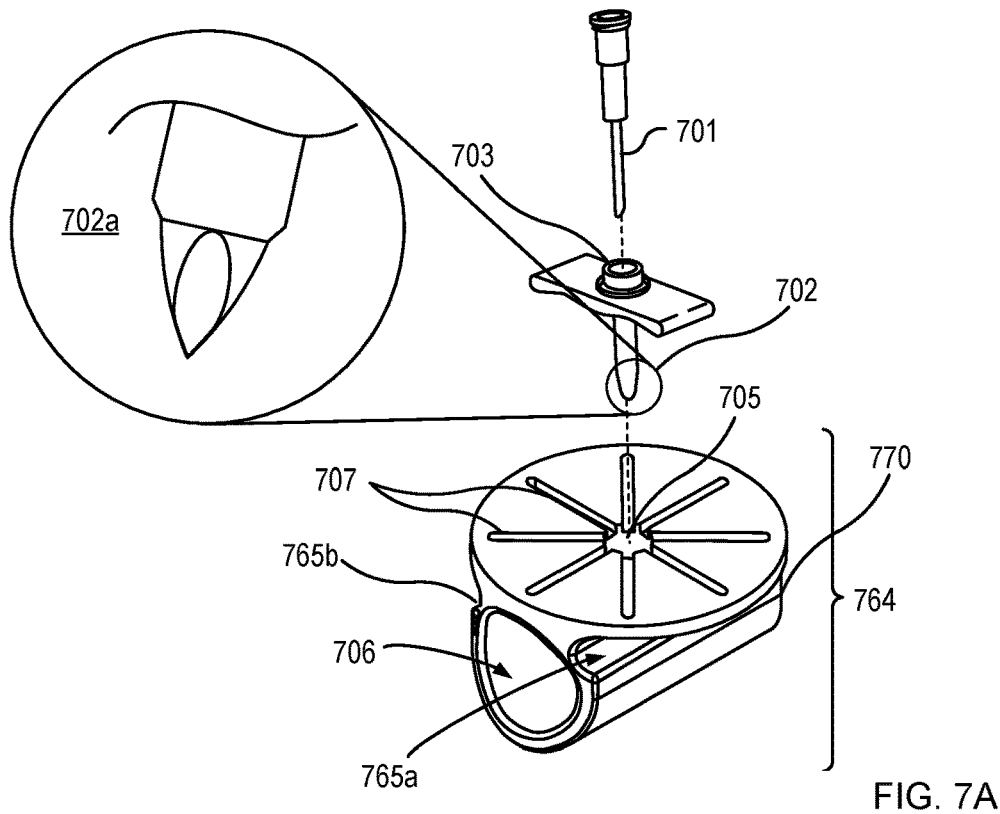
FIG. 7A is an exploded view of the port device according to an embodiment of the invention.

FIG. 7A is an exploded view of the needle 701 which fits inside an opening 703 in the trocar 702. The tip 702a of the trocar is non-coring and non-lacerating for added patient comfort. The trocar 702 fits inside the tapered seat of the port 664. The nozzle 770 connects to the catheter (not shown). An area 706 provides a space for excursion of the optional valve assembly. The port may be configured to attach a stabilizer wire at grooves 765a, 765b on each side of the port 764.

Figure 7B:
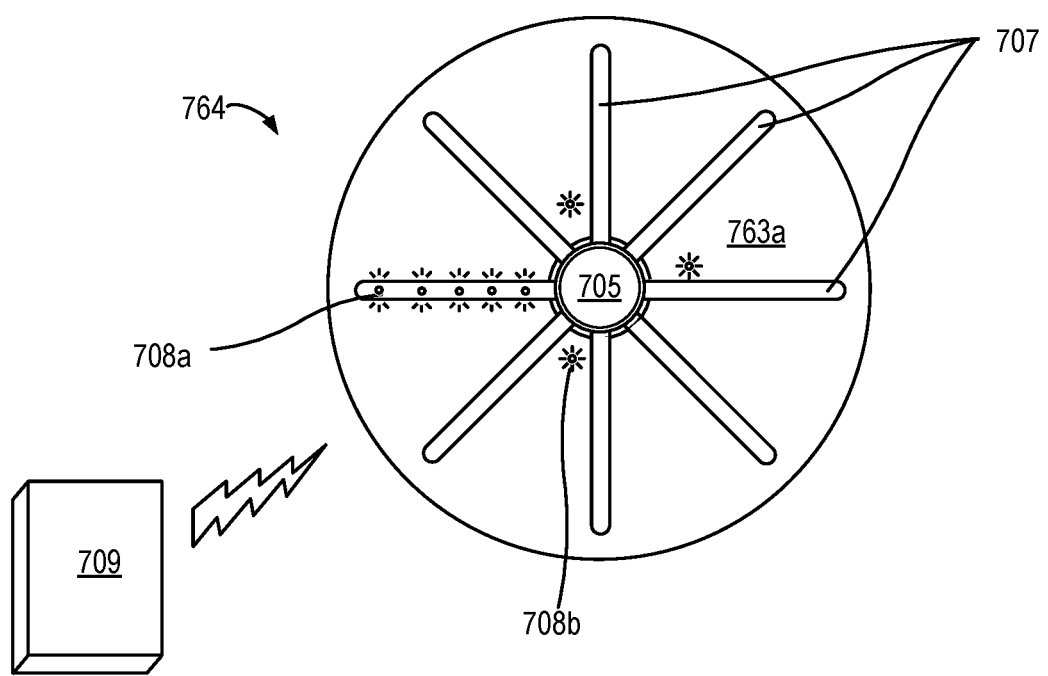
FIG. 7B is a top view of the port device according to an embodiment of the invention.

FIG. 7B show a top view of the port body 764 including the opening on the tapered seat 705 and guide 707. The guide 707 may include a ridge elevated from the flat surface 763a to guide the access tube into the opening 705 after the access tube has pierced the skin. The ridge may be rounded or flat on top. Other elevated configurations are contemplated to catch the tip of the access tube in the vicinity of the opening 705 and guide the access tube toward the opening 705 along the intersection of the flat surface and beginning of the ridge elevation. Alternatively, the device 764 (or at least the flat surface 763a) may include a transparent material and the guide may include LED lights 708a, 708b (alone or in combination with the ridge embodiment) and a receiver coil for receiving an electrical current. The lights may be arranged in many configurations including a ring arrangement, a linear 708a arrangement (pointing toward the opening 705) or a triangular 70b arrangement (surrounding the opening 705), for example. The LED lights may include ruby, sapphire or other durable, radiant material visible through the skin of the patient and the lights may be arranged in a ring configuration raised above the flat surface 763a to engage the access needle, for example. The lights are configured to illuminate when an electromagnetic induction chip 709 is placed external to the patient and substantially above the subcutaneously implanted device. The induction chip producing a voltage in the receiver coil, the voltage powering the lights so that a location of the subcutaneously implanted device is visually revealed to the health care professional.

Figure 7C:
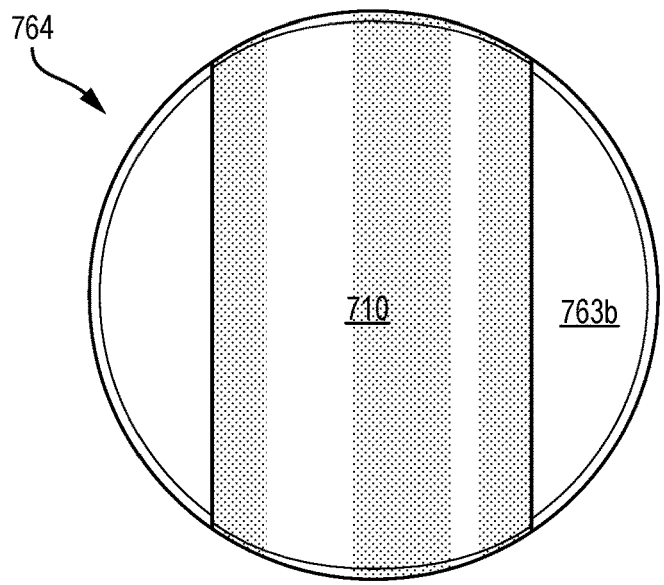
FIG. 7C is a bottom view of the port device according to an embodiment of the invention.
Figure 7D:
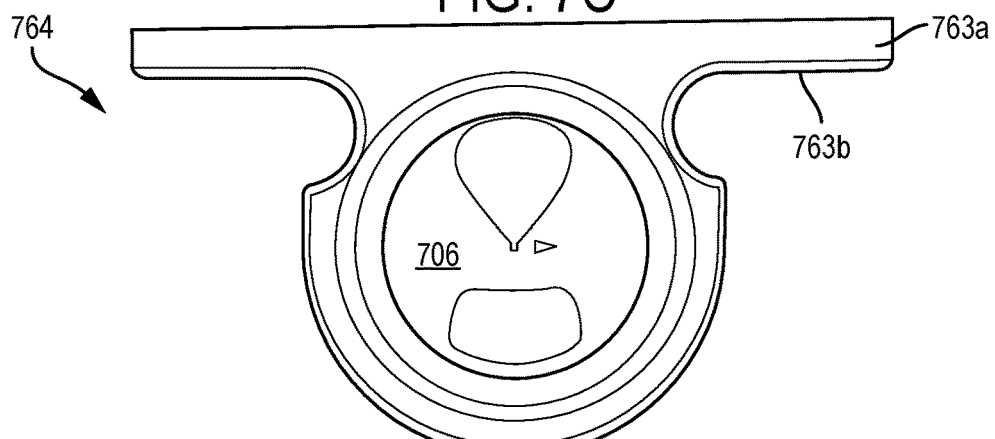
FIG. 7D is a back view of the port device according to an embodiment of the invention.
Figure 7E:
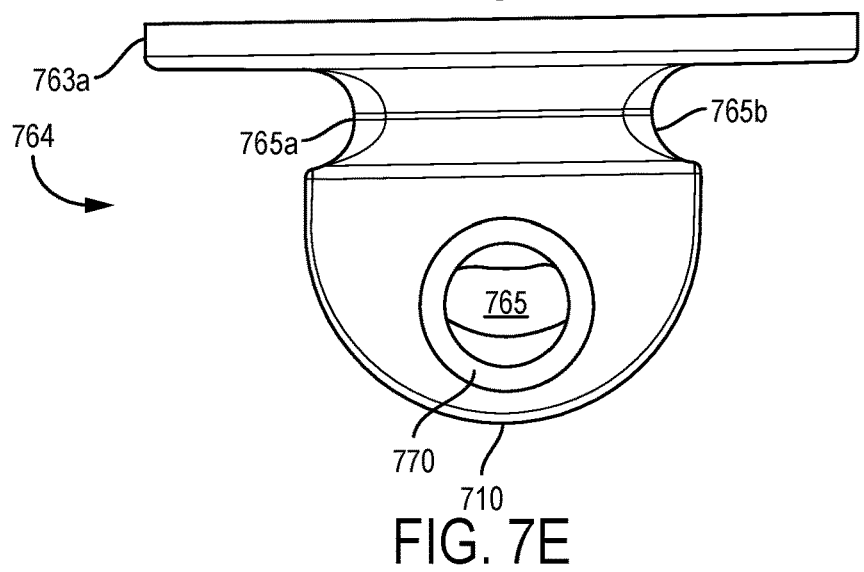
FIG. 7E is a front view of the port device according to an embodiment of the invention.
Figure 7F:
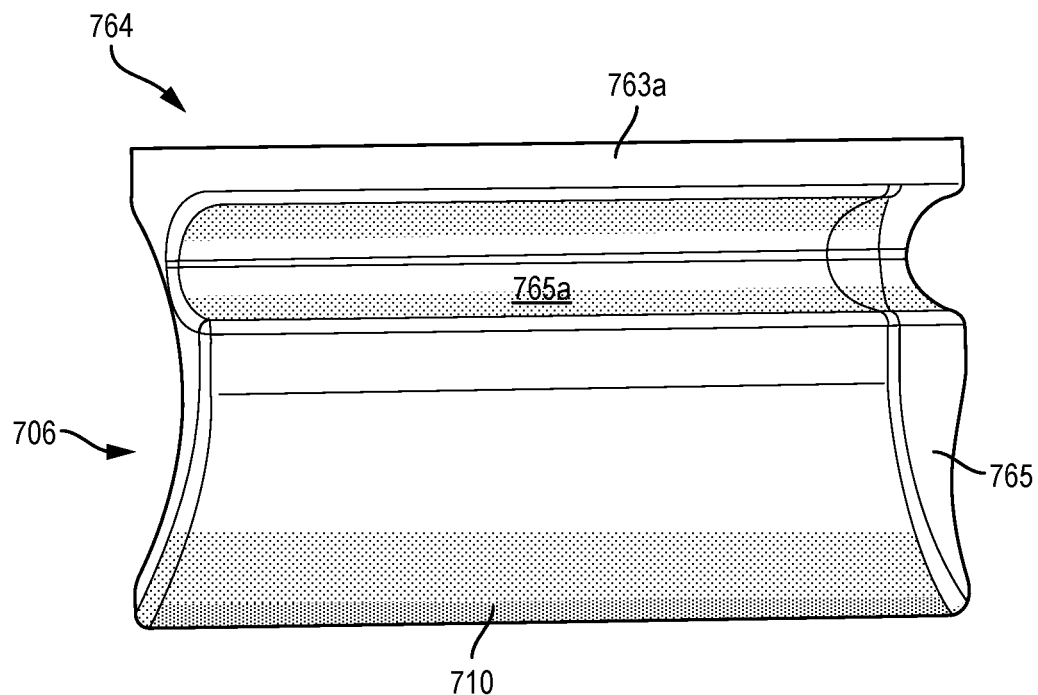
FIG. 7F is a side view of the port device according to an embodiment of the invention.

FIG. 7C a bottom view of the port device 764 according to an embodiment of the invention including the underside 763b of the flat surface 763a. FIG. 7D is an end view showing the area 706 that provides a space for excursion of the optional valve assembly. FIG. 7D is an end view of the area 706 that provides a space for excursion of the optional pressure competent valve assembly. The opposite end of the device 764 from FIG. D is shown in FIG. 7E. FIG. 7E includes the catheter attachment area (i.e. nozzle) 770 and outlet opening 765 which is attached to a catheter (not shown). An optional stabilizer wire may be attached at grooves 765a, 765b on each side of the port 764. FIG. 7F is a side view of the port device 764

Figure 8:
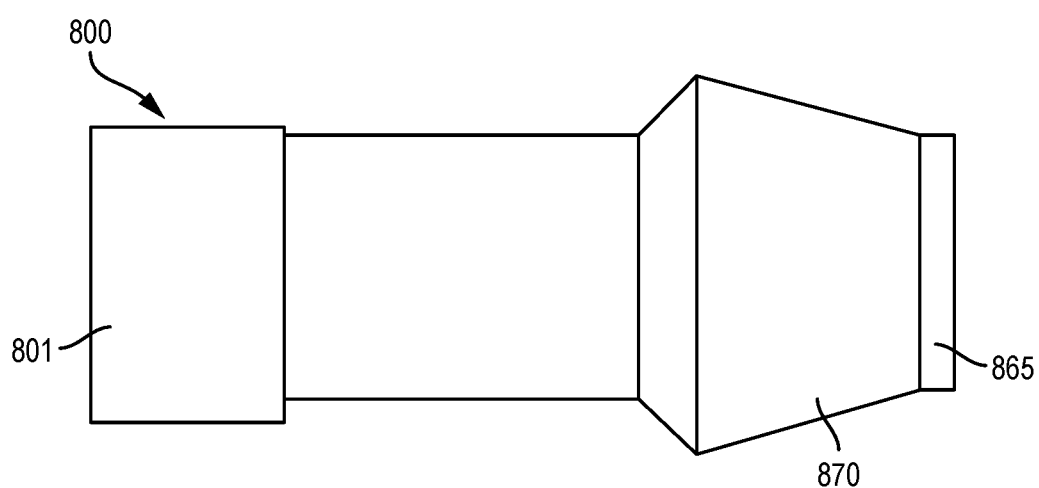
FIG. 8 is a side view of a catheter connector according to an embodiment of the invention.

An alternative manufacturing method to the single molded port 664 shown in FIG. 6, is a two piece press-fit configuration depicted in port 764 shown in FIGS. 7C-7F and catheter connection 800 shown in FIG. 8. The cyndrical end 801 of the catheter connection 800 can be inserted into the body 764 of the device at outlet opening 765 shown in FIG. 7F. Machining technology ensures a snug fit between the port 764 and catheter connection 800. When inserted, the nozzle 870 and nozzle opening 865 protrude from the outlet opening 765 to facilitate connecting the nozzle 870 to a catheter. The press-fit configuration may allow better fit with the ball seating, for example.

FIG. 9A-9I are examples of ridge and/or light pattern guide configurations according to certain embodiments of the invention as viewed from the top of the flat surface 963a. The guide 907a may extend from the centrally-located tapered seat opening 905 to the edge 963c of the flat surface 963a (as shown in FIG. 9A) or the guide 907b may extend from the opening 905 to a distance 901 short of reaching the edged 963c of the flat surface 963a (as shown in FIG. 9F), for example. The guide configurations may include a combination of distances from the opening 905 as depicted in FIGS. 9B and 9G, for example. The guide(s) can be straight (i.e. FIGS. 9A, 9B, (E, 9F, 9G, and 9I) or the guide may be curved (FIGS. 9C, 9D and 9H). FIG. 9I is a preferred embodiment with is also generally shown in FIGS. 16C, 16D, 17C, 17D also. In some embodiments, the guide forms a target-like shape where the lights and/or ridges do not extend from the tapered seat opening 905 as shown in FIGS. 9D and 9E, for example. Of course, many other configurations are possible and the present invention is not limited to the examples provided herewith. One purpose of the guide is to assist the health care professional in accessing the opening to the tapered seat. The device can be palpated when it is implanted just under the skin. While it is possible to pierce the skin with the access tube and directly insert it into the tapered seat, a more likely scenario is to palpate the subcutaneously implanted device and feel the circular edges of the flat surface (which is about the diameter of a dime). The diameter may be about 14 mm but is scalable for alternative applications. After the location of the flat surface has been felt, the access tube punctures the skin in the vicinity of the opening of the tapered seat. The tip of the access tube engages (e.g. bumps into) the ridge and the access tube is moved along the guide ridge until if finds the opening.

FIG. 10A is a side view of a slit valve mechanism according to an embodiment of the invention. The port device is implanted under the skin surface 1025. The tapered seat 1003 has an opening 1005 that is centrally-located on the flat surface 1063 of the port device. The distance 1004 of the tapered seat 1003 is between about 1.0 mm and 5.0 mm. Preferably, the distance is between about 1.5 mm and 2.5 mm as this has been found to provide maximum dependability and functionality while minimizing the height of the device. A semi-rigid silicon disc 1001a includes a centally-located slit 1002a that is generally aligned with the center of the tapered seat 1003. A plate 1001b sits on top of silicon disc 1001a. The plate 1001b may be made of metal, plastic, or other hardened material. A top view of the plate 1001b is shown in FIG. 10B. Slits 1008a, 1008b, 1008c form multiple pie shaped wedges that spread downward into the silicon disc 1001a when an access device travels down the tapered seat 1003 and contacts the centrally-located intersection of the slits 1009. As the slits 1008a, 1008b, 1008c spread apart and downward into the silicon 1001a, slit 1002a opens to allow the access tube passage through the silicon to open the conduit. Of course, many other mechanisms that are capable of spreading the slit 1002a apart could also be used to open the valve. Upon removal of the access tube at the conclusion of a treatment, the silicone rebounds to close the slit 1002a, the slits 1008a, 1008b, 1008c also rebound to seal the valve closed.

The plate 1001b serves to protect the relatively softer silicon 1001a from cuts and abrasions from the access tube. The access tube does not directly contact the silicon to open slit 1001a. Rather the plate opens slit 1001a. This prevents damage to the silicon 1001a from the access tube and lengthen the live of the valve, for example. FIG. 10C is a top view of the closed slit valve of FIG. 10A with the plate 1001b removed. FIG. 10D shows the oval shape of the silicon disc 1001a before the disc is positioned in the device and thus constrained by the device in direction 1006 to form an essentially circular shape per FIG. 10C with the valve loaded in an initial closed position.

Figure 11A:
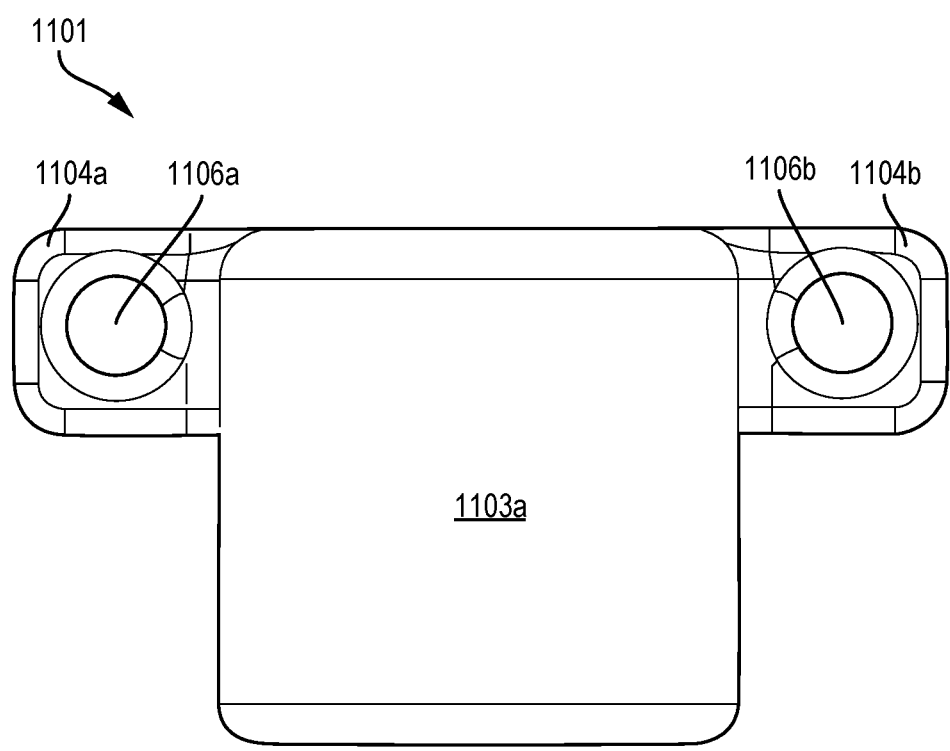
FIG. 11A is a top view of an over mold according to an embodiment of the invention.

FIGS. 11A-11G show various views and types of over molds 1101, 1102 that may be attached from the underside 1110 of the device to assist in stabilizing and/or anchoring the device. One embodiment of an over mold 1101 is shown in FIG. 11A and includes suture rings 1106a, 1106b on each side of wing-like protrusions 1104a, 1104b extending from the over mold central body 1103a. The over mold 1101. 1102 may be attached to the device on the side opposite the smooth surface with guides so that access to the tapered seat is not occluded by the over mold. The over mold can be a single molded configuration and separate from the port device or the over mold and port can be integrated or even fused together. A single molded configuration may be machined or molded and has no seams or parts than require adhesive or fastening, for example.

Figure 11B:
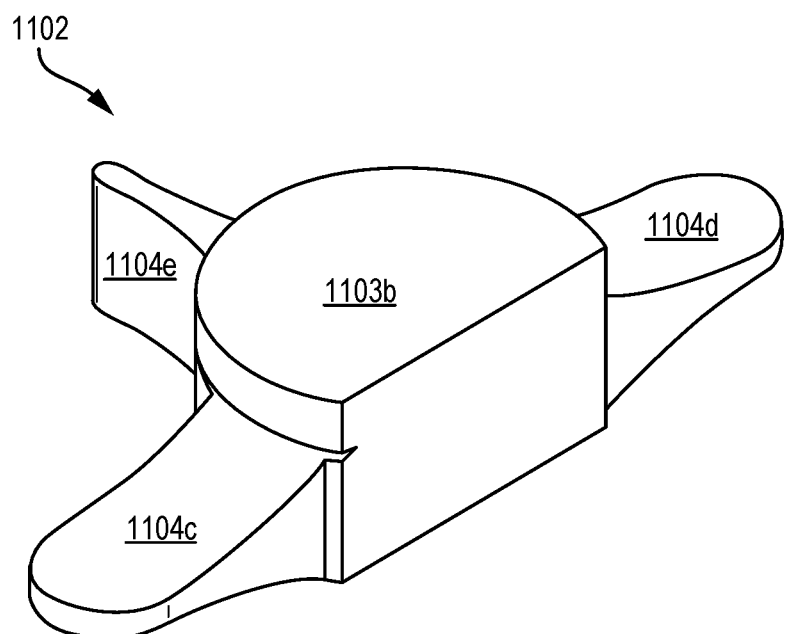
FIG. 11B is a perspective view of an over mold according to an embodiment of the invention.
Figure 11C:
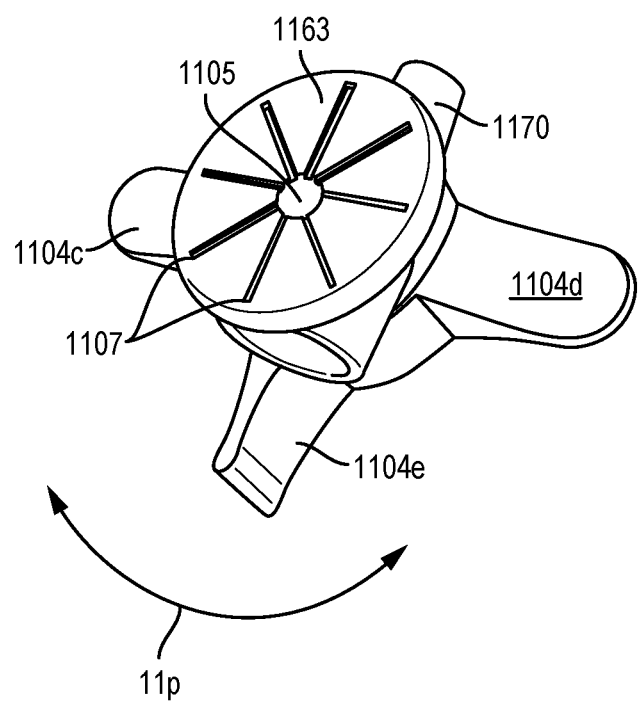
FIG. 11C is a top perspective view of an over mold attached to the port according to an embodiment of the invention.
Figure 11D:
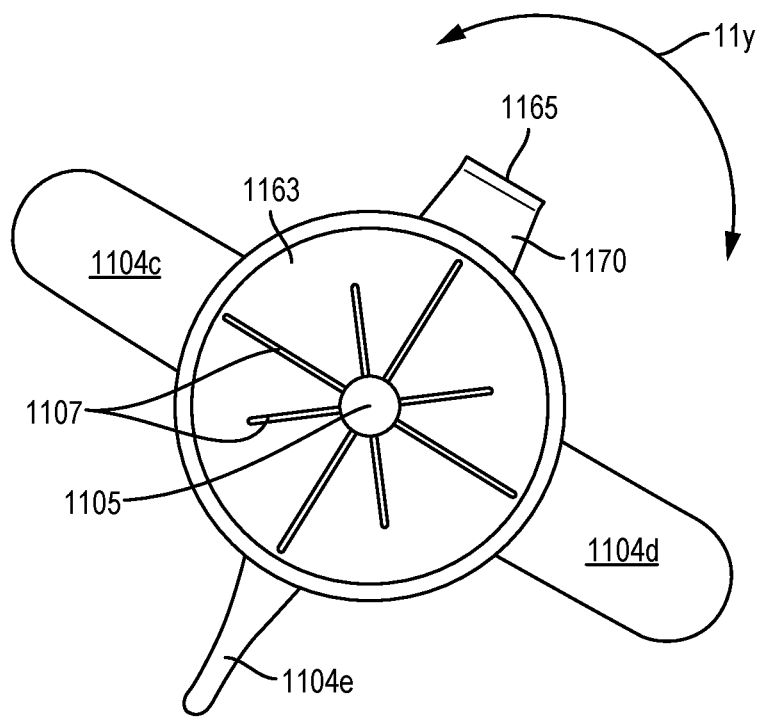
FIG. 11D is a top view of an over mold attached to the port according to an embodiment of the invention.
Figure 11E:
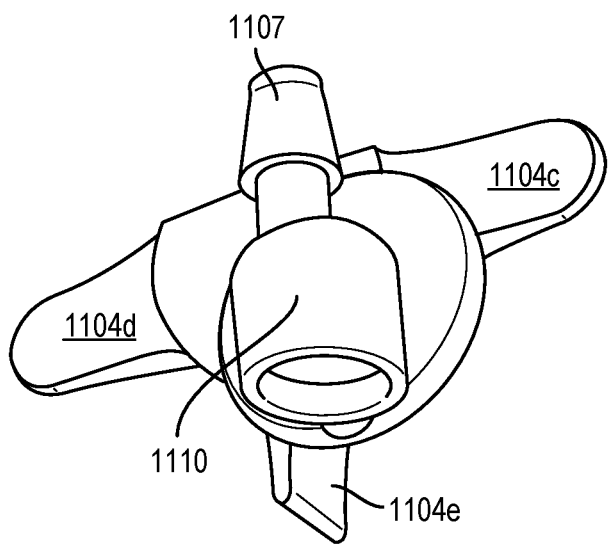
FIG. 11E is a bottom perspective view of an over mold attached to the port according to an embodiment of the invention.
Figure 11F:
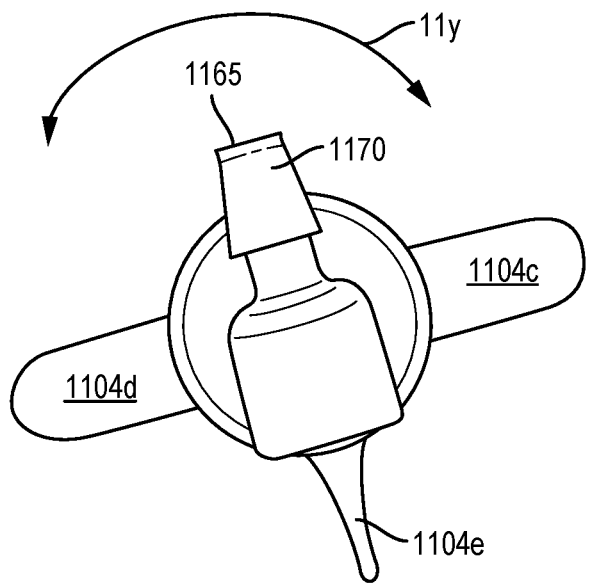
FIG. 11F is a bottom view of an over mold attached to the port according to an embodiment of the invention.
Figure 11G:
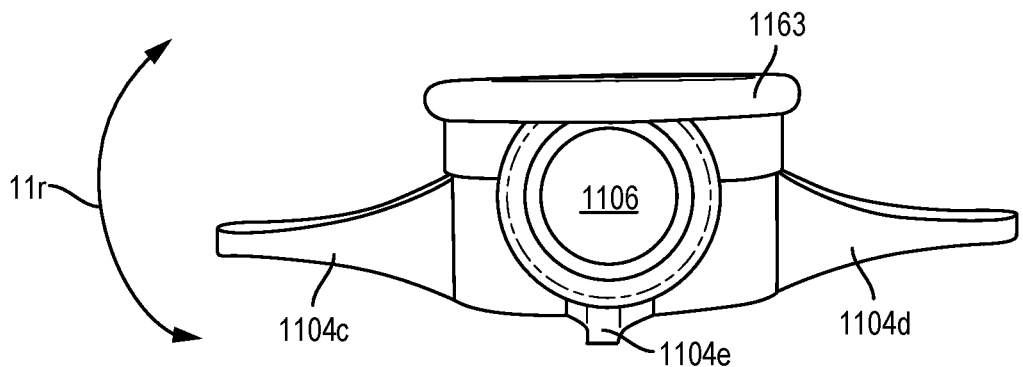
FIG. 11G is a back view of an over mold attached to the port according to an embodiment of the invention.

An alternative embodiment of an over mold 1102 is depicted in FIG. 11B where three wing-like extensions serve to widen the base of the device so that the implanted device is not prone to move, wobble or tilt when the access tube is inserted during use. In this embodiment, horizontally flattened wings extend from the over mold body 1103b to each of opposite sides 1104c, 1104d along a horizontal plane. Additionally, a vertically flattened wing 1104e may extend in from the port body 1103b in the same general plane as the wings 1104c, 1104d and at about 90 degrees from wings 1104c and 1104d. One example of how the over mold is attached to the port device is shown in various perspectives at FIGS. 11C-11G, for example. The wings prevent or minimize linear and/or rotational motion of the device. The wing 1104e minimizes yaw movement 11y in a similar way a rudder prevents yaw movement in an airplane during flight. Wings 1104c and 1104d minimize roll movement 11r (and to some extent also limit pitch movement 11p) when the device is implanted. The nozzle 1170 is located at the opposite end of the device (180 degrees) from wing 1104e.

Figure 11H:
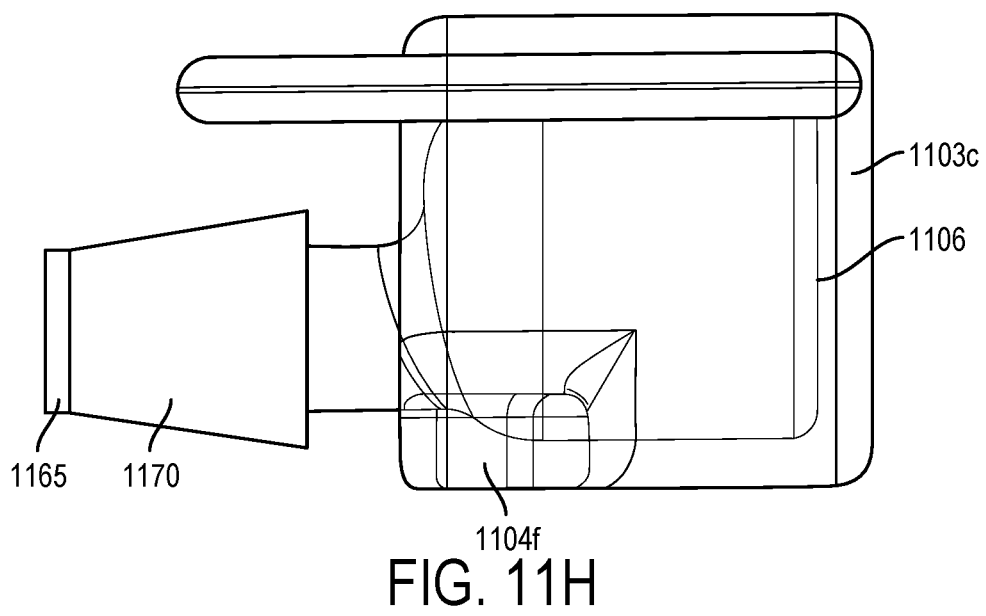
FIG. 11H is a side view of the port with a resorbable stabilizer attached according to an embodiment of the invention.
Figure 11I:
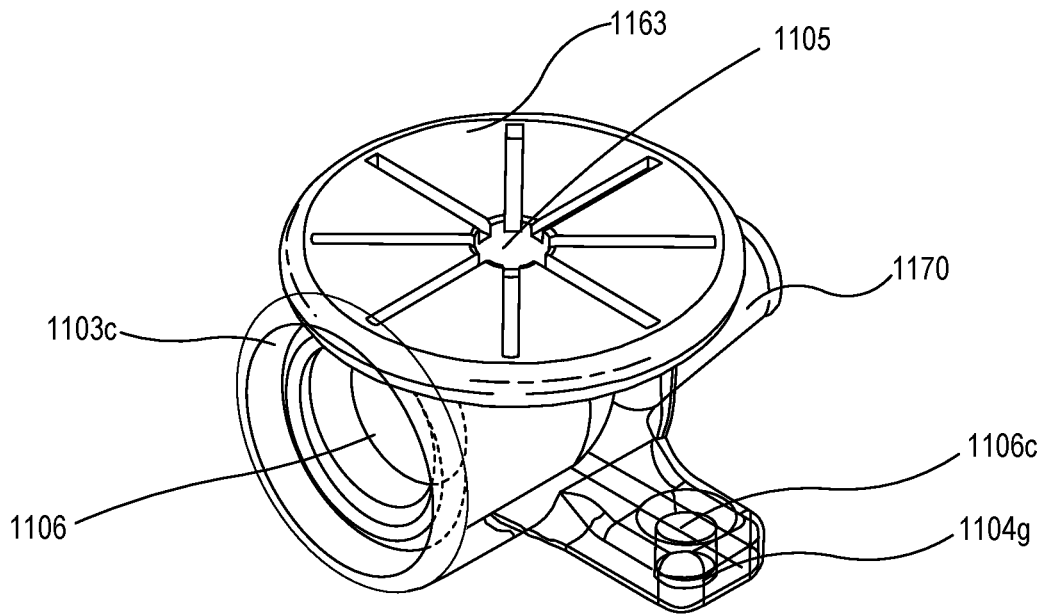
FIG. 11I is a perspective view of the port with a resorbable stabilizer pocket attached according to an embodiment of the invention.

FIGS. 11H-11I show another embodiment of an over mold made of a bioresorbable, bioabsorbable or a biodegradable material 1103e. The material 1103e may include polylactide (PLA), polycaprolactone (PCL), polydioxanone (PDX), poly(L-glutamate), poly (L-lysine), or poly(L-leucine), for example. The over mold resorbs or degrades over time ultimately leaving the port device implanted. The over mold may promote or at least support tissue integration to secure the implanted device and limit movement of the device. The over mold may include suture rings 1106c, 1106d on each side of wing-like protrusions 1104f, 1104g that extend from the over mold. The suture rings may be resorbed or degraded over essentially the same time period as the over mold resorbs absorbs or degrades into the surrounding tissues of the patient's body.

Figure 11J:
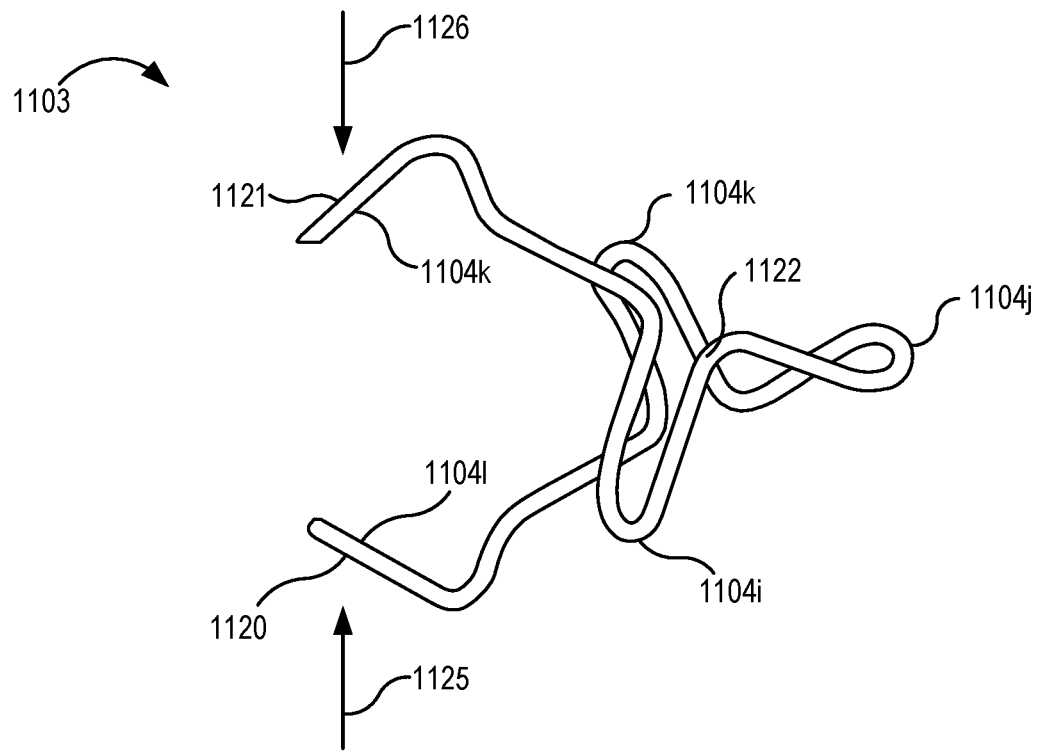
FIG. 11J is a top view of the stabilizer wire in a pre-deployment configuration according to an embodiment of the invention.
Figure 11K:
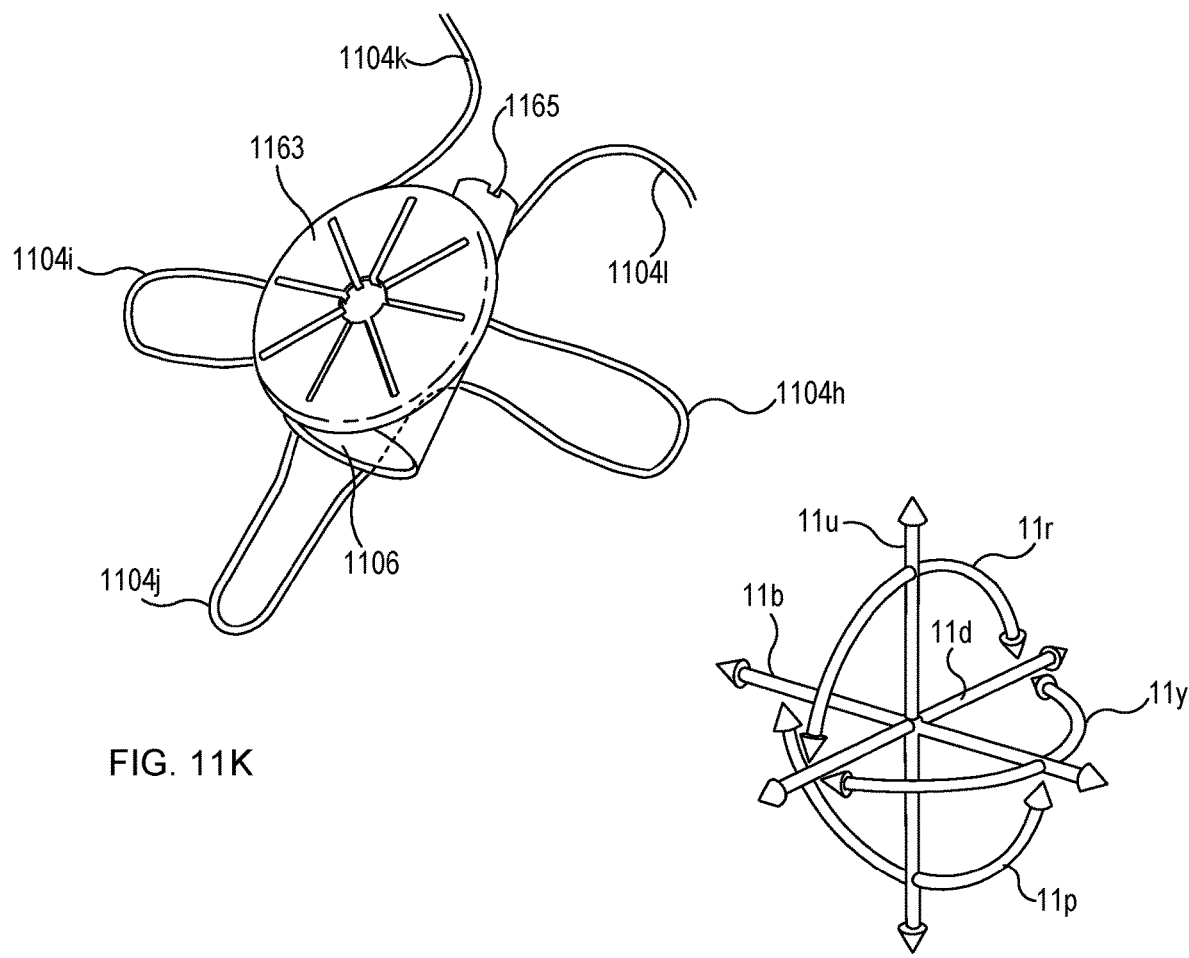
FIG. 11K is a perspective view of the port with a stabilizer wire attached according to an embodiment of the invention.
Figure 11L:
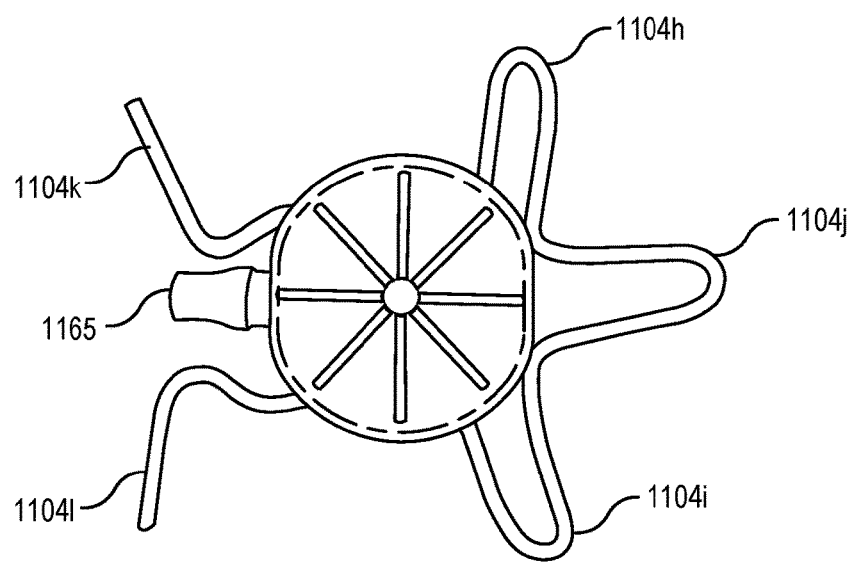
FIG. 11L is a top view of the stabilizer wire attached to the port in a post-deployment configuration according to an embodiment of the invention.

FIG. 11K is a perspective view of a port device with a stabilizer wire 1103 attached. The wires may be made of any rigid metallic material although a magnesium wire with a diameter of about 2 mm is preferred. One advantage in using magnesium wire is that is safely and gradually degrades to form magnesium hydroxide in the presence of human body fluids (and other electrolytic solutions), when implanted. Magnesium hydroxide is not known to have any adverse side effect on the human body. As seen in FIGS. 11K and 11L, the deployed wire attached to the device at grooves 765a, 765b (FIG. 7) take on a cruciate configuration (i.e. cross shape). The wings 1104h, 1104i, 1104j are intended to prevent or minimize movement in various directions along various planes (i.e. up/down 11u, left/right 11d, yaw 11y, pitch 11p, backward/forward 11b) in a similar manner as previously described regarding other stabilizer wire embodiments. Additional stabilization may be realized from the open ends of the wire 1104k, 1104l near the nozzle opening 1165 of the port device especially in movements 11b, 11d. FIG. 11J shows the wire stabilizer before deployment and before attachment to the port. After the port is subcutaneously implanted in the patient, the wire stabilizer is grasped (preferably) by the thumb and index finger of a health care professional at locations 1120 and 1121, respectively, and leading tip of the stabilizer wire 1104j is inserted (e.g. gently pushed) into a small incision in the patient's skin near the location of the implanted port. This technique avoids the step of surgically creating a tissue pocket to receive the stabilizer wire. Pre-deployed wings 1104h, 1104i follow as the wire in pushed through the incision opening and beneath the skin. When all or most of the wire stabilizer is implanted under the skin, the stabilizer is deployed to an open position by gently compressing the wires in directions 1125a and 1126. The wire 1103 and port device 764 are then be positioned by palpating the wire and port under the skin to engage the wire 1103 in the grooves 765a, 765b. The device is centered at the apex of the wire crossing 1122 and center the device in the opened wires. It should be noted that the apex 1122 is the only location where the wires are cross in the pre-deployment configuration and require deformation to uncross the wires at apex 1122 by applying direction forces 1125 and 1126. The configuration of this wire stabilizer is both elegant in its simplicity while also allowing a lot of mechanical advantages. Once the wire is released from positions 1120 and 1121, the wire rebounds slightly with a spring or memory force to apply tension to the device holding the wire in the grooves 765a, 765b. Each wing 1104h, 1104i, 1104j provides a low profile blunt end stabilizer without tearing the skin. The ends 1121 and/or 1120 may be shortened by trimming them with a wire cutter if needed and the incision can be closed with sutures, for example.

Figure 12A:
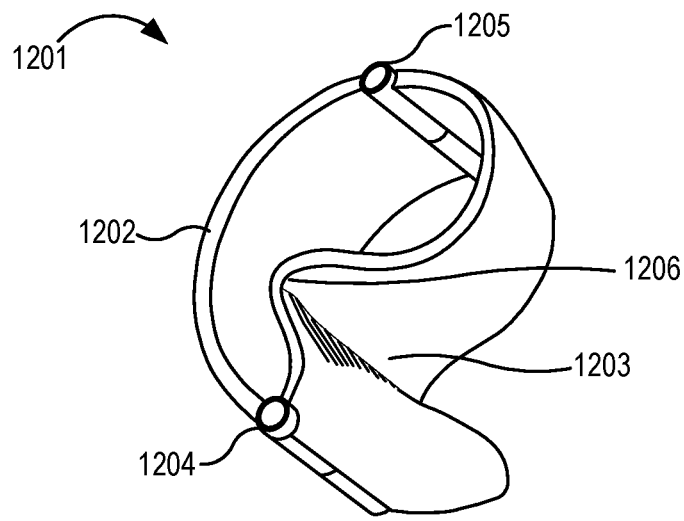
FIG. 12A is a perspective view of a vortex clamp according to an embodiment of the invention.
Figure 12B:
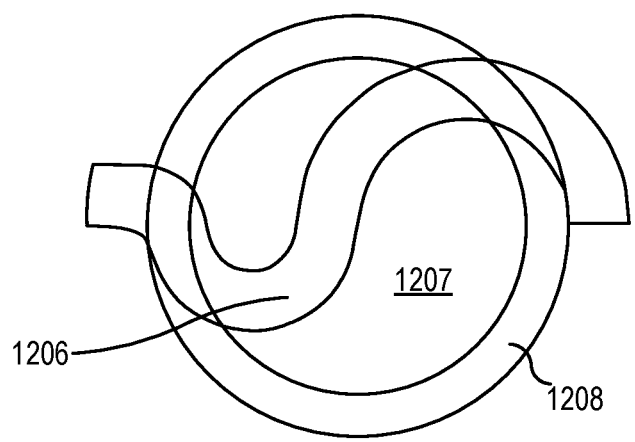
FIG. 12B is a side view illustration of a vortex clamp in a flow path according to an embodiment of the invention.

Now turning to FIGS. 12A-12B, a vortex clamp 1201 may be removably attached to the outside of a blood vessel or synthetic tube which, in turn, is attached to the port device. The unique shape of the clamp modifies the vascular blood flow path 1207 and reduces fluid turbulence through the vessel 1208 when the valve is open and the vortex clamp is positioned around a blood vessel. The vortex clamp includes a side 1202 that is essentially a semi-circular shape and another side 1203 that includes an indented portion 1206. Side 1202 is connected by hinge mechanisms 1205 to the opposite side 1203 in a clam shell configuration to allow the vortex clamp to surround and close around the outside of the vessel and fasten securely with a latch mechanism 1204. FIG. 12B shows a side view illustration of a vortex clamp in a flow path according to an embodiment of the invention. The vortex clamp changes the vessel shape from an essentially cylindrical shape to a helical shape which changes the flow through the vessel from a laminar to a vortical flow.

Figure 13A:
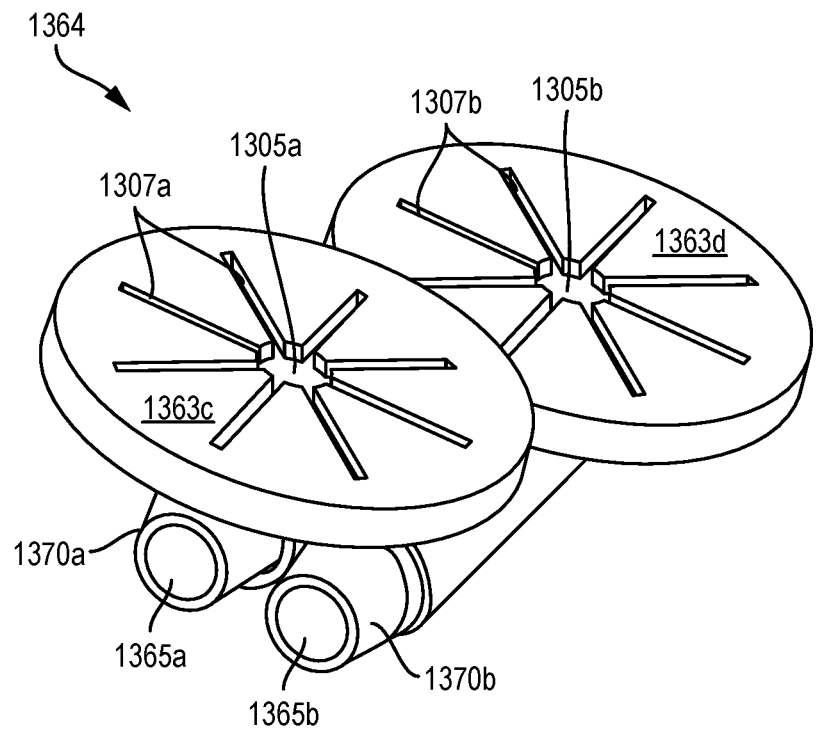
FIG. 13A is a top front perspective view of a double port configuration according to an embodiment of the invention.
Figure 13B:
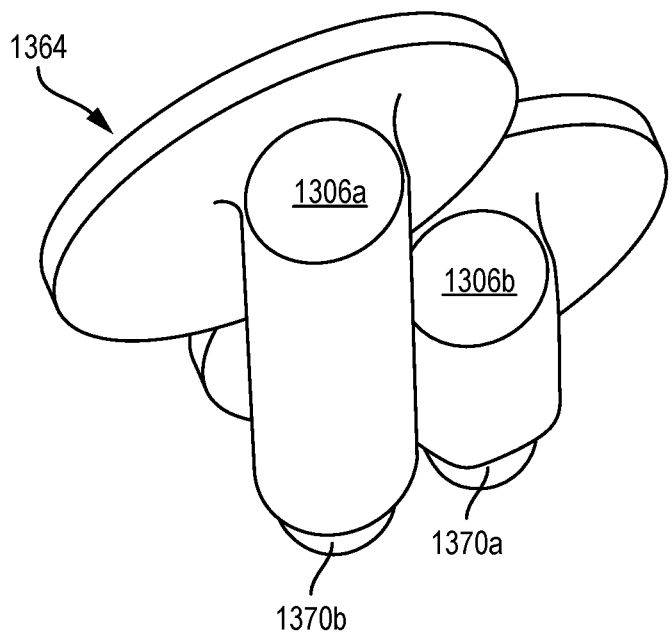
FIG. 13B is a bottom back perspective view of a double port configuration according to an embodiment of the invention.

FIG. 13A is a front perspective view of a double port configuration according to another embodiment of the invention. This configuration is essentially two ports 664 (as shown in FIG. 6) fused together into a single implantable double port device 1364. The double port 1364 has separate flat surfaces 1363c, 1363d, guides 1307a, 1307b, openings to the tapered seat 1305a, 1305b, conduits, valves, and nozzles. The areas 1306a, 1306b, shown in FIG. 13B, provide spaces for excursion of the optional valve assembly. The nozzles 1370a, 1370b can be connected to a catheter (not shown). One double-lumen catheter or two single-lumen catheters can be used to establish access to the patient's blood vessel via outlet openings 1365a, 1365b.

FIG. 13C depicts an insertion sequence of two access tubes, each tube opening a separate associated port in the double port device. It is contemplated that the double port device can be used to deliver two different therapies simultaneously (e.g. each therapy through one access tube). Alternatively, the double port can be used to deliver a double dose of the same therapy (e.g. one therapy through each access tube) which may reduce the time of the procedure by about 50% or more in some cases. Some of the many therapeutic uses of the double port may include hemodialysis, peritoneal dialysis, urinary tract drainage, pleural effusion and cerebral-spinal fluid drainage or combinations thereof, for example. Each of the two tapered seats may fit with a diameter of each of two access tubes to include any combination of mismatched or matched configurations (as described with respect to FIGS. 4A and 4B) to create a combination of therapeutic procedures requiring relatively high pressure flow rates and/or requiring relatively low pressure flow rates. High pressure flow rates are considered to be flow rates greater than or above normal physiologic pressures and flow rates less than or below normal physiologic pressures are considered low pressure flow rates. Therefore, it is possible to administer dialysis (high flow rate) and intravenous fluids (low flow rate) simultaneously using the double port, for example.

Figure 1:
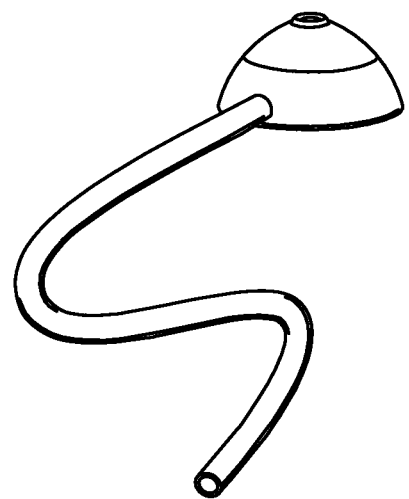
FIG. 1 shows a conventional implantable hemodialysis port.

Referring to FIG. 13C1, the double port device 1364 is implanted under the patient's skin 1325. An access tube 1321a (i.e. trocar) may include a swivel attachment 1324 to attach a connecting line 1323. The swivel mechanism 1324 is capable of rotating 360 degrees in a clockwise or counter-clockwise direction 1398 to prevent the connecting line 1323 from binding if the patient moves.

Figure 2:
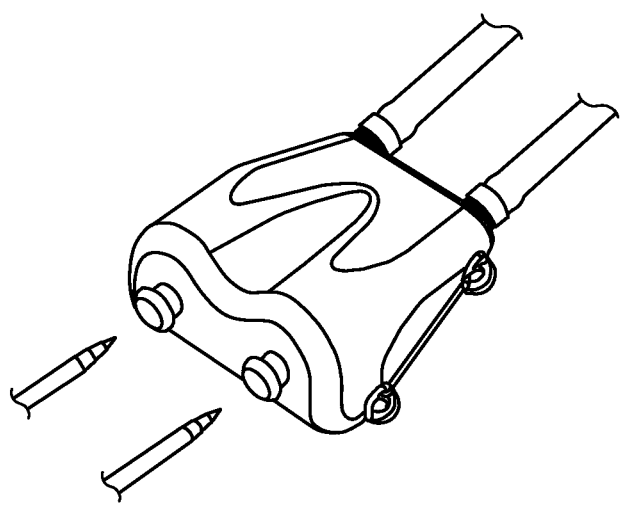
FIG. 2 shows another conventional implantable hemodialysis port.

An access tube 1321a is inserted through the skin 1325 and contacts the flat surface 1363a. The tip of the access tube 1321a engages a guide 1307 and the access tube is moved along the guide to find the centrally-located opening of the tapered seat 1305a. The access tube is inserted into the tapered seat (FIG. 13C2). A pressure competent valve is opened via percutaneous insertion of the access tube into the tapered seat. The valve may include a polymer spring (FIG. 15), silicon disc (FIGS. 5, 10A-10D), a sphere (FIGS. 11A-14G) or other valve configuration. A needle 1301a is removed 1397 from a lumen of the access tube (FIG. 13C3). The needle may be a single use needle. A clear container space 1399, located between the access tube and the swivel attachment, can be used to confirm the valve is open to continuous blood flow (or other body fluid) by viewing the blood (or other body fluid) in the clear container space 1399. The valve allows continued vascular blood flow through the conduit and the flow unobstructed by the access tube. The access tube may be rotated 1396 about 45 degrees to lock in place (FIG. 13C4) and/or a snap-fit or other similar configuration ensures the access tube is securely inserted into the tapered seat. This process is repeated by inserting a second access tube 1321b through the skin 1325 (FIG. 13C5) to contact the flat surface 1363b. The tip of the access tube 1321b engages a guide 1307 and the access tube is moved along the guide to find the centrally-located opening of the tapered seat 1305b. The access tube is inserted into the tapered seat (FIG. 13C6). A second valve is opened via percutaneous insertion of the access tube into the tapered seat. A needle 1301b is removed from a lumen of the access tube (FIG. 13C6). A clear container space 1399, located between the access tube and the swivel attachment, can be used to confirm the valve is open to continuous blood flow. The access tube may be rotated 1396 about 45 degrees to lock in place (FIG. 13C6) and/or a snap-fit or other similar configuration ensures the access tube is securely inserted into the tapered seat. In this manner, two access tubes are used to each open separate valves to continuous blood flow (or other body fluid) via a catheter (not shown) attached to the outlet openings 1365a, 1365b.

Figure 13D:
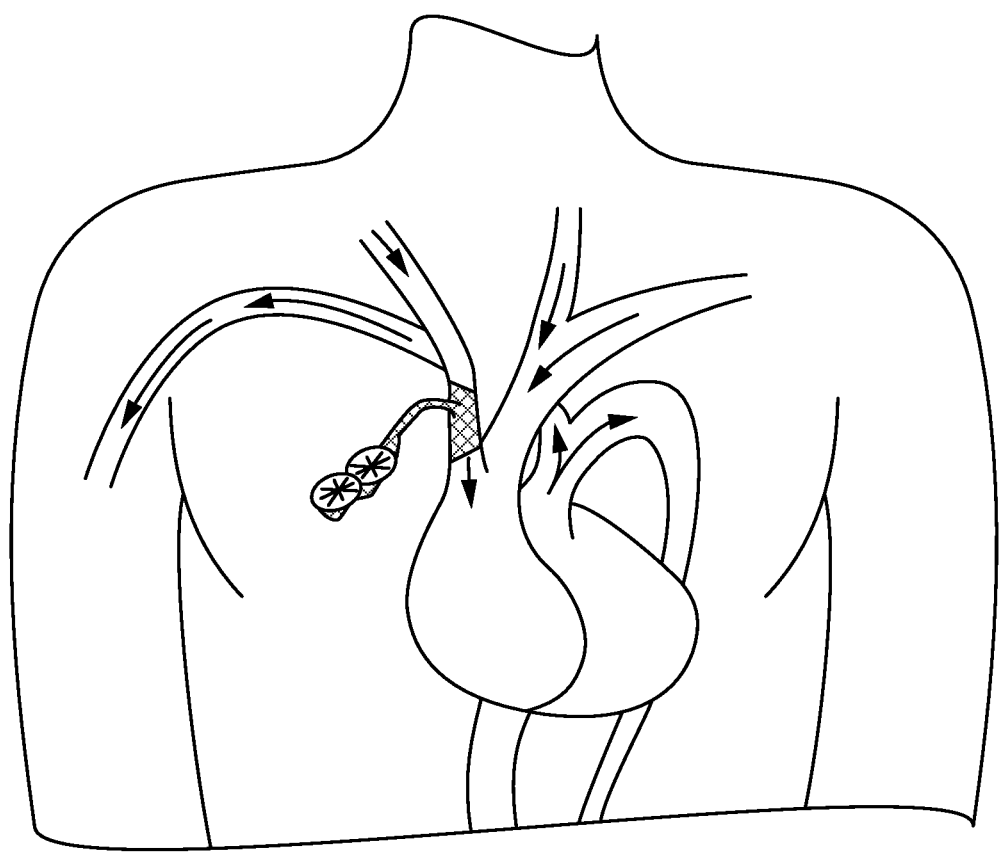
FIG. 13D shows a double port implanted in a patient and connected to a blood vessel with a T-catheter according to an embodiment of the invention.

FIG. 13D shows one of many examples of how the implanted device may access a blood flow. In this example, a T-catheter is attached to the device and used to access a vessel. The outside walls of the T-catheter are proximate the inside walls of the blood vessel so that the catheter takes up most or all of the space of the vessel lumen. In this way, all or the majority of the blood flow path flows through the conduit of the catheter. This configuration provide a more efficient therapy and also reduces blood flow turbulence, clotting, and other hemodynamic consequences. The valve is closed upon removal of the access tube from the tapered seat at a treatment conclusion.

Figure 13E:
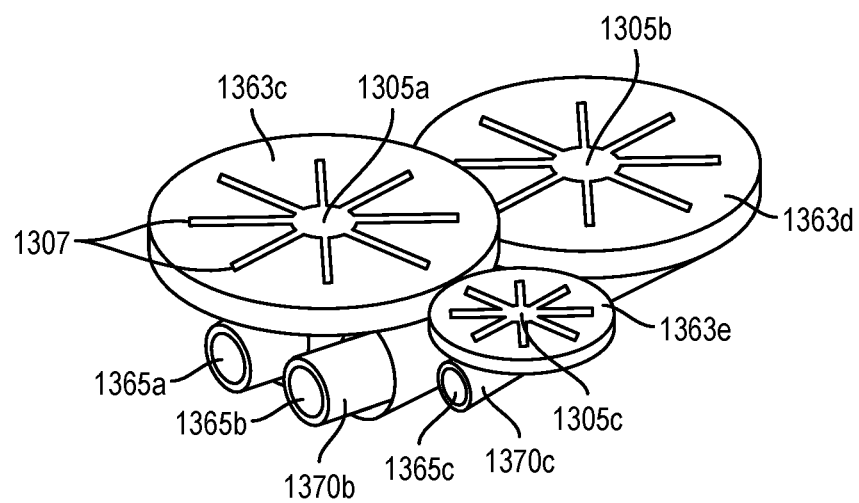
FIG. 13E is a perspective view of a triple port configuration according to an embodiment of the invention.

FIG. 13E is a perspective view of a triple port configuration according to an embodiment of the invention. This embodiment illustrates, in part, that the flat surfaces may be scalable for alternative applications. Flat surface 1363e is relatively smaller diameter than flat surfaces 1363c or 1365d, for example. In a manner similar to the double port configuration described above and with respect to FIGS. 13A-13D, the triple port can be used to deliver three different therapies simultaneously (e.g. each therapy through one access tube). Alternatively, the triple port can be used to deliver a triple dose of the same therapy (e.g. one therapy through each access tube). Also, in a manner similar to the insertion sequence described above and with reference to FIG. 13C, the triple port follows a similar sequence using three access tubes. It is contemplated and is understood by those of ordinary skill in the art that additional fused port configurations in excess of three ports can also be used in a similar manner as disclosed and described herewith.

Figure 14A:
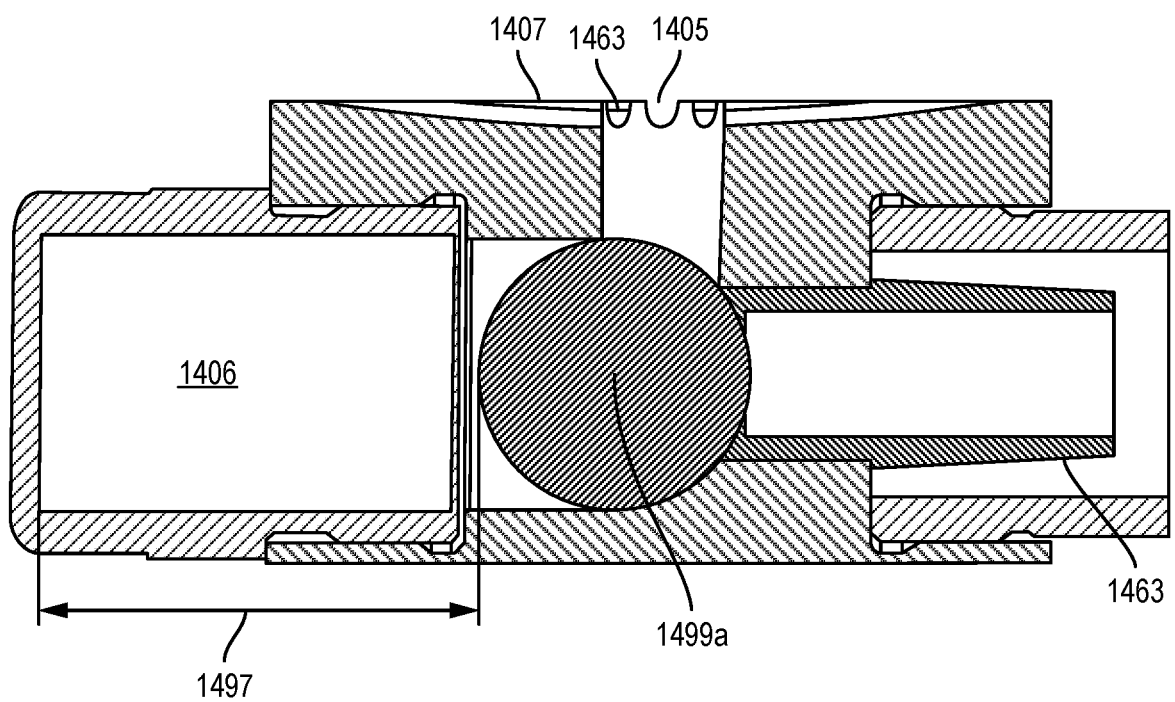
FIG. 14A is a cut-a-way side view illustration of a ball valve in a closed position according to an embodiment of the invention.
Figure 14B:
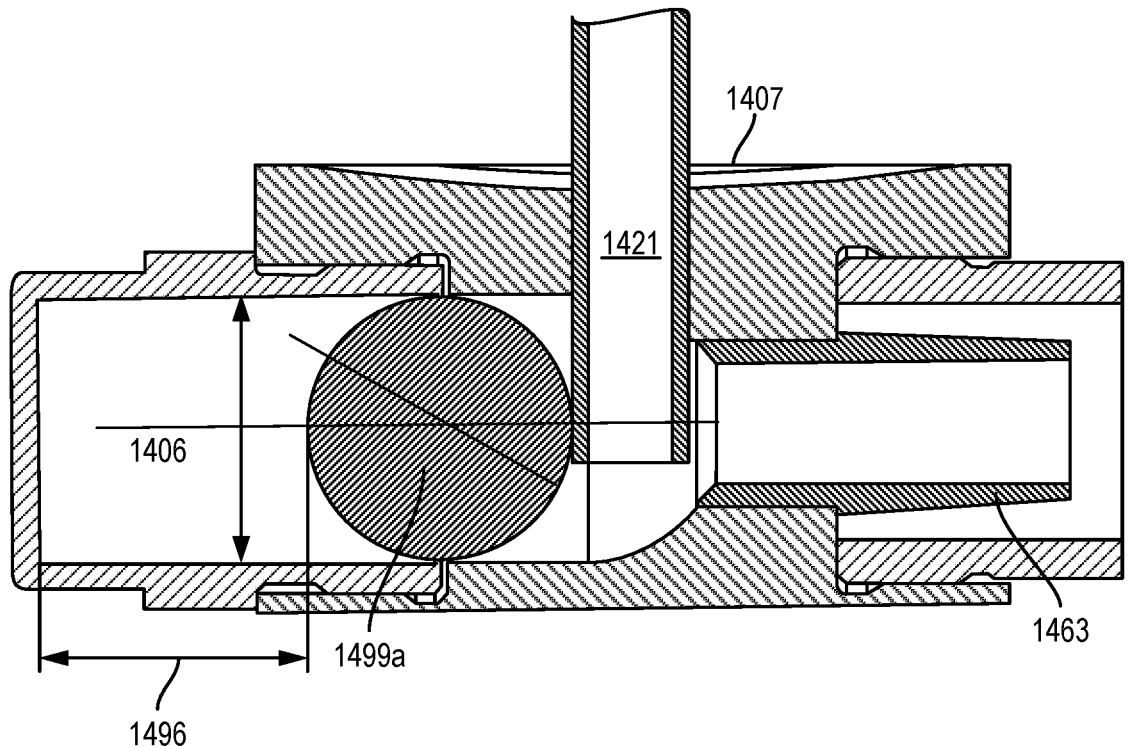
FIG. 14B is a cut-a-way side view illustration of a ball valve in an open position according to an embodiment of the invention.
Figure 14C:
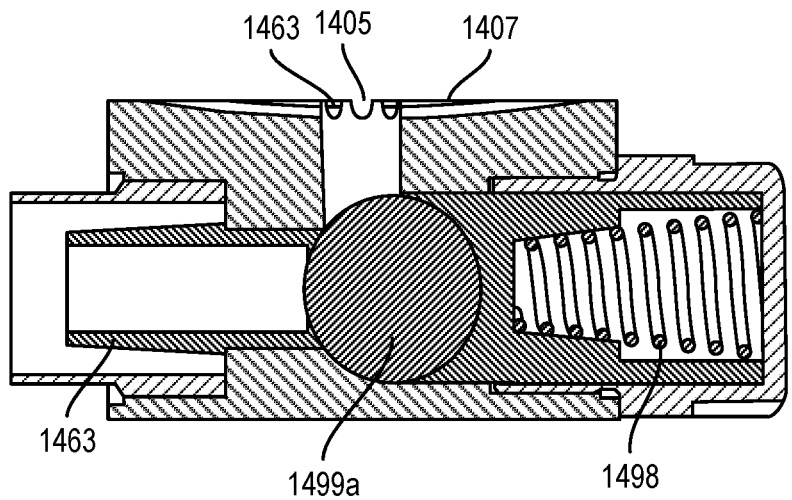
FIG. 14C is a cut-a-way side view illustration of a ball elastomer valve in a closed position according to an embodiment of the invention.

FIG. 14A is a cut-a-way side view illustration of a ball valve in a closed position according to an embodiment of the invention. A nozzle 1463 connects to a catheter (not shown) which ultimately taps into a blood flow path (i.e. a blood vessel). The opening of the tapered seat 1405 is closed to blood flow when the conduit is occluded by a spherical element 1499a (i.e. ball). When the access tube 1421 tracks down a guide 1463 on the flat surface 1407, the ball 1499a is laterally displaced by the access tube 1421 as the tube is inserted into the tapered seat. FIG. 14B shows the ball 1499a displaced in this manner to open the valve. An area 1406 provides a space for excursion of the ball 1499a. The ball 1499a is generally displaced the difference in the distances between distance 1497 (FIG. 14A) and distance 1996 (FIG. 14B). The flow path between the tip of the access tube 1421 and the out flow through the nozzle 1463 is thus opened to allow flow unobstructed by the access tube in use. The area 1406 may include an elastomeric spring 1498 (FIG. 14C) or silicone ring 1598 (FIG. 15), for example, in order to accommodate the displaced ball 1499a. Of course, other materials that add a resistant force against a displaced sphere may be used in area 1406.

FIGS. 14D1-14D4 are perspective views of a first spherical element 1449c portion of a valve mechanism according to an embodiment of the invention. FIGS. 14D1 and 14D2 are left and right side views respectively. FIGS. 14D3 and FIG. 14D4 are top and bottom views respectively. Both spherical elements 1449c, 1449d may be balls made of stainless steal, synthetic saffire or other hard material that is hard and lubricious.

FIG. 14D1 shows the locational relationship between the slot 1411b and recess 1410. The slot 1411b runs along a diameter located substantially opposite the recessed area 1410.

FIG. 14E1 is a side cut-a-way view of the slotted ball of FIGS. 14D1-14D4 positioned in an implantable port device 1464 according to an embodiment of the invention. This embodiment of a valve mechanism comprises a spring element 1415, a conical piston 1416, a washer 1421, a cup element 1422, a first spherical element 1449c and a second spherical element 1449d. The second spherical element 1449d has a smaller diameter than the first spherical element 1449c and the first spherical element has a recessed area 1410 configured to receive a portion of the second spherical element 1449c. When a needle is percutaneouly inserted into the tapered seat 1405 of the device, the needle contacts the slot 1411b in a substantially horizontal position and rotates the ball in direction 1425 (about 90 degress along an axis) to open the valve in a substantially vertical position. The second spherical element 1449d simultaneously rotates within the recessed portion 1410 as the first spherical element 1449c is rotated. The second spherical element 1449d transmits a compression force toward the conical portion 1416 when the valve is open.

FIGS. 14E2 and 14E3 are top and bottom views of conical portion 1416, respectively. FIGS. 14E4 and 14E5 are left and right views, respectively. As seen in various perspective views including FIGS. 14E3 and 14E4, the cup element 1422 has a slot 1417 and a groove 1418 located on one end of the slot 1417. The groove may be about 1.5 mm in diameter, for example. When element 1449d rotates, it migrates into groove 1418 thus creating a cam effect. The second spherical element 1449d transmits a compression force toward the conical portion when the valve is open. The force is translated from element 1449d to the conical piston and washer 1421. The washer 1421 (i.e. O-ring) is compressed into the cup element 1422 when the valve is open to seal the valve and prevent leakage. The tip 1420 of the conical portion 1416 closes a space 1423 between the spring 1415 and tip 1421. This, in turn, provides a resistant force against the needle when the valve is open. Removal of the needle relieves the force and the first spherical element 1449c rotatatably rebounds to the first position to close the valve.

FIG. 14E6 is a top view of a spring 1415 of the valve mechanism according to an embodiment of the invention. Area 1421 extends to the outer diameter of the spring to allow easy insertion of the spring near the tip 1420 of the conical piston 1416 during assembly. The spring 1415 may be made of metal, nitinol or similar material.

Figure 14F:
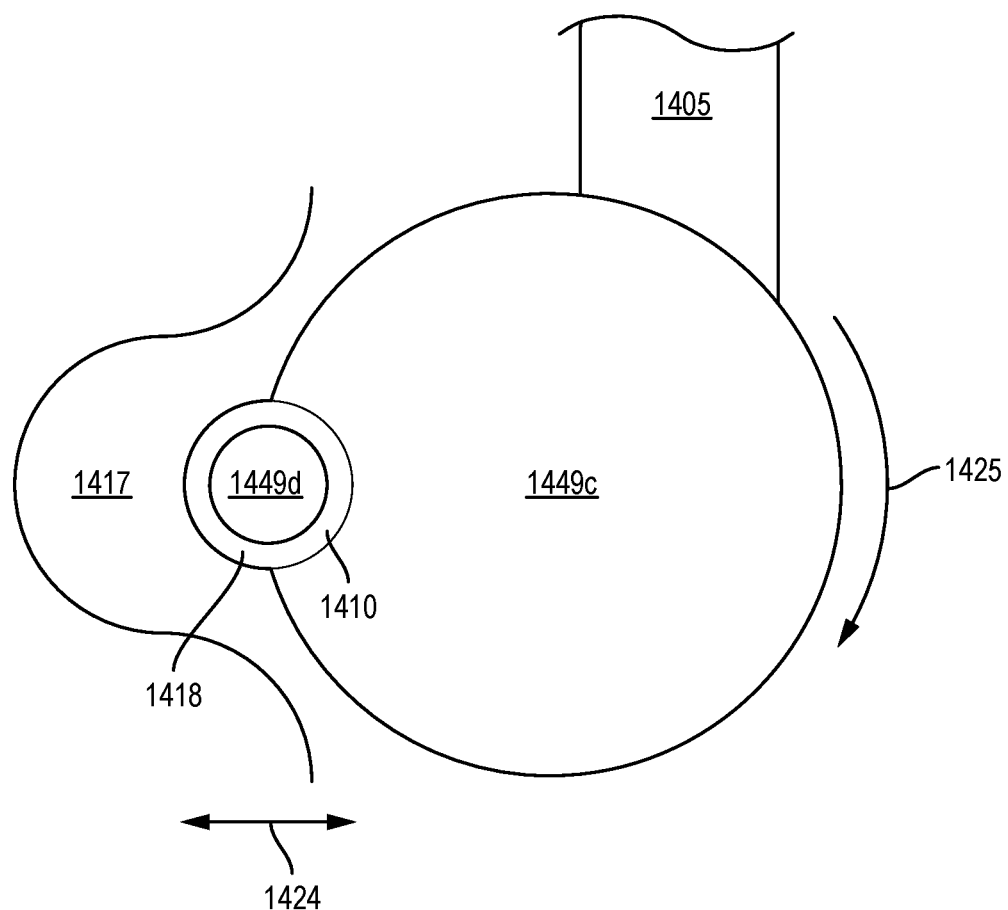
FIG. 14F is a side view of a value mechanism according to an embodiment of the invention.

Turning now to FIG. 14F, a side view of a value mechanism of FIGS. 14D1-14E6 is disclosed. This embodiment is advantageous in that it provides a durable device that minimizes wear and tear while increasing valve longevity because the first spherical element travels a very short distance 1424 (e.g. between about 1.0 mm and 1.7 mm) and the spring distance is also reduced. Additionally, the valve components (i.e. spring element 1415, conical piston 1416, washer 1421, cup element 1422, first spherical element 1449c and second spherical element 1449d) relax when the valve is closed which allows a lock solution to bathe the components between uses.

FIGS. 14G1-14G3 show an alternative valve mechanism using a slotted ball 1499b to open and close the valve. A single ball 1449b resides in the tube connecting the opening for the access tube 1405 with the conduit. The ball may be secured at a location in the tube by a circular area 1407b in a similar manner as described with respect to FIG. 14F. Note that unlike FIG. 14F, the slotted ball valve embodiment includes a single ball and the valve is no a pinch clamp valve mechanism. The ball 1499b has a slot 1411a running generally along half of the diameter of the ball. FIGS. 14G1 and 14G2 show the examples of the orientation of the ball when the valve is in the closed position. The access tube 1421 is inserted into the opening 1405 in the direction 1412 until it contacts the slotted ball 1499b. The contact rotates the ball 1499b in an axial direction 1413, allowing the access tube 1421 to track along the slot 1411a as the tube is inserted deeper into the tube to open the valve and tap into a blood flow path in the conduit. When the access tube 1499b is removed (e.g. retracted in the opposite direction of 1412) from the tube at the conclusion of treatment, the ball rotates back into the position shown in FIG. 14G1 to close the valve.

Figure 15:
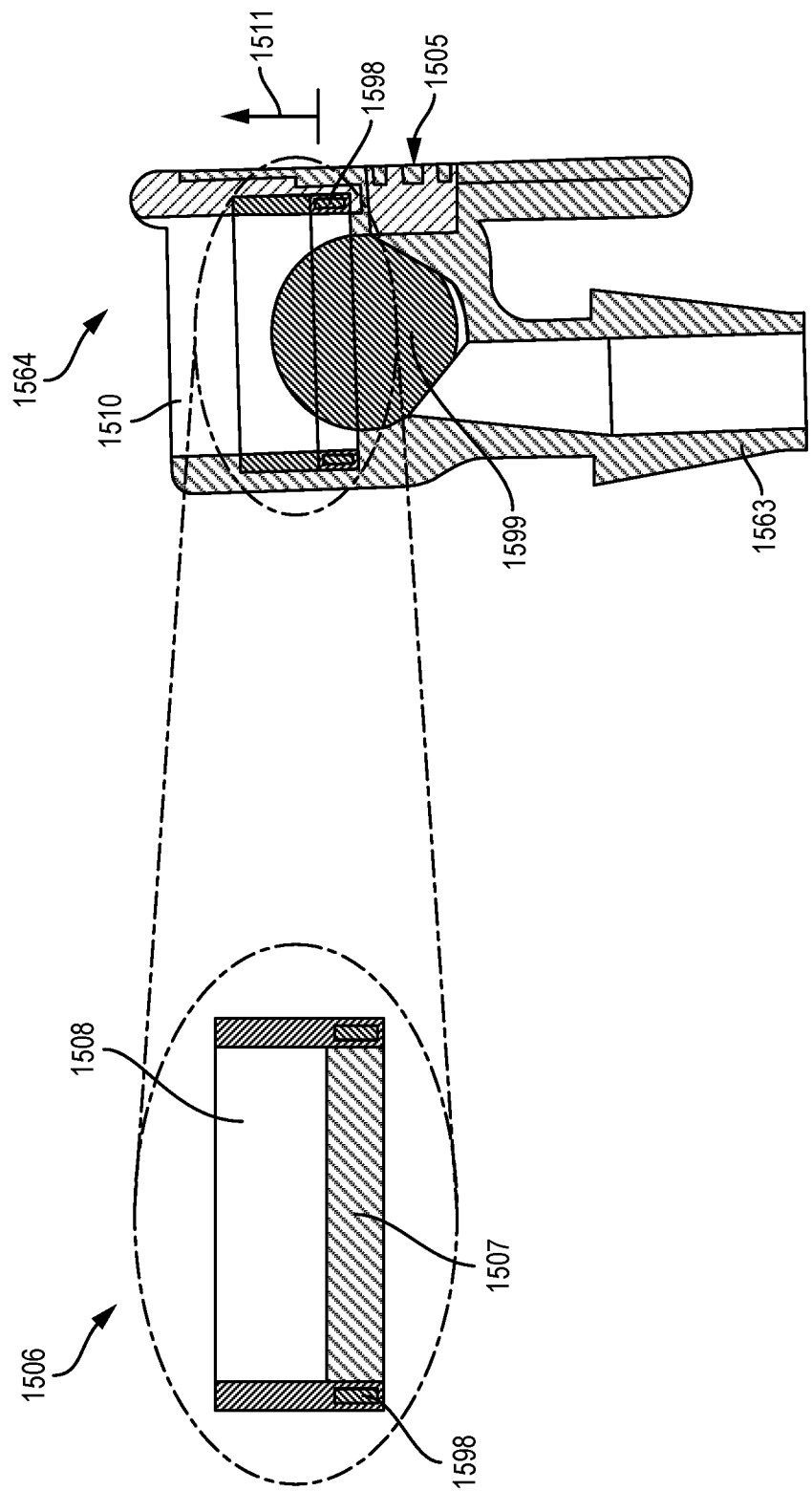
FIG. 15 is a cross sectional view of a silicon bumper spring configuration according to an embodiment of the invention.

FIG. 15 is a cross sectional view of a silicon bumper spring configuration. This is basically another way to receiving a ball 1599 in addition to the elastomeric spring 1498 embodiment shown in FIG. 14C. FIG. 15 shows the silicon bumper spring resting against the ball 1599 (or other spherical element) when the valve is closed. The ball is displaced by the access tube (not shown) during tube insertion through the opening 1505 and the ball pushes into the silicone. Area 1506 includes a layer of relatively soft silicone 1507 and an area of relatively hard silicone 1508 which is located furthest from the nozzle 1563 at the opposite end of the port device 1564. A metal spring 1598 is embedded in (and surrounds) the soft silicone portion 1507, The soft silicone 1507 provides the spring force and excursion of the ball 1599. The soft 1507 and hard 1508 silicone are fused together and the hard silicone 1508 is compressed to hold the silicone in place. In this manner, the spring does not extrude out the end 1510 but simply compresses the soft silicone 1507. When the ball 1599 is displaced and pushes further into the center of the soft silicon 1507 bumper in the direction 1511, the silicone is moved from the center to the outside. The metal spring 1598 adds rigidity to retain the leading edge of the silicone material as it compresses against the ball 1599 and moves outward from the center of the silicone. Other materials that add a resistant force against a displaced sphere may be used in area 1506. Although silicone is convenient to use in the human body, however, many polymeric or other materials may be used in combination.

Figure 16B:
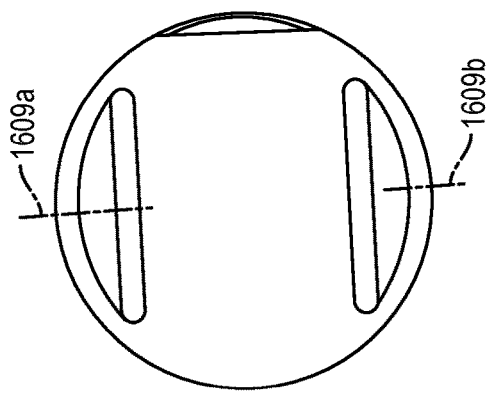
FIG. 16B is a bottom view illustration of a port housing with a ball bed of 90 degrees and an axial flow connector according to an embodiment of the invention.
Figure 16D:
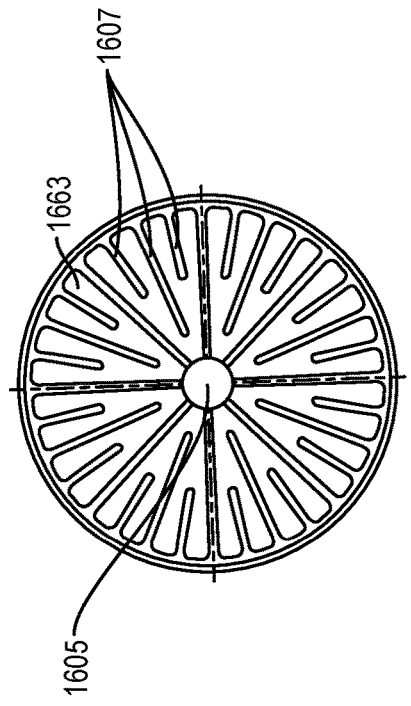
FIG. 16D is a top view illustration of a port housing with an axial connector according to an embodiment of the invention.
Figure 16A:
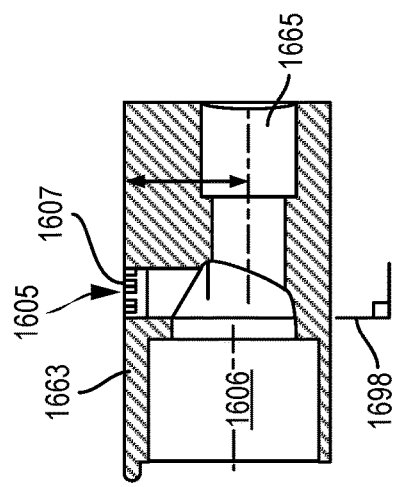
FIG. 16A is a cut-a-way side view illustration of a port housing with a ball bed of 90 degrees and an axial flow connector according to an embodiment of the invention.
Figure 16C:
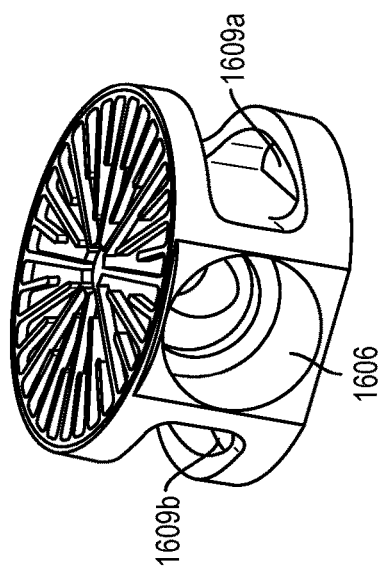
FIG. 16C is a perspective view of the port device of 16A and 16B.

FIG. 16A is a cut-a-way side view illustration of a port housing with a ball bed and an axial flow connector according to an embodiment of the invention. In this embodiment, the angle 1698 of the tube/tapered seat and outlet opening 1665 (which ultimately attaches to a catheter) is about 90 degrees. FIG. 16B is a bottom view illustration of a port housing with a ball bed and an axial flow connector according to an embodiment of the invention. FIG. 16C is a perspective view of the port device of 16A and 16B that includes suture rings 1609a, 1609b to stabilize the port when subcutaneously implanted. FIG. 16D is a top view illustration of a port housing with an axial connector according to an embodiment of the invention showing the flat surface 1663 and ridges 1607 that engage and guide the access tube into the opening 1605 of the tapered seat.

Figure 17A:
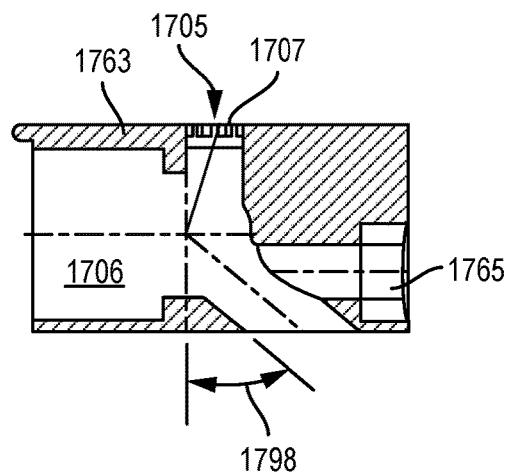
FIG. 17A is a cut-a-way side view illustration of a port housing with a ball bed of 40 degrees and an axial flow connector according to an embodiment of the invention.
Figure 17C:
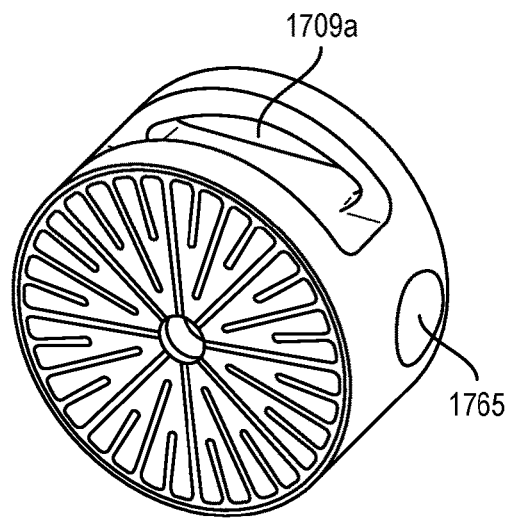
FIG. 17C is a perspective view of the port device of 17A and 17B.
Figure 17B:
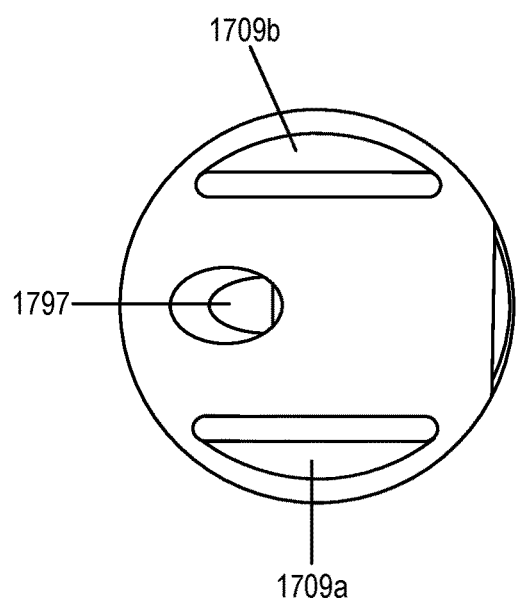
FIG. 17B is a bottom view illustration of a port housing with a ball bed of 40 degrees and an axial flow connector according to an embodiment of the invention.

FIG. 17A is a cut-a-way side view illustration of a port housing with a ball bed of 40 degrees boring and an axial flow connector according to an embodiment of the invention. It has been found that an angled ball bed (i.e. the resting area of the ball when the valve is closed to flow) of less than 90 degrees positions the ball so the access tube, when inserted through the opening 1705, engages the ball more eccentrically than an angle of 90 degrees. An angle 1798 of about 40 degrees is shown in FIG. 17A. This positions the ball so the access tube strikes the ball closer to the open end 1765. By engaging the ball at a location other than at its geometrical center, the health care professional need not supply as much force when the access tube is inserted into the tube. The ball more easily moves into the polymeric spring, silicone bumper spring or other similar structure. The point at which the ball contacts the access tube should be at least less than 90 degrees. An angle of between about 40 and 90 degrees between the tube (first vector) and the opening connecting the catheter (second vector) is preferred to easily move the ball and open the valve. FIG. 17B is a bottom view illustration of a port housing with a ball bed of 40 degrees with associated bore 1797. The bore 1797 is an example of a manufacturing technique that allows the ball to engage as described above. The bore 1797 is plugged closed after maching. The opening 1765 of the outflow tube is about 90 degrees relative to the opening 1705 of the tapered seat. FIG. 17C is a perspective view of the port device of 17A and 17B including an outlet opening 1765 which is attached to a catheter (not shown).

Figure 18C:
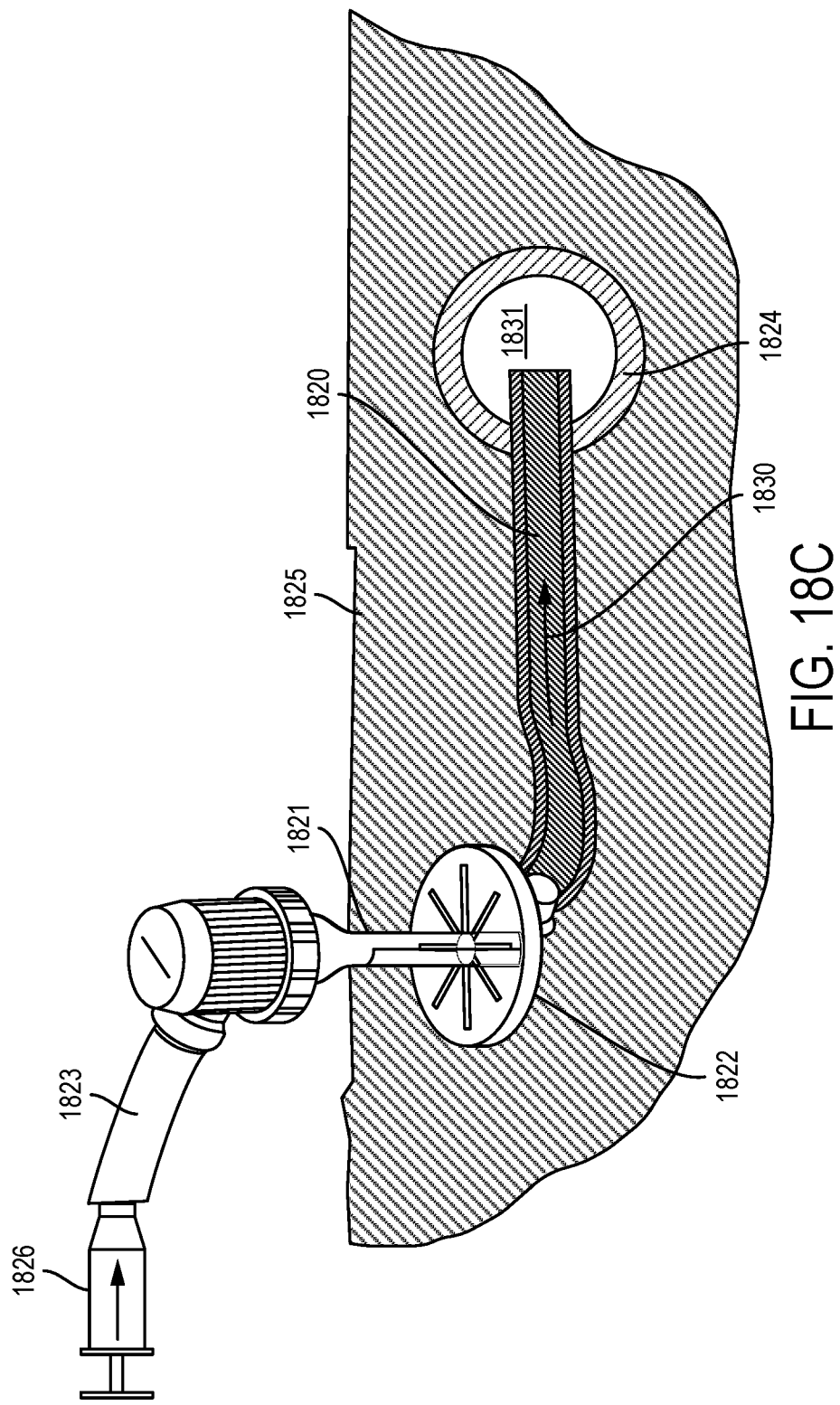

Referring now FIGS. 18A-18C, locking of a subcutaneously implanted catheter 1820 used for hemodialysis access will be described. The catheter 1820 is implanted under the skin between a target blood vessel 1824, typically a vein, and an implanted port 1822. During hemodialysis, blood 1831 may be withdrawn in a direction 1827 through the catheter 1820, through the port 1822 and externally through an access tube 1821 and connecting line 1823 used to percutaneously access the port 1822 (FIG. 18A). Alternatively, the port and catheter could be used to return treated blood to the patient.

When it is desired to end a hemodialysis (or hemofiltration) treatment, a flushing solution 1828 will be introduced in a direction 1829 through the access tube 1821 (typically from a syringe which is attached to the connecting line 1823) to flush the lumen, as depicted in FIG. 18B. After the flush is complete, a container such as syringe 1826 containing the hydrophobic antimicrobial lock solution of mid-chain fatty acid(s) and tocopherol/ricinoleic acid mixture is injected through the line 1823/port 1822 in a direction 1830 into the lumen of catheter 1820 to displace the flushing solution and lock the catheter (FIG. 18C). The lock solution will remain in place within the catheter 1820.

Figure 19A:
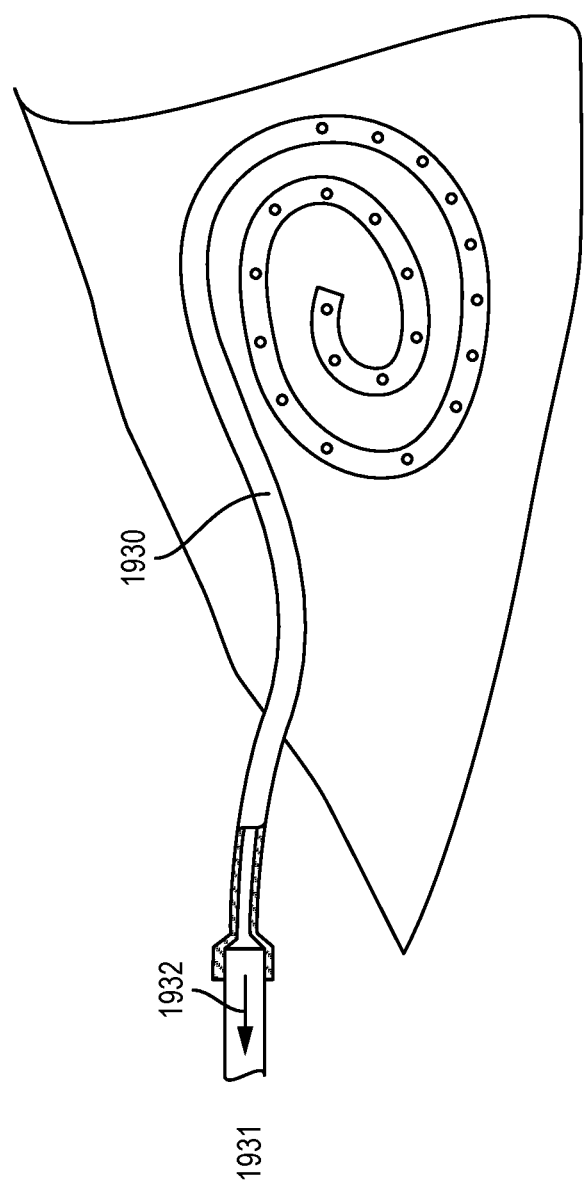
FIGS. 19A-19C illustrate methods of locking and disinfecting an implanted peritoneal dialysis catheter according to an embodiment of the invention.
Figure 19B:
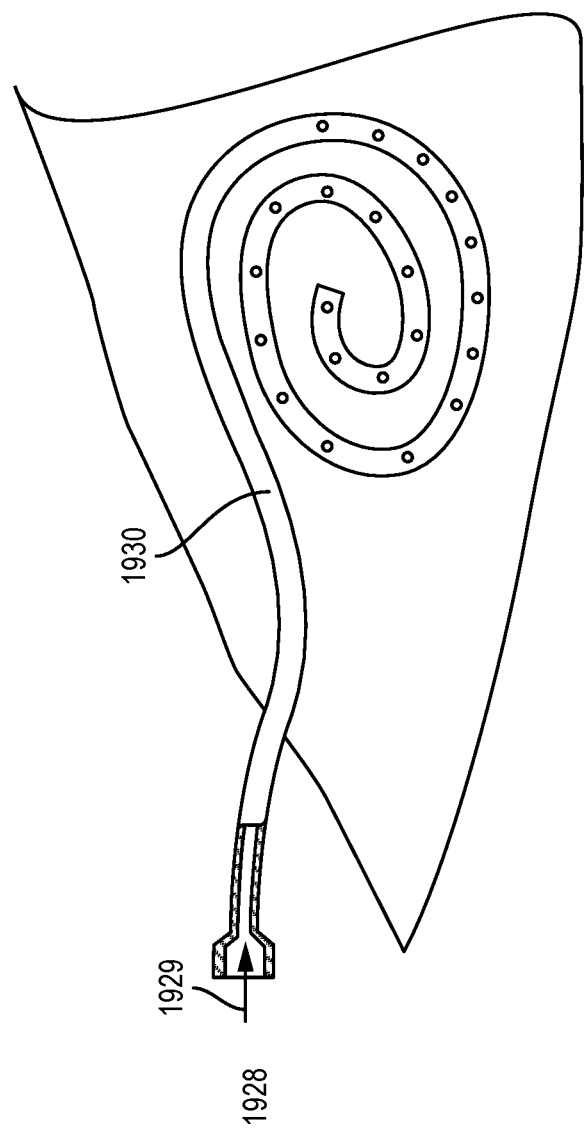
Figure 19C:
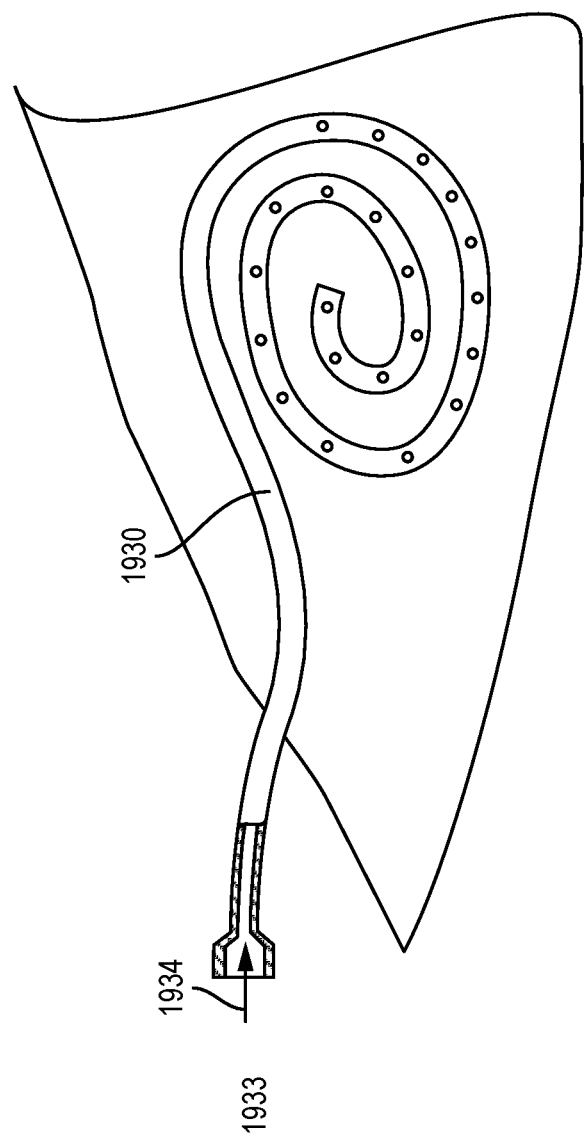

The methods of the present invention may also be used to lock non-vascular catheters, such as peritoneal dialysis catheters 1930, as shown in FIGS. 19A-19C. After a peritoneal dialysis treatment, the used dialysate 1931 will be withdrawn from the catheter 1930 in a direction 1932 as shown in FIG. 19A. After the dialysate has been sufficiently removed, the dialysis catheter 1930 may optionally be flushed in a direction 1929 with a flushing solution 1928, as shown in FIG. 19B. After flushing, the lock solution 1933 of mid-chain fatty acid(s) and tocopherol/ricinoleic acid mixture is introduced to the peritoneal dialysis catheter 1930 in direction 1934 as shown in FIG. 19C, so that it fills the lumen of the catheter, as described previously with the vascular catheters. The use of the aforementioned lock solution for peritoneal dialysis catheters is particularly advantageous in inhibiting or eliminating infections.

Figure 20:
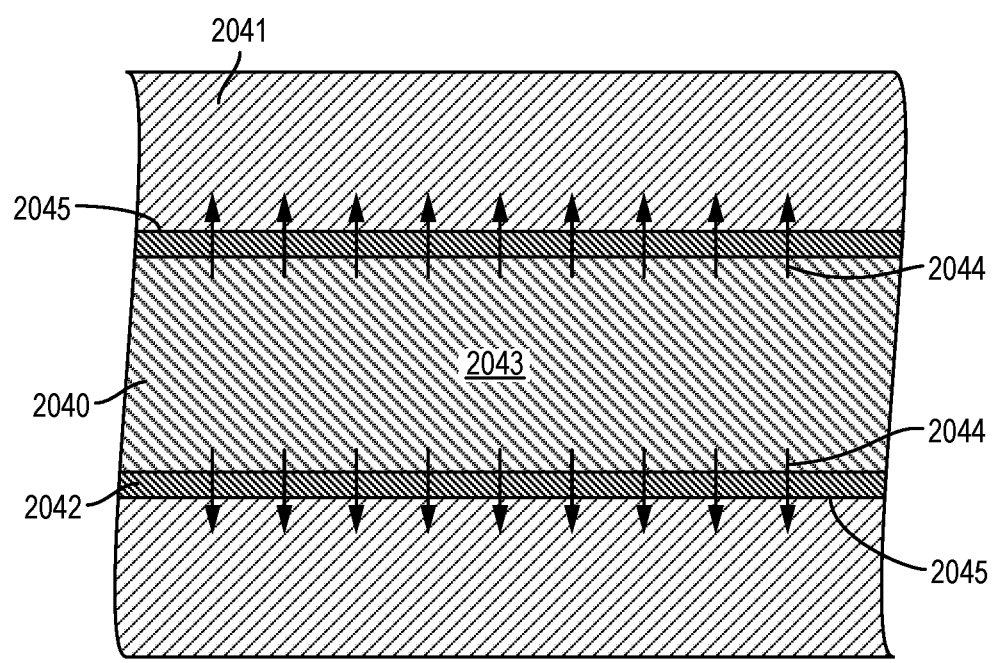
FIG. 20 illustrates an antimicrobial locking solution in a porous catheter seeping into tissue surrounding the catheter body according to an embodiment of the invention.

Referring now to FIG. 20, the use of a lock solution containing mid-chain fatty acid(s) and tocopherol and a mixture possessing desirable antimicrobial and anticoagulant properties for locking a catheter can be enhanced by utilizing an implanted catheter which is formed at least partially from a porous or semi-permeable material. When the lumen 2040 of the porous catheter body 2042 is filled with a hydrophobic antimicrobial lock solution of mid-chain fatty acid(s) and tocopherol mixture 2043, the solution will be able to slowly penetrate (i.e. seep or permeate) into the catheter body and preferably outwardly (as shown in direction 2044) into the tissue 2041 surrounding the catheter, as shown by the arrows in FIG. 20. Thus, the antimicrobial properties of the lock solution will not be entirely limited to the interior lumen 2040 of the catheter, but will also be effective on the surface of the catheter 2045 and in the tissue 2041 immediately surrounding the catheter body. The solution provides anti-thrombotic (catheter lock) and pro-thrombotic (needle site) qualities. Particularly suitable materials and porosity properties for the catheter bodies have been set forth above. The ability of ricinoleic acid to remove toxins from the blood may be particularly beneficial in peritoneal treatments. In addition, the solution serves to lubricate the implanted device including internal structures and valves.

Although embodiments of the invention have been described in considerable detail with reference to certain preferred versions thereof, other embodiments are possible.

Therefore, the spirit and scope of the appended claims should not be limited to the descriptions of the embodiments above.

What is claimed is:

1. A method for establishing access to a blood vessel of a patient, the method comprising:
   implanting a port device entirely under a skin of the patient, wherein the port device comprises:
   a first tapered seat configured to receive a tip of a first access tube, the first tapered seat having a proximal portion, a distal portion, and a conical section extending between the proximal portion and the distal portion;
   a second tapered seat for receiving a tip of a second access tube; and
   an interface surface configured to engage (i) the blood vessel of the patient or (ii) a vascular access catheter, the interface surface having an aperture in fluid communication with the distal portion of the first tapered seat;
   introducing the tip of the first access tube into the port device via the proximal portion of the first tapered seat;
   advancing the tip of the first access tube toward the distal portion of the first tapered seat to create a mismatch fit with a diameter of the tip of the first access tube along the conical section of the first tapered seat when the first tapered seat receives the first access tube in use, wherein the mismatch fit is adapted to cause an increase in flow during treatment; and
   advancing the tip of the second access tube toward a distal portion of the second tapered seat to create a match fit with a diameter of the second access tube.

2. The method of claim 1, wherein the mismatch fit is further configured to decrease a cross-sectional sealing area.

3. The method of claim 1, wherein a distance between the proximal portion and the distal portion of the first tapered seat is between about 1.0 mm and 5.0 mm.

4. The method of claim 1, wherein the tip of the first access tube is cylindrical.

5. The method of claim 1, further comprising:
   performing a first procedure via the first tapered seat, wherein the first procedure is at a flow rate greater than normal physiological pressures; and
   performing a second procedure via the second tapered seat, wherein the second procedure is at a flow rate less than normal physiological pressures.

6. The method of claim 5, wherein the first procedure comprises an injection of contrast dyes or a dialysis procedure.

7. The method of claim 5, wherein the second procedure comprises an injection of intravenous fluids.

8. The method of claim 5, wherein at least part of the first procedure and at least part of the second procedure are performed simultaneously.

9. The method of claim 1, further comprising illuminating one or more light sources on a guide of the port device, wherein the guide is configured to engage the proximal portion of the tip of the first access tube and to assist in directing the tip of the first access tube toward the first tapered seat, and wherein illumination of the one or more light sources causes the one or more light sources to be visible through a skin of the patient.

10. The method of claim 9, wherein the port device comprises a receiver coil for receiving an electrical current, the method further comprising: positioning an electromagnetic inducer in proximity to the receiver coil to cause the one or more light sources to be illuminated.

11. The method of claim 10, wherein a location of the first tapered seat is illuminated by the one or more light sources so as to be visible through the skin of the patient, wherein any of:
   the one or more light sources include a durable radiant material;
   the one or more light sources include ruby or sapphire; and
   the device further includes a valve mechanism having a spherical element made of synthetic sapphire.

12. The method of claim 1, wherein the device is implanted so that the device is disposed and anchored entirely within subcutaneous tissue.

13. The method of claim 1, wherein the diameter of the distal end of the first access tube is greater than a diameter of the distal portion of the first tapered seat.

14. A fully implantable port device for establishing access to a blood vessel of a patient that is configured to be implanted entirely underneath the skin of the patient, the device comprising:
   a first tapered seat configured to receive a tip of a first access tube, the first tapered seat having a proximal portion, a distal portion, and a conical section extending between the proximal portion and the distal portion;
   a second tapered seat for receiving a tip of a second access tube; and
   an interface surface configured to engage (i) the blood vessel of the patient or (ii) a vascular access catheter, the interface surface having an aperture in fluid communication with the distal portion of the first tapered seat;
   wherein the proximal portion of the first tapered seat is configured to receive the tip of the first access tube therethrough,
   wherein the first tapered seat is configured to create a mismatch fit with a diameter of the tip of the first access tube along the conical section when in use, wherein the mismatch fit is adapted to cause an increase in flow during treatment, and
   wherein the second tapered seat is configured to create a match fit with a diameter of the second access tube when in use.

15. The device of claim 14, wherein the mismatch fit is further configured to decrease a cross-sectional sealing area.

16. The device of claim 14, wherein a distance between the proximal portion and the distal portion of the first tapered seat is between about 1.0 mm and 5.0 mm.

17. The device of claim 14, wherein the tip of the first access tube is cylindrical.

18. The device of claim 14, wherein the first tapered seat is configured for use in procedures requiring flow rates greater than normal physiological pressures, and wherein the second tapered seat is configured for use in procedures requiring flow rates less than normal physiological pressures.

19. The device of claim 18, wherein the first tapered seat is configured for injection of contrast dyes or performing dialysis procedures.

20. The device of claim 18, wherein the second tapered seat is configured for injection of intravenous fluids.

21. The device of claim 18, wherein the first and second tapered seats are configured for simultaneous use.

22. The device of claim 14, further comprising a guide configured to engage the proximal portion of the tip of the first access tube and to assist in directing the tip of the first access tube toward the first tapered seat, wherein the guide comprises one or more light sources configured to be illuminated so as to be visible through a skin of the patient.

23. The device of claim 22, further comprising a receiver coil for receiving an electrical current, wherein the one or more light sources are configured to be illuminated when an electromagnetic inducer is positioned in proximity to the receiver coil.

24. The device of claim 22, wherein the one or more light sources are configured to illuminate a location of the first tapered seat so that the first tapered seat is visible to a user inserting the access tube through the skin of the patient, wherein any of:
- the one or more light sources include a durable radiant material;
- the one or more light sources include ruby or sapphire; and
- the device further includes a valve mechanism having a spherical element made of synthetic sapphire.

25. The device of claim 14, wherein the diameter of the distal end of the first access tube is greater than a diameter of the distal portion of the first tapered seat.

\* \* \* \* \*